United States Patent
Boyanov et al.

(10) Patent No.: US 10,633,694 B2
(45) Date of Patent: Apr. 28, 2020

(54) COMPOSITIONS, SYSTEMS, AND METHODS FOR DETECTING THE PRESENCE OF POLYMER SUBUNITS USING CHEMILUMINESCENCE

(71) Applicant: ILLUMINA, INC., San Diego, CA (US)

(72) Inventors: Boyan Boyanov, San Diego, CA (US); Liangliang Qiang, San Diego, CA (US); Kevin L. Gunderson, San Diego, CA (US); Kay Klausing, San Diego, CA (US); Lea Pickering, Nr. Saffron Walden (GB); Cyril Delattre, San Diego, CA (US); Tarun Khurana, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 11 days.

(21) Appl. No.: 15/507,465

(22) PCT Filed: Sep. 10, 2015

(86) PCT No.: PCT/US2015/049393
§ 371 (c)(1),
(2) Date: Feb. 28, 2017

(87) PCT Pub. No.: WO2016/040607
PCT Pub. Date: Mar. 17, 2016

(65) Prior Publication Data
US 2017/0356030 A1    Dec. 14, 2017

Related U.S. Application Data

(60) Provisional application No. 62/049,883, filed on Sep. 12, 2014, provisional application No. 62/092,693, filed on Dec. 16, 2014.

(51) Int. Cl.
*C12Q 1/68* (2018.01)
*C12Q 1/6818* (2018.01)
*C12Q 1/6874* (2018.01)
*C12Q 1/6816* (2018.01)

(52) U.S. Cl.
CPC ......... *C12Q 1/6818* (2013.01); *C12Q 1/6816* (2013.01); *C12Q 1/6874* (2013.01); *C12Q 2533/101* (2013.01); *C12Q 2535/113* (2013.01); *C12Q 2535/122* (2013.01); *C12Q 2563/103* (2013.01); *C12Q 2563/125* (2013.01)

(58) Field of Classification Search
None
See application file for complete search history.

(56) References Cited

U.S. PATENT DOCUMENTS

| | | | |
|---|---|---|---|
| 6,737,236 B1 | 5/2004 | Pieken | |
| 7,057,026 B2 | 6/2006 | Barnes | |
| 7,211,414 B2 | 5/2007 | Hardin | |
| 7,259,258 B2 | 8/2007 | Kozlov | |
| 7,315,019 B2 | 1/2008 | Turner | |
| 7,329,492 B2 | 2/2008 | Hardin | |
| 7,329,860 B2 | 2/2008 | Feng | |
| 7,375,234 B2 | 5/2008 | Sharpless | |
| 7,405,281 B2 | 7/2008 | Xu | |
| 7,427,678 B2 | 9/2008 | Pieken | |
| 8,778,848 B2 | 7/2014 | Lin | |
| 8,778,849 B2 | 7/2014 | Bowen | |
| 2008/0037008 A1* | 2/2008 | Shepard | G01N 21/6408 356/73 |
| 2008/0108082 A1 | 5/2008 | Rank | |
| 2008/0280773 A1 | 11/2008 | Fedurco | |
| 2009/0325172 A1 | 12/2009 | Milton | |
| 2010/0093553 A1* | 4/2010 | Park | C40B 50/18 506/9 |
| 2010/0105049 A1* | 4/2010 | Ehrich | C12Q 1/6804 435/6.12 |
| 2010/0111768 A1 | 5/2010 | Banerjee | |
| 2011/0091474 A1* | 4/2011 | Zhang | C12Q 1/6883 424/158.1 |
| 2011/0097723 A1 | 4/2011 | Liu | |
| 2011/0059865 A1 | 5/2011 | Smith | |
| 2013/0079232 A1 | 3/2013 | Kain | |
| 2013/0116128 A1 | 5/2013 | Shen | |

FOREIGN PATENT DOCUMENTS

| | | |
|---|---|---|
| WO | WO 1991/006678 | 5/1991 |
| WO | WO 1999/054503 | 10/1999 |

(Continued)

OTHER PUBLICATIONS

Anonymous: Instructions: Chemiluminescent nucleic acid detection module (2011), pp. 1-3, retrieved from internet URL:https://tools.thermofisher.com/content/sfs/manuals/MAN0011520_Chemiluminescent_NucAcid_Detect_Mod_UG.pdf.

(Continued)

*Primary Examiner* — James Martinell
(74) *Attorney, Agent, or Firm* — Knobbe Martens, Olson & Bear LLP

(57) ABSTRACT

Under one aspect, a composition includes a substrate; a first polynucleotide coupled to the substrate; a second polynucleotide hybridized to the first polynucleotide; and a catalyst coupled to a first nucleotide of the second polynucleotide, the catalyst being operable to cause a chemiluminogenic molecule to emit a photon. Under another aspect, a method includes providing a catalyst operable to cause a first chemiluminogenic molecule to emit a photon; providing a substrate; providing a first polynucleotide coupled to the substrate; hybridizing a second polynucleotide to the first polynucleotide; coupling a first quencher to a first nucleotide of the second polynucleotide; and inhibiting, by the first quencher, photon emission by the first chemiluminogenic molecule.

18 Claims, 35 Drawing Sheets

Specification includes a Sequence Listing.

(56) References Cited

FOREIGN PATENT DOCUMENTS

| WO | WO 2002/077287 | 10/2002 |
|---|---|---|
| WO | WO 2003/020895 | 3/2003 |
| WO | WO 2003/029491 | 4/2003 |
| WO | WO 2004/018497 | 3/2004 |
| WO | WO 2005/007874 | 1/2005 |
| WO | WO 2005/065814 | 7/2005 |
| WO | WO 2006/041745 | 4/2006 |
| WO | WO 2006/091628 | 8/2006 |
| WO | WO 2007/123744 | 11/2007 |

OTHER PUBLICATIONS

Bentley et al., Accurate whole human genome sequencing using reversible terminator chemistry, *Nature* 456:53-59 (2008).

Boute et al., The use of resonance energy transfer in high-throughput screening: BRET versus FRET, Trends in Pharmacological Sciences 23(8): 351-354 (Aug. 1, 2002).

Daeid et al., Synthetic porphyrins/metalloporphyrins which mimic states in catalytic cycle of cytochrome P-450 and peroxidases, Pure and Applied Chemistry 65(7): 1541-1548 (1993).

Fan, et al, Chemiluminescence platforms in immunoassay and DNA analysis, Anal Chem 25(5):587-597 (2009).

Giraud et al., Fluorescence lifetime biosensing with DNA microassays and a CMOS-SPAD imager, Biomedical Optics Express 1: 1302-1308 (2010).

Stoppa et al., A 32 x 32-pixel array with in-pixel photon counting and arrival time measurement in the analog domain; Proceedings of the ESSCIRC 2009; Athens, Greece. Sep. 14-18, 2009; pp. 204-207.

Xu et al, Manganese Porphyrin-dsDNA Complex: A Mimicking Enzyme for Highly Efficient Bioanalysis, Analytical Chemistry 85: 3374-3379 (2013).

Kakihara, et al., MagSNiPer: A new single nucleotide polymorphism typing method based on single base extension, magnetic separation and chmiluminescence, Analytical Biochemistry 341(1):77-82 (2005).

\* cited by examiner

COMPOSITIONS, SYSTEMS, AND METHODS FOR DETECTING THE PRESENCE OF POLYMER SUBUNITS USING CHEMILUMINESCENCE

CROSS-REFERENCE TO RELATED APPLICATIONS

This application is the U.S. National Phase of Int. App. No. PCT/US2015/049393 filed Sep. 10, 2015 and published in English as Int. Pub. No. WO 20016/040607 on Mar. 17, 2016 which claims the benefit of U.S. Prov. App. No. 62/049,883, filed Sep. 12, 2014 and entitled "Compositions, Systems, and Methods for Detecting the Presence of Polymer Subunits Using Chemiluminescence", and U.S. Prov. App. No. 62/092,693, filed Dec. 16, 2014 and entitled "Compositions, Systems, and Methods for Detecting the Presence of Polymer Subunits Using Chemiluminescence" which are each incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 9, 2015, is named 12957-173-228_SL.txt and is 1,890 bytes in size.

FIELD

This application generally relates to detecting the presence of a polymer subunit.

BACKGROUND

The detection of analytes such as nucleic acid sequences that are present in a biological sample has been used as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting analytes such as nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of thousands of nucleic acids all in a single sequencing run. The instrumentation that performs such methods is typically large and expensive since the current methods typically rely on large amounts of expensive reagents and multiple sets of optic filters to record nucleic acid incorporation into sequencing reactions.

It has become clear that the need for high-throughput, smaller, less expensive DNA sequencing technologies will be beneficial for reaping the rewards of genome sequencing. Personalized healthcare is moving toward the forefront and will benefit from such technologies; the sequencing of an individual's genome to identify potential mutations and abnormalities will be crucial in identifying if a person has a particular disease, followed by subsequent therapies tailored to that individual. To accommodate such an aggressive endeavor, sequencing should move forward and become amenable to high throughput technologies not only for its high throughput capabilities, but also in terms of ease of use, time and cost efficiencies, and clinician access to instruments and reagents.

SUMMARY

Embodiments of the present invention provide compositions, systems, and methods for detecting the presence of polymer subunits using chemiluminescence.

Under one aspect, a composition includes a substrate; a first polynucleotide coupled to the substrate; a second polynucleotide hybridized to the first polynucleotide; and a catalyst coupled to a first nucleotide of the second polynucleotide, the catalyst being operable to cause a chemiluminogenic molecule to emit a photon.

In some embodiments, the composition further includes a plurality of the chemiluminogenic molecules. The catalyst can cause each of the chemiluminogenic molecules to emit a corresponding photon. The composition further can include a plurality of reagent molecules, the catalyst causing each of the chemiluminogenic molecules to emit a corresponding photon by oxidizing that chemiluminogenic molecule using a reagent molecule. The oxidized chemiluminogenic molecule can have an excited state that decays by emitting the corresponding photon.

In some embodiments, the catalyst is cleavable from the first nucleotide.

In some embodiments, the catalyst is coupled to the first nucleotide via a first moiety coupled to the nucleotide, and a second moiety coupled to the first moiety and to the catalyst. In one illustrative example, one of the first and second moieties can be biotin or a biotin derivative, and the other of the first and second moieties can be streptavidin. In another illustrative example, one of the first and second moieties is digoxigenin, and the other of the first and second moieties is anti-digoxigenin.

In some embodiments, the catalyst includes an enzyme. In one illustrative example, the enzyme includes a luciferase, and the chemiluminogenic molecule includes luciferin or a luciferin derivative. In another illustrative example, the enzyme includes a luciferase, and the chemiluminogenic molecule includes coelenterazine or a coelenterazine derivative. In yet another illustrative example, the enzyme includes a 1,2-dioxetane cleaver, and the chemiluminogenic molecule includes a 1,2-dioxetane derivative.

In some embodiments, the catalyst includes a peroxide generator, and the chemiluminogenic molecule includes luminol or a luminol derivative. In one illustrative example, the peroxide generator can include an enzyme. In another illustrative example, the peroxide generator can include a metallic, organic, or metalorganic catalyst.

In some embodiments, the catalyst includes a peroxide generator, and the chemiluminogenic molecule includes acridinium or an acridinium derivative. In one illustrative example, the peroxide generator can include an enzyme. In another illustrative example, the peroxide generator can include a metallic, organic, or metalorganic catalyst.

A system can include any of the foregoing compositions and circuitry configured to detect the photon emitted by the chemiluminogenic molecule. In some embodiments, the circuitry further is configured to detect the presence of the first nucleotide based on detection of the photon.

Under another aspect, a method can include providing a substrate; providing a first polynucleotide coupled to the substrate; hybridizing a second polynucleotide to the first polynucleotide; coupling a first catalyst to a first nucleotide of the second polynucleotide; and causing, by the first catalyst, a first chemiluminogenic molecule to emit a photon.

In some embodiments, the method further includes providing a plurality of the first chemiluminogenic molecules. In some embodiments, the method further includes causing, by the first catalyst, each of the first chemiluminogenic molecules to emit a corresponding photon. In some embodiments, the method further includes providing a plurality of reagent molecules and causing, by the first catalyst, each of the first chemiluminogenic molecules to emit a corresponding photon by oxidizing that first chemiluminogenic molecule using a reagent molecule. In some embodiments, the oxidized first chemiluminogenic molecule has an excited state that decays by emitting the corresponding photon.

In some embodiments, the method further includes coupling a polymerase to the first and second polynucleotides. The polymerase can add a second nucleotide to the second polynucleotide. In some embodiments, the method further can include cleaving the first catalyst from the first nucleotide before coupling the polymerase to the first and second polynucleotides. In some embodiments, the method further can include adding the second nucleotide to the first polynucleotide after coupling the polymerase to the first and second polynucleotides. In some embodiments, the method further can include coupling a second catalyst to the second nucleotide. In some embodiments, the second catalyst is coupled to the second nucleotide after adding the second nucleotide to the second polynucleotide. In some embodiments, the second nucleotide is coupled to a first moiety, the second catalyst is coupled to a second moiety, and said second catalyst is coupled to the second nucleotide by coupling the second moiety to the first moiety. In some embodiments, the method further includes causing, by the second catalyst, a second chemiluminogenic molecule to emit a photon.

In some embodiments, the first catalyst and the second catalyst are the same type of catalyst as one another. The first chemiluminogenic molecule and the second chemiluminogenic molecule can be the same type of chemiluminogenic molecule as one another. In other embodiments, the first catalyst and the second catalyst are different types of catalysts than one another. The first chemiluminogenic molecule and the second chemiluminogenic molecule can be different types of chemiluminogenic molecules than one another.

In some embodiments, the first nucleotide is coupled to a third moiety, the first catalyst is coupled to a fourth moiety, and said first catalyst is coupled to the first nucleotide by coupling the fourth moiety to the third moiety. Illustratively, the first moiety and the third moiety can be different than one another. Illustratively, the second moiety and the fourth moiety can be different than one another.

In some embodiments, the method further can include detecting the photon emitted by the second chemiluminogenic molecule. In some embodiments, the method further can include detecting the presence of the second nucleotide based on detection of the photon. In some embodiments, the method further can include detecting the photon emitted by the first chemiluminogenic molecule. In some embodiments, the method further includes detecting the presence of the first nucleotide based on detection of the photon emitted by the first chemiluminogenic molecule. In some embodiments, the method further includes cleaving the first catalyst from the first nucleotide.

In some embodiments, the first nucleotide is coupled to a first moiety, the first catalyst is coupled to a second moiety, and said first catalyst is coupled to the first nucleotide by coupling the first moiety to the second moiety. In one illustrative example, one of the first and second moieties is biotin or a biotin derivative, and the other of the first and second moieties is streptavidin. In another illustrative example, one of the first and second moieties is digoxigenin, and the other of the first and second moieties is anti-digoxigenin.

In some embodiments, the catalyst includes an enzyme. In one illustrative example, the enzyme includes a luciferase, and the chemiluminogenic molecule includes a luciferin or a luciferin derivative. In another illustrative example, the enzyme includes a luciferase, and the chemiluminogenic molecule includes coelenterazine or a coelenterazine derivative. In yet another illustrative example, the enzyme includes a 1,2-dioxetane cleaver, and the chemiluminogenic molecule includes a 1,2-dioxetane derivative.

In some embodiments, the catalyst includes a peroxide generator, and the chemiluminogenic molecule includes luminol or a luminol derivative. In one illustrative example, the peroxide generator includes an enzyme. In another illustrative example, the peroxide generator includes a metallic, organic, or metalorganic catalyst.

In some embodiments, the catalyst includes a peroxide generator, and the chemiluminogenic molecule includes acridinium or an acridinium derivative. In one illustrative example, the peroxide generator includes an enzyme. In another illustrative example, the peroxide generator includes a metallic, organic, or metalorganic catalyst.

In some embodiments, the method further includes detecting the photon emitted by the first chemiluminogenic molecule. In some embodiments, the method further includes detecting the presence of the first subunit based on detection of the photon emitted by the first chemiluminogenic molecule.

Under another aspect, a method of sequencing a first polynucleotide includes providing the first polynucleotide to be sequenced and coupled to a substrate; b) hybridizing a second polynucleotide to the first polynucleotide; and contacting the second polynucleotide with a polymerase and a plurality of nucleotides. A first subset of the plurality of nucleotides includes a first moiety, a second subset of the plurality of nucleotides includes a second moiety, a third subset of the plurality of nucleotides includes a third moiety, and a fourth subset of the plurality of nucleotides includes a fourth moiety or no moiety. The method further can include adding a nucleotide of the plurality of nucleotides to the second polynucleotide based on a sequence of the first polynucleotide. The method further can include exposing the nucleotide to a catalyst coupled to a fifth moiety; exposing the nucleotide to chemiluminogenic molecules; and detecting emission of photons or an absence of photons from the chemiluminogenic molecules. The method further can include exposing the nucleotide to a catalyst coupled to a sixth moiety; exposing the nucleotide to chemiluminogenic molecules; and detecting emission of photons or an absence of photons from the chemiluminogenic molecules. The method further can include exposing the nucleotide to a cleaver molecule; exposing the nucleotide to chemiluminogenic molecules; and detecting emission of photons or an absence of photons from the chemiluminogenic molecules. The method further can include detecting the added nucleotide based on the detection of emission of photons or absence of photons from the chemiluminogenic molecules at one or more of the detection steps or a combination thereof.

Under another aspect, a composition includes a catalyst operable to cause a chemiluminogenic molecule to emit a photon; a substrate; a first polynucleotide coupled to the substrate; a second polynucleotide hybridized to the first polynucleotide; and a quencher coupled to a first nucleotide of the second polynucleotide, the quencher operable to inhibit photon emission by the chemiluminogenic molecule.

Some embodiments further include a plurality of the chemiluminogenic molecules. In some embodiments, the quencher inhibits photon emission by each of the chemiluminogenic molecules. Some embodiments further include a plurality of reagent molecules, the catalyst causing each of the chemiluminogenic molecules to emit a corresponding photon by oxidizing that chemiluminogenic molecule using a reagent molecule in the absence of the quencher. In some embodiments, the oxidized chemiluminogenic molecule has an excited state that decays by emitting the corresponding photon in the absence of the quencher.

In some embodiments, the catalyst is coupled to the substrate. In some embodiments, the catalyst is coupled to the first polynucleotide. In some embodiments, the quencher is cleavable from the first nucleotide.

In some embodiments, the quencher is coupled to the first nucleotide via a first moiety coupled to the first subunit, and a second moiety coupled to the first moiety and to the quencher. In one illustrative example, one of the first and second moieties is biotin or a biotin derivative, and the other of the first and second moieties is streptavidin. In another illustrative example, one of the first and second moieties is digoxigenin, and the other of the first and second moieties is anti-digoxigenin.

In some embodiments, the catalyst includes an enzyme. In one illustrative example, the enzyme includes a luciferase, and the chemiluminogenic molecule includes a luciferin or a luciferin derivative. In another illustrative example, the enzyme includes a luciferase, and the chemiluminogenic molecule includes coelenterazine or a coelenterazine derivative. In yet another illustrative example, the enzyme includes a 1,2-dioxetane cleaver, and the chemiluminogenic molecule includes a 1,2-dioxetane derivative.

In some embodiments, the catalyst includes a peroxide generator, and the chemiluminogenic molecule includes luminol or a luminol derivative. In one illustrative example, the peroxide generator includes an enzyme. In another illustrative example, the peroxide generator includes a metallic, organic, or metalorganic catalyst.

In some embodiments, the catalyst includes a peroxide generator, and the chemiluminogenic molecule includes acridinium or an acridinium derivative. In one illustrative example, the peroxide generator includes an enzyme. In another illustrative example, the peroxide generator includes a metallic, organic, or metalorganic catalyst.

In some embodiments, the quencher is selected from the group consisting of DABCYL Quencher, BHQ-1® Quencher, BHQ-2® Quencher, BHQ-3® Quencher, ECLIPSE Quencher, BHQ-0 Dark Quencher, ELLEQUENCHER, IOWA BLACK® Quencher, (±)-6-hydroxy-2,5,7,8-tetramethylchromane-2-carboxylic acid (trade name Trolox), QSY 7 quencher, QSY 9 quencher, QSY 21 quencher, and QSY 35 quencher.

A system can include any of the foregoing compositions and circuitry configured to detect a photon emitted by the chemiluminogenic molecule. In some embodiments, the circuitry further is configured to detect the presence of the first nucleotide based on inhibition of emission of the photon.

Under another aspect, a method includes providing a catalyst operable to cause a first chemiluminogenic molecule to emit a photon; providing a substrate; providing a first polynucleotide coupled to the substrate; hybridizing a second polynucleotide to the first polynucleotide; coupling a first quencher to a first nucleotide of the second polynucleotide; and inhibiting, by the first quencher, photon emission by the first chemiluminogenic molecule.

In some embodiments, the method further includes providing a plurality of the first chemiluminogenic molecules. In some embodiments, the method further includes causing, by the first catalyst, each of the first chemiluminogenic molecules to emit a corresponding photon in the absence of the quencher. In some embodiments, the method further includes providing a plurality of reagent molecules, the first catalyst operable to cause each of the first chemiluminogenic molecules to emit a corresponding photon by oxidizing that first chemiluminogenic molecule using a reagent molecule in the absence of the quencher. In some embodiments, the oxidized first chemiluminogenic molecule has an excited state that decays by emitting the corresponding photon in the absence of the quencher.

In some embodiments, the method further includes coupling a polymerase to the first and second polynucleotides. In some embodiments, the polymerase adds a second nucleotide to the second polynucleotide. In some embodiments, the method further includes cleaving the first quencher from the first nucleotide before coupling the polymerase to the first and second polynucleotides. In some embodiments, the method further includes adding the second nucleotide to the first polynucleotide after coupling the polymerase to the first and second polynucleotides. In some embodiments, the method further includes coupling a second quencher to the second nucleotide. In some embodiments, the second quencher is coupled to the second nucleotide after adding the second nucleotide to the first polynucleotide. In some embodiments, the second nucleotide is coupled to a first moiety, the second quencher is coupled to a second moiety, and said second quencher is coupled to the second nucleotide by coupling the second moiety to the first moiety. In some embodiments, the second quencher inhibits photon emission by a second chemiluminogenic molecule.

In some embodiments, the first quencher and the second quencher are the same type of quencher as one another. In one illustrative example, the first chemiluminogenic molecule and the second chemiluminogenic molecule are the same type of chemiluminogenic molecule as one another.

In some embodiments, the first quencher and the second quencher are different types of quenchers than one another. In one illustrative example, the first chemiluminogenic molecule and the second chemiluminogenic molecule are different types of chemiluminogenic molecules than one another.

In some embodiments, the first nucleotide is coupled to a third moiety, the first quencher is coupled to a fourth moiety, and said first quencher is coupled to the first nucleotide by coupling the fourth moiety to the third moiety. In one illustrative example, the first moiety and the third moiety are different than one another. In another illustrative example, the second moiety and the fourth moiety are different than one another.

In some embodiments, the method further includes detecting the photon emitted by the second chemiluminogenic molecule in the absence of the second quencher. In some embodiments, the method further includes detecting the presence of the second nucleotide based on inhibition of emission of the photon by the second chemiluminogenic molecule. In some embodiments, the method further includes detecting the photon emitted by the first chemiluminogenic molecule in the absence of the first quencher. In some embodiments, the method further includes detecting the presence of the first nucleotide based on detection of inhibition of emission of the photon by the first chemiluminogenic molecule. In some embodiments, the method further includes cleaving the first quencher from the first nucleotide.

In some embodiments, the first nucleotide is coupled to a first moiety, the first quencher is coupled to a second moiety, and said first quencher is coupled to the first nucleotide by coupling the first moiety to the second moiety. In one illustrative example, one of the first and second moieties is biotin or a biotin derivative, and the other of the first and second moieties is streptavidin. In another illustrative example, one of the first and second moieties is digoxigenin, and the other of the first and second moieties is anti-digoxigenin.

In some embodiments, the catalyst is coupled to the second polynucleotide. In some embodiments, the catalyst is coupled to the first polynucleotide. In some embodiments, the catalyst is coupled to the substrate.

In some embodiments, the catalyst includes an enzyme. In one illustrative example, the enzyme includes a luciferase, and the chemiluminogenic molecule includes a luciferin or a luciferin derivative. In another illustrative example, the enzyme includes a luciferase, and the chemiluminogenic molecule includes coelenterazine or a coelenterazine derivative. In yet another illustrative example, the enzyme includes a 1,2-dioxetane cleaver, and the chemiluminogenic molecule includes a 1,2-dioxetane derivative.

In some embodiments, the catalyst includes a peroxide generator, and the chemiluminogenic molecule includes luminol or a luminol derivative. In one illustrative example, the peroxide generator includes an enzyme. In another illustrative example, the peroxide generator includes a metallic, organic, or metalorganic catalyst.

In some embodiments, the catalyst includes a peroxide generator, and the chemiluminogenic molecule includes acridinium or an acridinium derivative. In one illustrative example, the peroxide generator includes an enzyme. In another illustrative example, the peroxide generator includes a metallic, organic, or metalorganic catalyst.

In some embodiments, the method further includes detecting the photon emitted by the first chemiluminogenic molecule. In some embodiments, the method further includes detecting the presence of the first nucleotide based on detection of the photon emitted by the first chemiluminogenic molecule.

Under another aspect, a method of sequencing a first polynucleotide includes providing the first polynucleotide to be sequenced and coupled to a substrate; hybridizing a second polynucleotide to the first polynucleotide; and providing a catalyst coupled sufficiently close to the second polynucleotide that a quencher coupled to the second polynucleotide can inhibit photon emission from chemiluminescent molecules that interact with the catalyst. The method further can include contacting the second polynucleotide with a polymerase and a plurality of nucleotides. A first subset of the plurality of nucleotides includes a first moiety, a second subset of the plurality of nucleotides includes a second moiety, a third subset of the plurality of nucleotides includes a third moiety, and a fourth subset of the plurality of nucleotides includes a fourth moiety or no moiety. The method further can include adding a nucleotide of the plurality of nucleotides to the second polynucleotide based on a sequence of the first polynucleotide. The method further can include exposing the nucleotide to a quencher coupled to a fifth moiety; exposing the nucleotide to chemiluminogenic molecules; and detecting emission of photons or an absence of photons from the chemiluminogenic molecules. The method further can include exposing the nucleotide to a quencher coupled to a sixth moiety; exposing the nucleotide to chemiluminogenic molecules; and detecting emission of photons or an absence of photons from the chemiluminogenic molecules. The method further can include exposing the nucleotide to a cleaver molecule; exposing the nucleotide to chemiluminogenic molecules; and detecting emission of photons or an absence of photons from the chemiluminogenic molecules. The method further can include detecting the added nucleotide based on the detection of emission of photons or absence of photons from the chemiluminogenic molecules at one or more of the detection steps or a combination thereof.

Under yet another aspect, a method of detecting nucleotides includes incorporating nucleotides into polynucleotides; performing at least one staining process including adding a catalyst or quencher to, or removing a catalyst or quencher from, at least one incorporated nucleotide; capturing at least first and second images in the presence of chemiluminogenic molecules; and performing nucleotide base calls based on at least the first and second images.

Under still another aspect, a method of detecting nucleotides includes incorporating fluorophore-labeled nucleotides into polynucleotides using catalyst-polymerase fusion protein; capturing at least one image in the presence of chemiluminogenic molecules; and performing nucleotide base calls based on the at least one image.

BRIEF DESCRIPTION OF DRAWINGS

In FIGS. 6A-6C, sequence is disclosed as SEQ ID NO: 2.

In FIGS. 8A-8E, sequence is disclosed as SEQ ID NO: 3, in FIGS. 8F-8H, sequence is disclosed as SEQ ID NO: 4, in FIGS. 8I-8L, sequence is disclosed as SEQ ID NO: 5, and in FIG. 8M, sequence is disclosed as SEQ ID NO: 6.

DETAILED DESCRIPTION

Figure 1A:
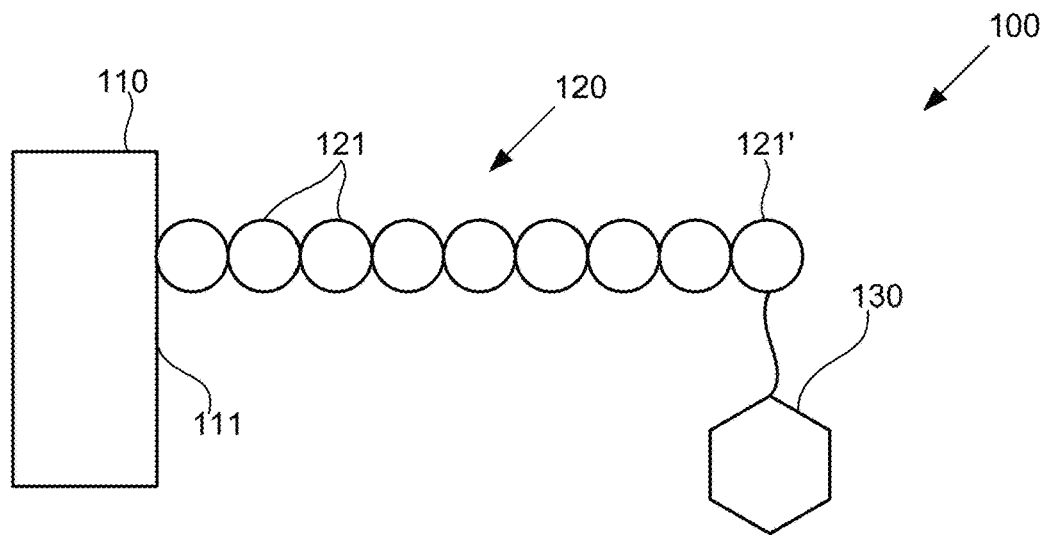
FIGS. 1A-1C schematically illustrate compositions for detecting the presence of polymer subunits using chemiluminescence, according to some embodiments of the present invention.

Embodiments of the present invention provide compositions, systems, and methods for detecting the presence of polymer subunits using chemiluminescence. More specifically, the present compositions, systems, and methods can be used to detect the presence, in a polymer including a plurality of subunits, of a selected subunit of that polymer. The selected subunit can be the terminal subunit of the polymer, or can be further along the polymer chain, e.g., a non-terminal subunit. The presence of such terminal or non-terminal subunit can be detected using a catalyst that is operable to cause a chemiluminogenic molecule to emit a photon.

In one example, the catalyst is coupled to the selected subunit, e.g., is coupled to the subunit before adding the subunit to the polymer, or is coupled to the subunit after adding the subunit to the polymer. The polymer, including the selected subunit having catalyst coupled thereto, is exposed to one or a plurality of the chemiluminogenic molecules, and optionally also to reagent molecule(s) that can facilitate reaction between the catalyst and the chemiluminogenic molecules. Responsive to the presence of the chemiluminogenic molecule(s) and the optional reagent molecule(s), the catalyst can cause those chemiluminogenic molecule(s) to emit respective photons. The presence of the selected subunit is detectable based on the detection of the photons. For example, the polymer can be coupled to a region of a substrate. The presence of the selected subunit in that polymer is detected based on detecting photons from that region of the substrate. Such detecting can be performed in parallel for multiple of the subunits of the polymer, e.g., by simultaneously detecting a plurality of the subunits. Alternatively, such detecting can be performed for a single subunit of the polymer at a given time. Such single-subunit detecting can be performed sequentially for different subunits of the polymer, thus permitting detection of the sequence of subunits of the polymer.

It will be appreciated that the presence of any suitable subunits of any suitable polymers can be detected based on chemiluminescence. In one illustrative example, the polymer includes a polynucleotide, and the subunits of the polymer include nucleotides of that polynucleotide. The sequence of the polynucleotide can be based on detecting the presence of each of the nucleotides. Such detecting can be performed in parallel, e.g., by simultaneously detecting a plurality of the nucleotides in the sequence. Alternatively, such detecting can be performed for a single nucleotide of the polynucleotide at a given time. For example, a polymerase can add a first nucleotide to the terminal end of a first polynucleotide based on the sequence of a second polynucleotide to which the first polynucleotide is hybridized. The first nucleotide can be coupled to a catalyst operable to cause a chemiluminogenic molecule to emit a photon. The catalyst can be coupled to the first nucleotide before the first nucleotide is added to the terminal end of the first polynucleotide, or after the first nucleotide is added to the terminal end of the polynucleotide. The first polynucleotide, of which the first nucleotide now defines the terminal end, can be exposed to the chemiluminogenic molecule(s), and optionally also to reagent molecule(s) that facilitate reaction between the catalyst and the chemiluminogenic molecule(s). Responsive to the presence of the chemiluminogenic molecule(s) and the optional reagent molecule(s), the catalyst can cause those chemiluminogenic molecule(s) to emit respective photons. The presence of the first nucleotide is detectable based on the detection of the photons.

For example, the first polynucleotide can be coupled to a region of a substrate; in one illustrative embodiment, the second polynucleotide is coupled to the region of the substrate, and the first polynucleotide is coupled to the region of the substrate by being hybridized to the second polynucleotide. The presence of the first nucleotide at the terminal end of the first polynucleotide is detected based on detecting photons from that region of the substrate. Such detecting can be performed in parallel for multiple of the nucleotides of the first polynucleotide, e.g., by simultaneously detecting a plurality of the nucleotides. Alternatively, such detecting can be performed for a single nucleotide of the first polynucleotide, e.g., the terminal nucleotide of the first polynucleotide, at a given time. In certain embodiments, nucleotides that are different than one another can be coupled to different catalysts than one another, or can include different moieties than one another that can selectively be coupled to or cleaved from one or more catalysts in such a manner as to permit distinguishing different types of nucleotides from one another as each nucleotide is added to the polynucleotide. Such single-nucleotide detecting can be performed sequentially for different nucleotides as they are added to the first polynucleotide, thus permitting detection of the sequence of nucleotides in the first polynucleotide, and accordingly permitting detection of the sequence of the second polynucleotide that is complementary to the sequence of the first polynucleotide.

It should be appreciated that the absence of emitted photons alternatively can be used to detect the presence of a polymer subunit. In one example, a catalyst operable to cause a chemiluminogenic molecule to emit a photon is provided, e.g., coupled to the polymer or to a substrate to which the polymer is coupled. A quencher operable to inhibit photon emission by the chemiluminogenic molecule is coupled to a selected subunit, e.g., is coupled to the subunit before adding the subunit to the polymer, or is coupled to the subunit after adding the subunit to the polymer. The polymer, including the selected subunit having the quencher coupled thereto, is exposed to one or a plurality of the chemiluminogenic molecules, and optionally also to reagent molecule(s) that can facilitate reaction between the catalyst and the chemiluminogenic molecules. Responsive to the presence of the chemiluminogenic molecule(s) and the optional reagent molecule(s), the quencher can inhibit emission of photons from the chemiluminogenic molecule(s) in the presence of the catalyst. The presence of the selected subunit is detectable based on the absence of the photons. For example, the polymer can be coupled to a region of a substrate. The presence of the selected subunit in that polymer is detected based on detecting the absence of photons from that region of the substrate. Such detecting can be performed in parallel for multiple of the subunits of the polymer, e.g., by simultaneously detecting a plurality of the subunits. Alternatively, such detecting can be performed for a single subunit of the polymer at a given time. Such single-subunit detecting can be performed sequentially for different subunits of the polymer, thus permitting detection of the sequence of subunits of the polymer.

It will be appreciated that the presence of any suitable subunits of any suitable polymers can be detected based on chemiluminescence. In one illustrative example, the polymer includes a polynucleotide, and the subunits of the polymer include nucleotides of that polynucleotide. A catalyst operable to cause a chemiluminogenic molecule to emit a photon is provided, e.g., coupled to the polynucleotide or to a substrate to which the polynucleotide is coupled. The sequence of the polynucleotide can be based on detecting the presence of each of the nucleotides. Such detecting can be performed in parallel, e.g., by simultaneously detecting a plurality of the nucleotides in the sequence. Alternatively, such detecting can be performed for a single nucleotide of the polynucleotide at a given time. For example, a polymerase can add a first nucleotide to the terminal end of a first polynucleotide based on the sequence of a second polynucleotide to which the first polynucleotide is hybridized. The first nucleotide can be coupled to a quencher operable to inhibit photon emission by the chemiluminogenic molecule. The catalyst can be coupled to the first nucleotide before the first nucleotide is added to the terminal end of the first polynucleotide, or after the first nucleotide is added to the terminal end of the polynucleotide. The first polynucleotide, of which the first nucleotide now defines the terminal end, can be exposed to the chemiluminogenic molecule(s), and optionally also to reagent molecule(s) that facilitate reaction between the catalyst and the chemiluminogenic molecule(s). In the absence of the quencher, in the presence of the chemiluminogenic molecule(s) and the optional reagent molecule(s), the catalyst can cause those chemiluminogenic molecule(s) to emit respective photons. However, the quencher attached to the first nucleotide can inhibit such photon emission. The presence of the first nucleotide is detectable based on the inhibition of the photon emission.

For example, the first polynucleotide can be coupled to a region of a substrate; in one illustrative embodiment, the second polynucleotide is coupled to the region of the substrate, and the first polynucleotide is coupled to the region of the substrate by being hybridized to the second polynucleotide. The presence of the first nucleotide at the terminal end of the first polynucleotide is detected based on detecting inhibition of photon emission from that region of the substrate. Such detecting can be performed in parallel for multiple of the nucleotides of the first polynucleotide, e.g., by simultaneously detecting a plurality of the nucleotides. Alternatively, such detecting can be performed for a single nucleotide of the first polynucleotide, e.g., the terminal nucleotide of the first polynucleotide, at a given time. In certain embodiments, nucleotides that are different than one another can be coupled to different quenchers than one another, or can include different moieties than one another that can selectively be coupled to or cleaved from one or more quenchers in such a manner as to permit distinguishing different types of nucleotides from one another as each nucleotide is added to the polynucleotide. Such single-nucleotide detecting can be performed sequentially for different nucleotides as they are added to the first polynucleotide, thus permitting detection of the sequence of nucleotides in the first polynucleotide, and accordingly permitting detection of the sequence of the second polynucleotide that is complementary to the sequence of the first polynucleotide.

First, some terms used herein will be briefly explained. Then, some exemplary compositions, exemplary systems including measurement circuitry that can be used with the present compositions, exemplary methods that can be used with the present compositions, some specific examples of compositions that can be used during such methods, and exemplary results, will be described.

Exemplary Terms

As used herein, "polymer" means a molecule including a plurality of repeated subunits. Polymers can be biological or synthetic polymers. Exemplary biological polymers include polynucleotides (an exemplary subunit of which is a nucleotide), polypeptides (an exemplary subunit of which is an amino acid), polysaccharides (an exemplary subunit of which is a sugar), polynucleotide analogs (an exemplary subunit of which is a nucleotide analog), and polypeptide analogs (an exemplary subunit of which is an amino acid analog). Exemplary polynucleotides and polynucleotide analogs include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. Exemplary synthetic polymers include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(ω-alkenoic acid esters), poly(alkyl methacrylates), and other polymeric chemical and biological linkers such as disclosed in Hermanson, *Bioconjugate Techniques*, third edition, Academic Press, London (2013).

As used herein, the term "nucleotide" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), deoxyuridine triphosphate (dUTP), reversibly blocked adenosine triphosphate (rbATP), reversibly blocked thymidine triphosphate (rbTTP), reversibly blocked cytidine triphosphate (rbCTP), and reversibly blocked guanosine triphosphate (rbGTP). For further details on reversibly blocked nucleotide triphosphates (rbNTPs), see U.S. Patent Publication No. 2013/0079232, the entire contents of which are incorporated by reference herein.

The term "nucleotide" also is intended to encompass any nucleotide analogue which is a type of nucleotide that includes a modified nucleobase, sugar and/or phosphate moiety. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a "substrate" is intended to mean a structure formed of a solid material that is relatively large as compared to one or more molecules that can be coupled thereto. Substrates can include biological or solid state materials, or a combination thereof. Exemplary solid-state substrates can include one or more insulators such as glass or plastic, one or more conductors such as metals or conductive polymers, and one or more semiconductor materials, such as silicon or germanium, or any suitable combination of insulator(s), conductor(s), and semiconductor(s). A substrate can be, but need not necessarily be, included in a flowcell or array type of platform.

As used herein, "coupled" is intended to mean an attachment between a first member and a second member that is sufficiently stable as to be useful for detecting a subunit of a polymer. In some embodiments, such an attachment is normally irreversible under the conditions in which the attached members are used. In other embodiments, such a permanent attachment is reversible but persists for at least the period of time in which it is used for detecting a subunit of a polymer. Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can used to couple a first member to a second member. Other examples include duplexes between oligonucleotides, peptide-peptide interactions, and hapten-antibody interactions such as streptavidin-biotin, streptavidin-desthiobiotin, and digoxigenin-anti-digoxigenin. In one embodiment, an attachment can be formed by hybridizing a first polynucleotide to a second polynucleotide that inhibits detachment of the first polynucleotide from the second polynucleotide. Alternatively, an attachment can be formed using physical or biological interactions, e.g., an interaction between a first protein and a second protein that inhibits detachment of the first protein from the second protein.

As used herein, a "catalyst" is a molecule that participates in a chemical reaction, but is not consumed in that reaction. Catalysts include enzymes, metallic, organic, and metalorganic catalysts as well as auto-catalytic compounds. As used herein, the term "enzyme" is intended to mean a biomolecule that catalytically modifies another molecule. Enzymes can include proteins, as well as certain other types of molecules such as polynucleotides. As used herein, the term "protein" is intended to mean a molecule that includes, or consists of, a polypeptide that is folded into a three-dimensional structure. The polypeptide includes moieties that, when folded into the three-dimensional structure, impart the protein with biological activity.

As used herein, "chemiluminescence" means light resulting from a chemical reaction in which one or more reagents of the reaction undergo a chemical change. The term "chemiluminescence" is intended to encompass bioluminescence, e.g., light resulting from biological reactions, as well as light resulting from other types of reactions.

As used herein, a "chemiluminogenic molecule" is a molecule that chemiluminesces when reacted with appropriate reagents.

As used herein, "hybridize" is intended to mean noncovalently binding a first polynucleotide to a second polynucleotide. The strength of the binding between the first and second polynucleotides increases with the complementarity between those polynucleotides.

As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

Exemplary Compositions and Methods

Some exemplary compositions and methods for detecting the presence of polymer subunits using chemiluminescence now will be described with reference to FIGS. 1A-1C and 2-4.

Figure 1B:
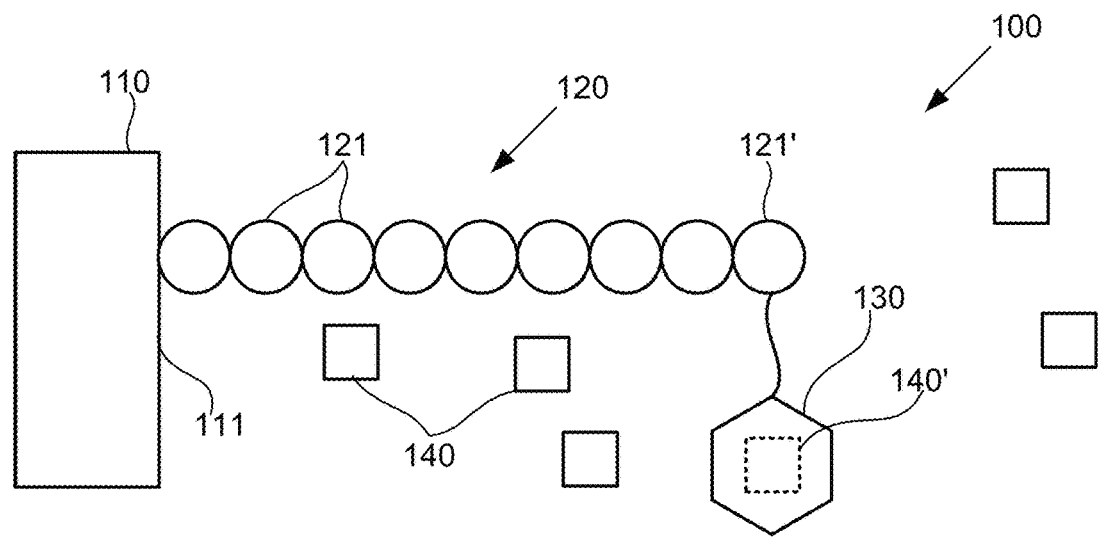
Figure 1C:
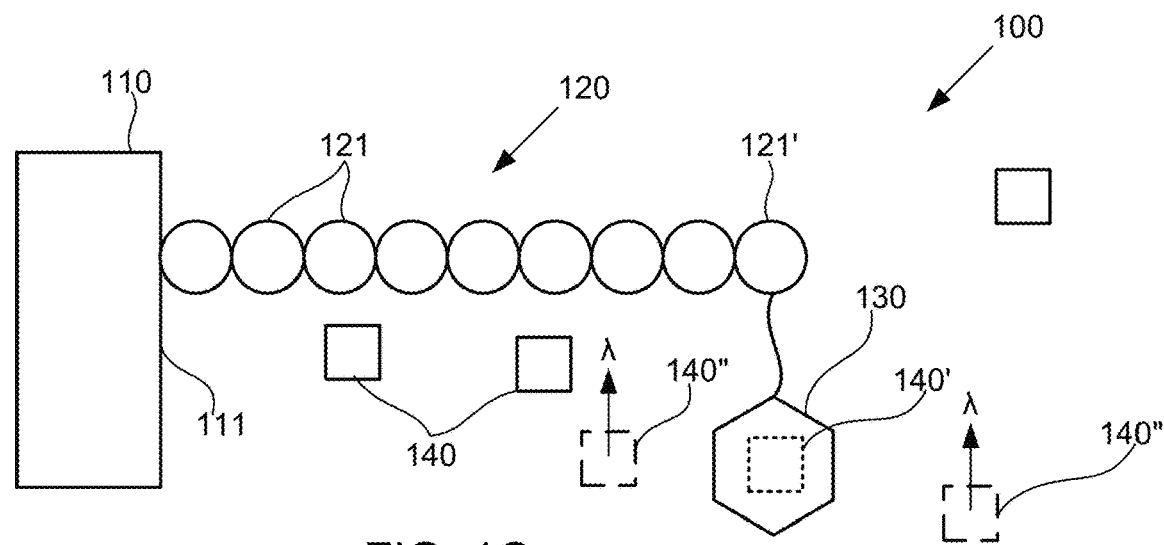

Under one aspect, a composition includes a polymer including a plurality of subunits, and a catalyst coupled to a first subunit of the polymer. The catalyst is operable to cause a chemiluminogenic molecule to emit a photon. For example, FIGS. 1A-1C schematically illustrate compositions for detecting the presence of polymer subunits using chemiluminescence, according to some embodiments of the present invention. Exemplary composition 100 illustrated in FIG. 1A includes substrate 110, polymer 120 including a plurality of subunits 121, and catalyst 130 coupled to a selected subunit 121' of the subunits 121. In the illustrated embodiment, substrate 110 includes surface 111 to which polymer 120 is coupled. However, it should be understood that polymer 120 need not necessarily be coupled to substrate 110, and that substrate 110 is optional. In embodiments that include substrate 110, the substrate optionally includes an optical detector (not specifically illustrated) operable to detect one or more photons emitted by chemiluminogenic molecule(s) responsive to the presence of catalyst 130 and selected polymer subunit 121' to which catalyst 130 is coupled. One exemplary optical detector is an active-pixel sensor including an array of amplified photodetectors configured to generate an electrical signal based on photons received by the photodetectors.

Substrate 110 can include biological or solid state materials, or a combination thereof. Exemplary solid-state substrates can include one or more insulators such as glass or plastic, one or more conductors such as metals or conductive polymers, and one or more semiconductor materials, such as silicon or germanium, or any suitable combination of insulator(s), conductor(s), and semiconductor(s). A semiconductor based substrate can be referred to as a "chip." In some embodiments, the substrate can include an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of both of which are incorporated herein in their entirety by reference. Possible substrates include, but are not limited to, glass and modified or functionalized glass, plastics (including acrylics, polystyrene and copolymers of styrene and other materials, polypropylene, polyethylene, polybutylene, polyurethanes, Teflon™, and the like), polysaccharides, nylon or nitrocellulose, ceramics, resins, silica or silica-based materials including silicon and modified silicon, carbon, metals, inorganic glasses, plastics, optical fiber bundles, and a variety of other polymers.

In some embodiments, the substrate or its surface is non-planar, such as the inner or outer surface of a tube or vessel. In some embodiments, the substrate includes a microsphere or a bead. By "microsphere" or "bead" or "particle" or grammatical equivalents herein is meant a relatively small discrete particle. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for substrates may all be used. "Microsphere Detection Guide" from Bangs Laboratories, Fishers Ind. is a helpful guide. In certain embodiments, the microspheres are magnetic microspheres or beads. Note that the beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

Substrate 110 can be, but need not necessarily be, included in a flowcell or array type of platform. In one illustrative embodiment in which polymer 120 is a polynucleotide, the platform can be configured for parallel sequencing of multiple polynucleotides. Platforms configured for parallel sequencing of multiple polynucleotides include, but are not limited to, those offered by Illumina, Inc. (e.g., HiSeq, Genome Analyzer, MiSeq, iScan platforms), Life Technologies (e.g., SOLiD), Helicos Biosciences (e.g., Heliscope), 454/Roche Life Sciences (Branford, Conn.) and Pacific Biosciences (e.g., SMART). Flowcells, chips, and other types of surfaces that may accommodate multiple nucleic acid species are exemplary of substrates utilized for parallel sequencing. In multiplex formats wherein multiple nucleic acid species are sequenced in parallel, clonally amplified target sequences (e.g., via emulsion PCR (emPCR) or bridge amplification) are typically covalently immobilized on a substrate. For example, when practicing emulsion PCR, the target of interest is immobilized on a bead substrate, whereas clonally amplified targets are immobilized in channels of a flowcell based substrate or specific locations on an array based or chip based substrate.

In one illustrative embodiment, substrate 110 can include a CMOS chip that has been adapted for sequencing applications. Surface 111 of substrate 110 can include one or more hydrophilic regions for polymer attachment, e.g., polynucleotide attachment, and amplification surrounded by hydrophobic regions. For example, dynamic pads having a hydrophilic patch can be used, such as described in US 2013/0116128, the entire contents of which are incorporated by reference herein. Alternatively or additionally, a collection of dynamic pads including some that are in a hydrophilic state while surrounding pads are in a hydrophobic state can form hydrophilic regions surrounded by a hydrophobic region. The surface for polymer attachment, e.g., nucleic acid attachment, optionally can include a plurality of isolated regions such that each isolated region contains a plurality of nucleic acid molecules that can be derived from one nucleic acid molecule for sequencing. For example, the hydrophilic region can include a gel. The hydrophilic regions could be smooth, textured, porous, or non-porous, for example. The hydrophobic regions can be located between the hydrophilic regions. Molecules can be moved across the surface by way of any number of forces, e.g., electrowetting forces, such as described in US 2013/0116128.

In the illustrated embodiment, polymer 120 is coupled to surface 111 of substrate 110 using any suitable permanent attachment. Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can used to couple polymer 120 to surface 111 of substrate 110. Other examples include duplexes between oligonucleotides, peptide-peptide interactions, and hapten-antibody interactions such as streptavidin-biotin, streptavidin-desthiobiotin, and digoxigenin-anti-digoxigenin. In an exemplary embodiment in which polymer 120 is a polynucleotide, that polynucleotide can be attached to surface 111 of substrate 110 by hybridizing that polynucleotide to another polynucleotide that is coupled to surface 111. Alternatively, an attachment can be formed using physical or biological interactions, e.g., an interaction between a first protein coupled to polymer 120 and a second protein coupled to substrate 110 that inhibits detachment of the first protein from the second protein.

Polymer 120 can include a biological polymer or a synthetic polymer. Exemplary biological polymers include polynucleotides (an exemplary subunit of which is a nucleotide), polypeptides (an exemplary subunit of which is an amino acid), polysaccharides (an exemplary subunit of which is a sugar), polynucleotide analogs (an exemplary subunit of which is a nucleotide analog), and polypeptide analogs (an exemplary subunit of which is an amino acid analog). Exemplary polynucleotides and polynucleotide analogs include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. Exemplary synthetic polymers include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(w-alkenoic acid esters), poly(alkyl methacrylates), and other polymeric chemical and biological linkers such as disclosed in Hermanson, *Bioconjugate Techniques*, third edition, Academic Press, London (2013). In one illustrative and nonlimiting embodiment, polymer 120 includes a polynucleotide, and subunits 121 thereof include nucleotides.

Catalyst 130 is operable to cause a chemiluminogenic molecule to emit a photon, and is coupled to a selected subunit 121' of the subunits 121. In the illustrated embodiment, catalyst 130 is coupled to selected subunit 121' using any suitable permanent attachment. Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can used to couple catalyst 130 to selected subunit 121'. For example, catalyst 130 can be coupled to selected subunit 121' via a first moiety coupled to subunit 121' and a second moiety coupled to the first moiety and to catalyst 130. The first and second moieties can include oligonucleotides, peptides, or binding pairs such as hapten-antibody pairs such as streptavidin-biotin, streptavidin-desthiobiotin, and digoxigenin-anti-digoxigenin. For example, one of the first and second moieties can be biotin or a biotin derivative, and the other of the first and second moieties can be streptavidin. Or, for example, one of the first and second moieties can be digoxigenin, and the other of the first and second moieties is anti-digoxigenin. Or, for example, an attachment can be formed using physical or biological interactions, e.g., an interaction between a protein, hapten, or antibody coupled to selected subunit 121' and a protein, hapten, or antibody coupled to catalyst 130 that inhibits detachment of catalyst 130 from selected subunit 121'. In some embodiments, catalyst 130 also can be cleavable from the selected subunit 121', e.g., by exposing catalyst 130 and selected subunit 121' to one or more suitable reagent molecules for cleaving the coupling between catalyst 130 and subunit 121' after detecting the presence of selected subunit 121'.

Catalyst 130 can include, for example, an enzyme or a metallic, organic, or metalorganic catalyst or auto-catalytic compound operable to cause a chemiluminogenic molecule to emit a photon. Exemplary catalysts operable to cause a chemiluminogenic molecule to emit a photon are disclosed in Dodeigne et al., "Chemiluminescence as diagnostic tool. A review," Talanta 51: 415-439 (2000), the entire contents of which are incorporated by reference herein. As one example, the catalyst can include a peroxide generator, such as an enzyme or a metallic, organic, or metalorganic catalyst, and the chemiluminogenic molecule can include luminol or a luminol derivative. As another example, the catalyst can include a peroxide generator, such as an enzyme or a metallic, organic, or metalorganic catalyst, and the chemiluminogenic molecule can include acridinium or an acridinium derivative. A wide variety of peroxide generators that can be suitable for use in causing luminol, a luminol derivative, acridinium, or acridinium derivative to chemiluminescence are known in the art, such as those disclosed in Dodeigne, including microperoxidase, myeloperoxidase, horseradish peroxidase (HRP), bacterial peroxidase (e.g., from *Arthromyces ramosus*), catalase, xanthine oxidase, alkaline phosphatase, β-D-galactosidase and β-glucosidase in the presence of indoxyl conjugates, lactate oxidase, acylCoA synthetase, acylCoA oxidase, diamine oxidase, cytochrome c, hemoglobin, haptoglobin, deuterohemin, molecular ozone, halogens, persulfate anions, Fe(III), Co(II), Cu(II) complexes. Additionally, as disclosed in Dodeigne, 3-α hydroxysteroid deshydrogenase or glucose-6-phosphate deshydrogenase release NADH which reduces molecular oxygen to hydrogen peroxide in the presence of 1-methoxy-5-methylphenazinium methylsulphate. Exemplary luminol derivatives include isoluminol, aminoethylisoluminol (AEI), aminoethylethylisoluminol (AEEI), aminobutylisoluminol (ABI), aminobutylethylisoluminol (ABEI), aminopentylethylisoluminol (APEI), aminohexylisoluminol (AHI), aminohexylethylisoluminol (AHEI), aminooctylmethylisoluminol (AOMI), aminooctylethylisoluminol (AOEI), and aminobutylethynaphthalhydrazide (ABENH), such as disclosed in Dodeigne. Exemplary acridinium derivatives include lucigenin, arylmethylene N-methyl dihydroacridines, un-substituted N-methyl acridine, and N-methyl acridines substituted with alcohols, fluoroalcohols, phenols, thiols, sulphonamides, heterocyclic amines, heterocyclic endocyclic amines, hydroxamic acids, sulphohydroxamic acids, thiolamines, oximes (e.g., O-esterified oximes), or chroloxime leaving groups, e.g., methoxy substituted N-methyl acridine, 4-(2-succinimidyl-oxycarbonylethyl)-phenyl-10-methyl-acridinium-9-carboxylate (AE-NHS), and the 2-6-dimethyl phenol analog of AE-NHS, such as disclosed in Dodeigne.

As another example, the catalyst can include an enzyme such as a luciferase, and the chemiluminogenic molecule can include a luciferin or a luciferin derivative. As yet another example, the catalyst can include an enzyme such as a luciferase, and the chemiluminogenic molecule can include colenterazine or a colenterazine derivative. "Luciferase" refers to a class of oxidative enzymes that catalytically facilitate chemiluminescence and that include firefly luciferase from the species *Photinus pyralis* or another firefly species, bacterial luciferase monooxygenase, *Renilla*-luciferin 2-monooxygenase, dinoflagellate luciferase, lumazine protein such as in *Vibrio fischeri, haweyi*, and *harveyi*, *Metridia* luciferase derived from *Metridia longa*, and *Vargula* luciferase. Luciferins and luciferin derivatives are exemplary chemiluminogenic molecules that can emit photons responsive to interactions with a luciferase in the presence of an oxygen-containing reagent molecule. Exemplary luciferins include colenterazine (also referred to as *Renilla* luciferin), colenterazine derivatives, firefly luciferin, *Latia* luciferin, bacterial luciferin, dinoflagellate luciferin, and vargulin. Exemplary colenterazine derivatives include 2-methyl-6-phenyl-3,7-dihydroimidazo[1,2-a]pyrazin-3-one (CLA) and 2-methyl-6-(4-methoxyphenyl)-3,7-dihydroimidazo[1,2-a]pyrazin-3-one (CLA) and other derivatives such as disclosed in Dodeigne.

As another example, the catalyst can include an enzyme such as a 1,2-dioxetane cleaver, and the chemiluminogenic molecule can include a 1,2-dioxetane derivative. Exemplary 1,2-dioxetane cleavers and 1,2-dioxetane derivatives suitable for use therewith are disclosed in U.S. Pat. No. 5,330,900 to Bronstein et al., the entire contents of which are incorporated by reference herein. Exemplary 1,2-dioxetane cleavers include acid phosphatase, alkaline phosphatase, β-D-galactosidase, such as disclosed in Bronstein. Exemplary 1,2-dioxetane derivatives include 3-3,4-trimethyl-1,2-dioxetane, adamantylidene adamantyl 1,2-dioxetane, 9-(2-adamantylidene)-N-methylacridan-1,2-dioxetane, phenol substituted 1,2-dioxetane, silylated or esterified phenol substituted 1,2-dioxetane, 3-(2'-spiroadamantane)-4-methoxy-4-(3"-phosphoryloxy)phenyl-1,2-dioxetane disodium salt (AMPPD), 3-(2'-spiroadamantane)-4-methoxy-4-(3"-β-D-galactopyranosyloxyphenyl)-1,2-dioxetane (AMPGD), 3-4-methoxyspiro(1,2-dioxetane-3,2'-(5'-chloro)tricyclo-[3.3.1.1.3,7]decan)-4-yl phenyl-phosphate disodium salt (CSPD), and other derivatives such as disclosed in Dodeigne or in Bronstein.

It should be appreciated that other pairs or combinations of catalysts and chemiluminogenic molecules suitably can be used in the present compositions, systems, and methods, and that the examples provided above are intended to be purely illustrative and not limiting in any way.

As illustrated in FIG. 1B, composition 100 further can include, or can be contacted with a plurality of chemiluminogenic molecules 140 that respectively emit photons responsive to interactions with catalyst 130. For example, catalyst 130 can bind or otherwise suitably interact with a selected chemiluminogenic molecule 140', which causes that chemiluminogenic molecule to have an excited state, as represented by the dotted lines of molecule 140' in FIG. 1B. Optionally, composition 100 further includes, or further is contacted with, one or more reagent molecule(s) (not specifically illustrated) that can facilitate interaction between catalyst 130 and chemiluminogenic molecules 140 so as to cause the chemiluminogenic molecules to emit respective photons. As illustrated in FIG. 1C, after interaction with catalyst 130 and optional reagent molecule(s) causes chemiluminogenic molecules 140 to obtain an excited state 140', such excited states can decay by emitting a corresponding photon, as represented in FIG. 1C by the dashed lines of molecule 140" and arrow with "λ" representing photon emission. Based on the photon emission, the presence of subunit 121' can be detected, e.g., using suitable circuitry configured to detect the photon such as described further below with reference to FIGS. 10A-10B and 11A-11B. In some embodiments, catalyst 130 interacts with a plurality of chemiluminogenic molecules 140, thus causing the emission of a corresponding plurality of photons, thus increasing the detectability of subunit 121', such as described further below with reference to FIG. 12.

In one illustrative example, catalyst 130 can include a peroxide generator and chemiluminogenic molecules 140 can include luminol or a luminol derivative, and the reagent molecules can include oxygen containing molecules that the peroxide generator can use to oxidize the luminol or luminol derivative so as to form an intermediate molecule having an excited state, e.g., as represented by the dotted lines of molecule 140' in FIG. 1B, that then decays by emitting a photon, e.g., as represented by the dashed lines of molecule 140" in FIG. 1C. Or, for example, catalyst 130 can include a peroxide generator and chemiluminogenic molecules 140 can include acridinium or an acridinium derivative, and the reagent molecules can include oxygen containing molecules that the peroxide generator can use to oxidize the acridinium or acridinium derivative so as to form an intermediate molecule having an excited state, e.g., as represented by the dotted lines of molecule 140' in FIG. 1B, that then decays by emitting a photon, e.g., as represented by the dashed lines of molecule 140" in FIG. 1C. In another example, catalyst 130 can include a luciferase and chemiluminogenic molecules 140 can include a luciferin or a luciferin derivative, and the reagent molecules can include ATP and $O_2$ that the luciferase can use to interact with the luciferin or luciferin derivative so as to form an intermediate molecule having an excited state, e.g., as represented by the dotted lines of molecule 140' in FIG. 1B, that then decays by emitting a photon, e.g., as represented by the dashed lines of molecule 140" in FIG. 1C. In another example, catalyst 130 can include a luciferase and chemiluminogenic molecules 140 can include a luciferin or a luciferin derivative, and the reagent molecules can include ATP and $O_2$ that the luciferase can use to interact with the luciferin or luciferin derivative so as to form an intermediate molecule having an excited state, e.g., as represented by the dotted lines of molecule 140' in FIG. 1B, that then decays by emitting a photon, e.g., as represented by the dashed lines of molecule 140" in FIG. 1C. In another example, catalyst 130 can include a 1,2-dioxetane cleaver and chemiluminogenic molecules 140 can include a 1,2-dioxetane derivative; in such embodiments, reagent molecules need not necessarily be needed for catalyst 130 to form an intermediate molecule having an excited state, e.g., as represented by the dotted lines of molecule 140' in FIG. 1B, that then decays by emitting a photon, e.g., as represented by the dashed lines of molecule 140" in FIG. 1C.

Figure 2:
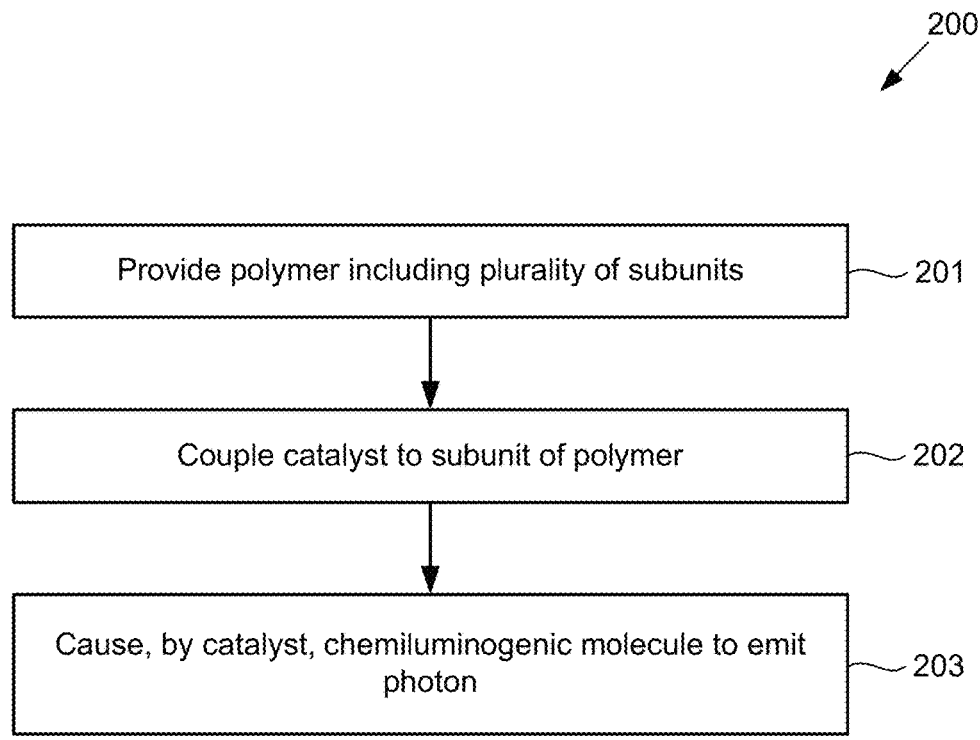
FIG. 2 illustrates a method for detecting the presence of polymer subunits using chemiluminescence, according to some embodiments of the present invention.

FIG. 2 illustrates a method for detecting the presence of polymer subunits using chemiluminescence, according to some embodiments of the present invention. Method 200 illustrated in FIG. 2 includes providing a polymer including a plurality of subunits (201). For example, polymer 120 illustrated in FIGS. 1A-1C can be provided, and optionally can be coupled to a substrate such as substrate 110. Method 200 illustrated in FIG. 2 also includes coupling a catalyst to a subunit of the polymer (202). For example, catalyst 130 illustrated in FIGS. 1A-1C can be coupled to subunit 121' of polymer 120 using any suitable linkage. Method 200 illustrated in FIG. 2 also includes causing, by the catalyst, a chemiluminogenic molecule to emit a photon (203). For example, catalyst 130 illustrated in FIGS. 1A-1C can bind or otherwise suitably interact with a selected chemiluminogenic molecule 140' of a plurality of chemiluminogenic molecules 140, which causes that chemiluminogenic molecule to have an excited state, as represented by the dotted lines of molecule 140' in FIG. 1B. Optionally, one or more reagent molecule(s) (not specifically illustrated) also can be provided that can facilitate interaction between catalyst 130 and chemiluminogenic molecules 140 so as to cause the chemiluminogenic molecules to emit respective photons. As illustrated in FIG. 1C, after interaction with catalyst 130 and optional reagent molecule(s) causes chemiluminogenic molecules 140 to obtain an excited state 140', such excited states can decay by emitting a corresponding photon, as represented in FIG. 1C by the dashed lines of molecule 140" and arrow with "λ" representing photon emission. Based on the photon emission, the presence of subunit 121' can be detected, e.g., using suitable circuitry configured to detect the photon such as described further below with reference to FIGS. 10A-10B and 11A-11B. In some embodiments, catalyst 130 interacts with a plurality of chemiluminogenic molecules 140, thus causing the emission of a corresponding plurality of photons, thus increasing the detectability of subunit 121', such as described further below with reference to FIG. 12.

In alternative embodiments, the presence of a polymer subunit can be detected based on inhibition of chemiluminescence. Under one aspect, a composition can include a catalyst operable to cause a chemiluminogenic molecule to emit a photon, a polymer including a plurality of subunits, and a quencher coupled to a first subunit of the polymer. The quencher can be operable to inhibit photon emission by the chemiluminogenic molecule. For example, FIG. 3 schematically illustrates an alternative compositions for detecting the presence of polymer subunits using chemiluminescence, according to some embodiments of the present invention.

Figure 3:
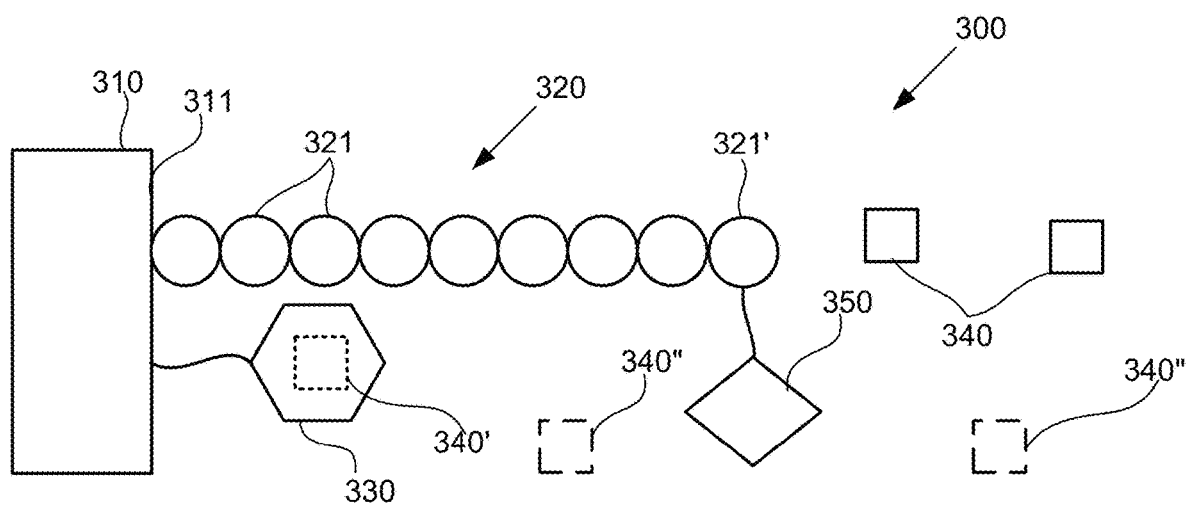
FIG. 3 schematically illustrates an alternative composition for detecting the presence of polymer subunits using chemiluminescence, according to some embodiments of the present invention.

Exemplary composition 300 illustrated in FIG. 3 includes substrate 310, polymer 320 including a plurality of subunits 321, catalyst 330 operable to cause a chemiluminogenic molecule 340 to emit a photon, and quencher 350. Exemplary polymers, substrates, catalysts, couplings, chemiluminogenic molecules, reagent molecules, chemiluminogenic reactions, and detection circuitry suitable for use with are described elsewhere herein, e.g., with reference to FIGS. 1A-1C. In the illustrated embodiment, substrate 310 includes surface 311 to which polymer 320 and catalyst 330 each are coupled via any suitable permanent attachment, although it should be appreciated that catalyst 330 suitably can be coupled anywhere in the region of polymer 320. Quencher 350 is coupled to a selected subunit 321' of the subunits 321 using any suitable permanent attachment. Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can used to couple quencher 350 to selected subunit 321'. For example, quencher 350 can be coupled to selected subunit 321' via a first moiety coupled to subunit 321' and a second moiety coupled to the first moiety and to catalyst 330. The first and second moieties can include oligonucleotides, peptides, or binding pairs such as hapten-antibody pairs such as streptavidin-biotin, streptavidin-desthiobiotin, and digoxigenin-anti-digoxigenin. For example, one of the first and second moieties can be biotin or a biotin derivative, and the other of the first and second moieties can be streptavidin. Or, for example, one of the first and second moieties can be digoxigenin, and the other of the first and second moieties is anti-digoxigenin. Or, for example, an attachment can be formed using physical or biological interactions, e.g., an interaction between a protein, hapten, or antibody coupled to selected subunit 321' and a protein, hapten, or antibody coupled to quencher 350 that inhibits detachment of quencher 350 from selected subunit 321'. In some embodiments, quencher 350 also can be cleavable from the selected subunit 321', e.g., by exposing quencher 350 and selected subunit 321' to one or more suitable reagent molecules for cleaving the coupling between quencher 350 and subunit 321' after detecting the presence of selected subunit 321'.

Quencher 350 can include any suitable quencher. Exemplary quenchers known in the art include the DABCYL Quencher, BHQ-1® Quencher, BHQ-2® Quencher, BHQ-3® Quencher, and ECLIPSE Quencher, each of which is commercially available from Jena Bioscience GmbH, Jena, Germany; BHQ-0 Dark Quencher available from Biosearch Technologies, Inc., Petaluma, Calif.; ELLEQUENCHER™ (Eurogentec S.A., Maastrict, The Netherlands); IOWA BLACK® Quencher available from Integrated DNA Technologies, Inc., Coralville, Iowa; (±)-6-hydroxy-2,5,7,8-tetramethylchromane-2-carboxylic acid (trade name Trolox) available from Sigma-Aldrich Co., LLC, St. Louis, Mo.; QSY 7, QSY 9, QSY 21, and QSY 35 quenchers, each of which is commercially available from Life Technologies, Grand Island, N.Y.; and dinitrophenol (DNP) quenchers such as 2,4-dinitrophenol (2,4-DNP), 2,5-dinitrophenol (2,5-DNP), and 2,6-dinitrophenol (2,6-DNP).

As illustrated in FIG. 3, composition 300 further can include, or can be contacted with, a plurality of chemiluminogenic molecules 340 that respectively emit photons responsive to interactions with catalyst 330 in the absence of quencher 350. For example, catalyst 330 can bind or otherwise suitably interact with a selected chemiluminogenic molecule 340', which causes that chemiluminogenic molecule to have an excited state, as represented by the dotted lines of molecule 340' in FIG. 3. Optionally, composition 300 further includes, or further is contacted with, one or more reagent molecule(s) (not specifically illustrated) that can facilitate interaction between catalyst 330 and chemiluminogenic molecules 340 so as to cause the chemiluminogenic molecules to emit respective photons in the absence of quencher 350. As illustrated in FIG. 3, interaction with catalyst 330 and optional reagent molecule(s) causes chemiluminogenic molecules 340 to obtain an excited state 340'. However, whereas such excited states can decay by emitting a corresponding photon in the absence of quencher 350 in a manner analogous to that described above with reference to FIGS. 1A-1C, in the embodiment illustrated in FIG. 3, quencher 350 inhibits photon emission from excited state molecules 340' such that excited state molecules 340' decay to ground state molecules 340" with reduced or no photon emission. Based on the inhibited photon emission, the presence of subunit 321' can be detected, e.g., using suitable circuitry configured to detect the photon such as described further below with reference to FIGS. 10A-10B and 11A-11B. For example, a respective amount of photon emission from composition 300 in the presence of chemiluminogenic molecules 340 can be detected before and after coupling quencher 350 to subunit 321', and based on reduced photon emission after coupling quencher 350 to subunit 321' it can be detected that subunit 321' is present. In some embodiments, catalyst 330 interacts with a plurality of chemiluminogenic molecules 340, thus causing the emission of a corresponding plurality of photons in the absence of quencher 350, thus increasing the detectability of subunit 321', such as described further below with reference to FIG. 12.

Figure 4:
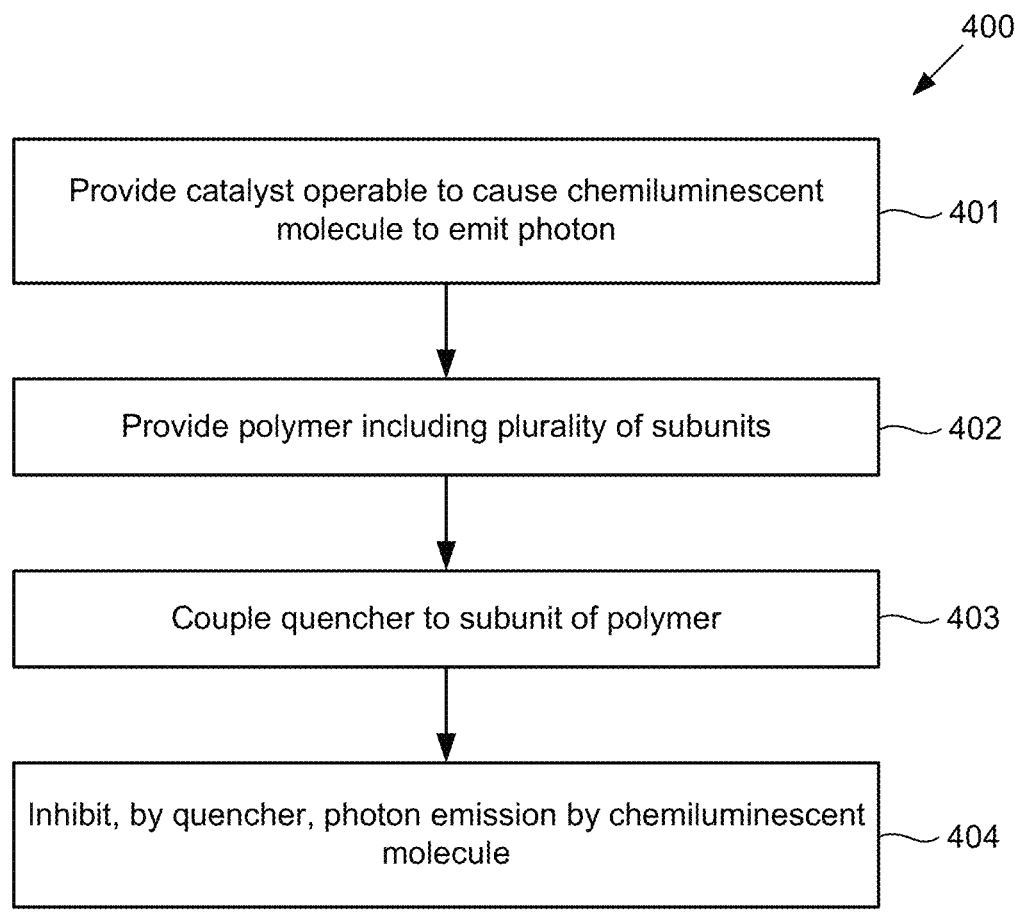
FIG. 4 illustrates an alternative method for detecting the presence of polymer subunits using chemiluminescence, according to some embodiments of the present invention.

FIG. 4 illustrates an alternative method for detecting the presence of polymer subunits using chemiluminescence, according to some embodiments of the present invention. Method 400 illustrated in FIG. 4 includes providing a catalyst operable to cause a chemiluminogenic molecule to emit a photon (401). For example, catalyst 330 illustrated in FIG. 3 can be coupled to surface 311 of substrate 310, or otherwise in substantially fixed relation to polymer 320, using any suitable linkage. Method 400 illustrated in FIG. 4 further includes providing a polymer including a plurality of subunits (402). For example, polymer 320 illustrated in FIG. 3 can be provided, and can be coupled to a substrate such as substrate 310. Method 400 illustrated in FIG. 4 further includes coupling a quencher to a first subunit of the polymer (403). For example, quencher 350 illustrated in FIG. 3 can be coupled to subunit 321' of polymer 320 using any suitable linkage. Method 400 illustrated in FIG. 4 also includes inhibiting, by the quencher, photon emission by the chemiluminogenic molecule (404). For example, catalyst 330 illustrated in FIG. 3 can bind or otherwise suitably interact with a selected chemiluminogenic molecule 340' of a plurality of chemiluminogenic molecules 340, which causes that chemiluminogenic molecule to have an excited state, as represented by the dotted lines of molecule 340' in FIG. 3. Optionally, one or more reagent molecule(s) (not specifically illustrated) also can be provided that can facilitate interaction between catalyst 330 and chemiluminogenic molecules 340 that would cause the chemiluminogenic molecules to emit respective photons in the absence of quencher 350. As illustrated in FIG. 3, although interaction with catalyst 330 and optional reagent molecule(s) causes chemiluminogenic molecules 340 to obtain an excited state 340', quencher 350 inhibits such excited states from emitting a corresponding photon, and instead causes the excited state molecule to decay without photon emission, as represented in FIG. 3 by the dashed lines of molecule 340". Based on the inhibited photon emission, the presence of subunit 321' can be detected, e.g., using suitable circuitry configured to detect the inhibition of photons such as described further below with reference to FIGS. 10A-10B and 11A-11B.

Sequencing by Synthesis Using Exemplary Methods and Exemplary Compositions for Use During Such Methods As noted further above, one exemplary polymer that can be used in the present methods and compositions is a polynucleotide. Detection of the nucleotides of that polynucleotide can be used to sequence the polynucleotide—as well as another polynucleotide to which that nucleotide is hybridized—using "sequencing by synthesis," or SBS.

Figure 5:
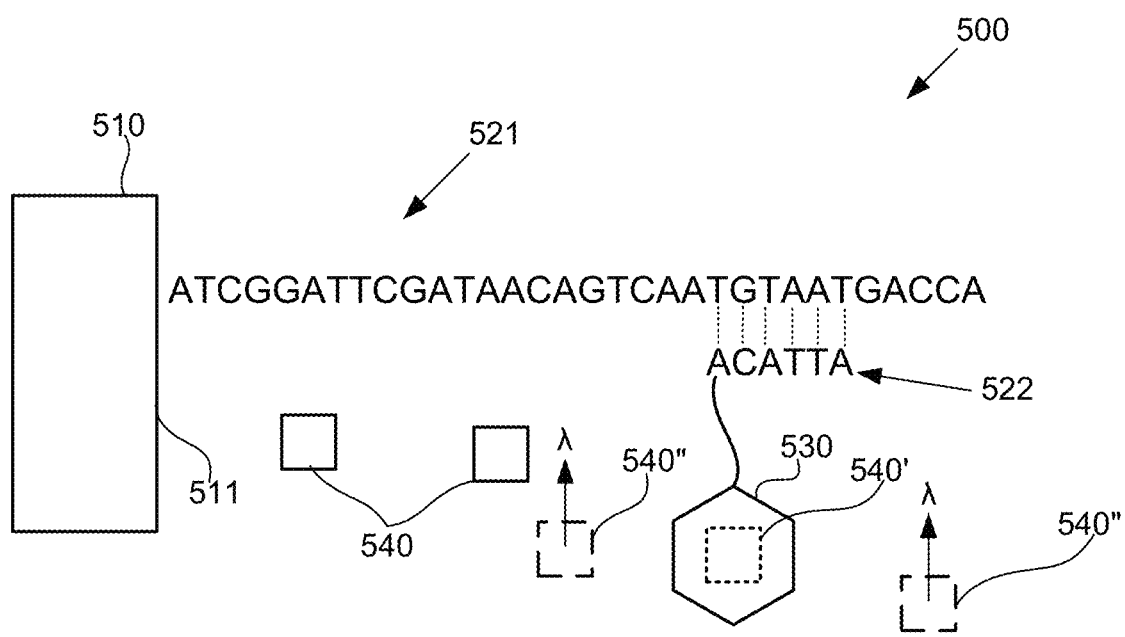
FIG. 5 schematically illustrates a composition for detecting the presence of nucleotides in a polynucleotide using chemiluminescence, according to some embodiments of the present invention. Sequence is disclosed as SEQ ID NO: 1.

For example, FIG. 5 schematically illustrates a composition for detecting the presence of nucleotides in a polynucleotides using chemiluminescence, according to some embodiments of the present invention. Composition 500 illustrated in FIG. 5 includes substrate 510; first nucleotide 521 coupled to surface 511 of substrate 510 and including a plurality of nucleotides; second polynucleotide 522 including a plurality of nucleotides, e.g., ACATTA, that are hybridized to a corresponding plurality of nucleotides of first polynucleotide 521, e.g., to TGTAAT of first polynucleotide 521; and catalyst 530 coupled to a selected nucleotide of second polynucleotide 522, e.g., A.

In certain of the systems, methods, and compositions presented herein, polynucleotides are immobilized to a substrate. In some embodiments, the polynucleotides are covalently immobilized to the substrate. When referring to immobilization of polymers (e.g., polynucleotides) to a substrate, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the polymers (e.g., polynucleotides) remain immobilized or attached to the substrate under the conditions in which it is intended to use the substrate, for example in applications requiring nucleic acid amplification and/or sequencing.

Certain embodiments of the invention may make use of substrates that include an inert substrate or matrix (e.g., a glass slide, polymer bead, or the like) that has been functionalized, for example by application of a layer or coating of an intermediate material that includes one or more reactive groups that permit covalent attachment to a polymer, such as a polynucleotide. Examples of such substrates include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the polymer (e.g., polynucleotide) can be directly covalently attached to the intermediate material (e.g., the hydrogel) but the intermediate material can itself be non-covalently attached to the substrate or matrix (e.g., the glass substrate). The term "covalent attachment to a substrate" is to be interpreted accordingly as encompassing this type of arrangement.

Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference.

As should be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful substrates for some embodiments are located within a flow cell apparatus.

In some embodiments, the substrate includes a patterned surface suitable for immobilization of one or more polynucleotides in an ordered pattern. A "patterned surface" refers to an arrangement of different regions in or on an exposed layer of a substrate. For example, one or more of the regions can be features where one or more polynucleotides are present. The features can be separated by interstitial regions where one or more polynucleotides are not present. In some embodiments, the pattern can include an x-y format of features that are regularly arranged in rows and columns. In some embodiments, the pattern can include a repeating arrangement of features and/or interstitial regions. In some embodiments, the pattern can include a random or irregular arrangement of features and/or interstitial regions. In some embodiments, the one or more polynucleotides are randomly distributed upon the substrate. In some embodiments, the one or more polynucleotides are distributed on a patterned surface. Exemplary patterned surfaces that can be used in the systems, methods, and compositions set forth herein are described in U.S. Pat. Nos. 8,778,849 and 8,778,848, the entire content of each of which is incorporated herein by reference.

In some embodiments, the substrate includes an array of wells or depressions in a surface. This can be fabricated as is generally known in the art using a variety of techniques, including, but not limited to, photolithography, stamping techniques, molding techniques and microetching techniques. As will be appreciated by those in the art, the technique used can depend on the composition and shape of the substrate.

The composition and geometry of the substrate can vary with its use. In some embodiments, the substrate includes a planar structure such as a slide, chip, microchip and/or array. As such, the surface of a substrate can be in the form of a planar layer. In some embodiments, the substrate includes one or more surfaces of a flowcell. The term "flowcell" as used herein refers to a chamber comprising a solid surface across which one or more fluid reagents can be flowed. Examples of flowcells and related fluidic systems and detection platforms that can be readily used in the systems, methods, and compositions of the present disclosure are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; 7,405,281; and US 2008/0108082, the entire content of each of which is incorporated herein by reference.

In some embodiments, the substrate or its surface is non-planar, such as the inner or outer surface of a tube or vessel. In some embodiments, the substrate includes one or more microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for substrates can all be used. "Microsphere Detection Guide" from Bangs Laboratories, Fishers Ind. is a helpful guide. In certain embodiments, the microspheres include magnetic microspheres or beads. The beads need not be spherical; irregular particles can be used. Alternatively or additionally, the beads can be porous. Illustratively, the bead sizes can range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads can be used.

Exemplary methods for attaching a polynucleotide to a surface include reacting an $NH_2$-modified polynucleotide with an epoxysilane-coated or isothiocyanate-coated substrate surface; reacting a succinylated polynucleotide with an aminosilane-coated substrate surface; reacting a disulfide-modified polynucleotide with a mercaptosilane-coated substrate surface; and reacting a hydrazide-modified polynucleotide with an aldehyde-coated or epoxysilane-coated substrate surface. Exemplary methods for coupling a catalyst to a nucleotide include forming an amide bond between a propragylamino-base modified nucleotide and the catalyst using an amide bond forming reaction mediated by a peptide coupling reagent such as O—(N-succinimidyl)-N,N,N',N'-tetramethyluronium tetrafluoroborate (TSTU), N,N'-dicyclohexylcarbodiimide (DCC), 1-ethyl-3-(3-dimethylaminopropyl)carbodiimide (EDCI), or N,N'-dicyclohexylcarbodiimide (DCC).

Substrate 510 optionally includes an optical detector (not specifically illustrated) operable to detect one or more photons emitted by chemiluminogenic molecule(s) responsive to the presence of catalyst 530 and the selected nucleotide of second polynucleotide 522, e.g., A, to which catalyst 530 is coupled. Exemplary substrates and detectors are described elsewhere herein. Catalyst 530 is operable to cause a chemiluminogenic molecule to emit a photon, optionally with facilitation from one or more reagent molecules, as described elsewhere herein. In some embodiments, catalyst 530 also can be cleavable from the selected nucleotide, e.g., A, e.g., by exposing catalyst 530 and the selected nucleotide to one or more suitable reagent molecules for cleaving the coupling between catalyst 530 and the nucleotide, so as to facilitate detecting the selected nucleotide. Exemplary polymers, substrates, catalysts, couplings, chemiluminogenic molecules, reagent molecules, chemiluminogenic reactions, and detection circuitry are described elsewhere herein, e.g., with reference to FIGS. 1A-1C.

As illustrated in FIG. 5, composition 500 further can include, or be contacted with, a plurality of chemiluminogenic molecules 540 that respectively emit photons responsive to interactions with catalyst 530. For example, catalyst 530 can bind or otherwise suitably interact with a selected chemiluminogenic molecule 540', which causes that chemiluminogenic molecule to have an excited state, as represented by the dotted lines of molecule 540' in FIG. 5. Optionally, composition 500 further includes one or more reagent molecule(s) (not specifically illustrated) that can facilitate interaction between catalyst 530 and chemiluminogenic molecules 540 so as to cause the chemiluminogenic molecules to emit respective photons. As illustrated in FIG. 5, after interaction with catalyst 530 and optional reagent molecule(s) causes chemiluminogenic molecules 540 to obtain an excited state 540', such excited states can decay by emitting a corresponding photon, as represented in FIG. 5 by the dashed lines of molecule 540" and arrow with "λ" representing photon emission. Based on the photon emission, the presence of the selected nucleotide, e.g., A, can be detected, e.g., using suitable circuitry configured to detect the photon such as described further below with reference to FIGS. 10A-10B and 11A-11B. In some embodiments, catalyst 530 interacts with a plurality of chemiluminogenic molecules 540, thus causing the emission of a corresponding plurality of photons, thus increasing the detectability of the selected nucleotide, such as described further below with reference to FIG. 12. Based on the detected presence of the selected nucleotide of second polynucleotide 522, e.g., A, the presence of the corresponding nucleotide of the first polynucleotide 521 to which that selected nucleotide is hybridized, e.g., T, can be determined. Accordingly, by detecting the presence of different nucleotides in second nucleotide 522, the sequence of at least a portion of first nucleotide 521 can be determined.

Figure 6A:
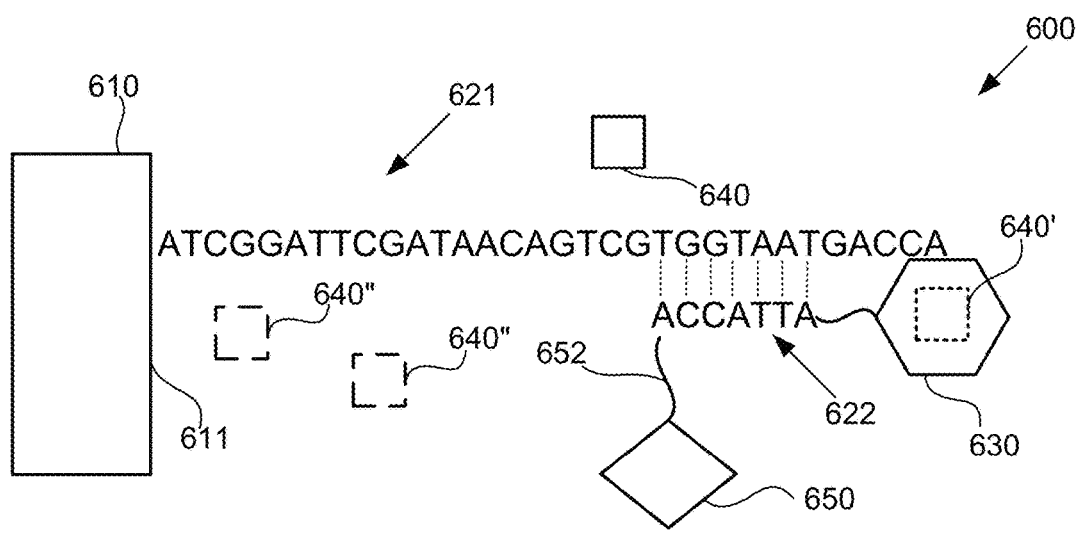
FIGS. 6A-6C schematically illustrate alternative compositions for detecting the presence of nucleotides in a polynucleotide using chemiluminescence, according to some embodiments of the present invention.
Figure 6B:
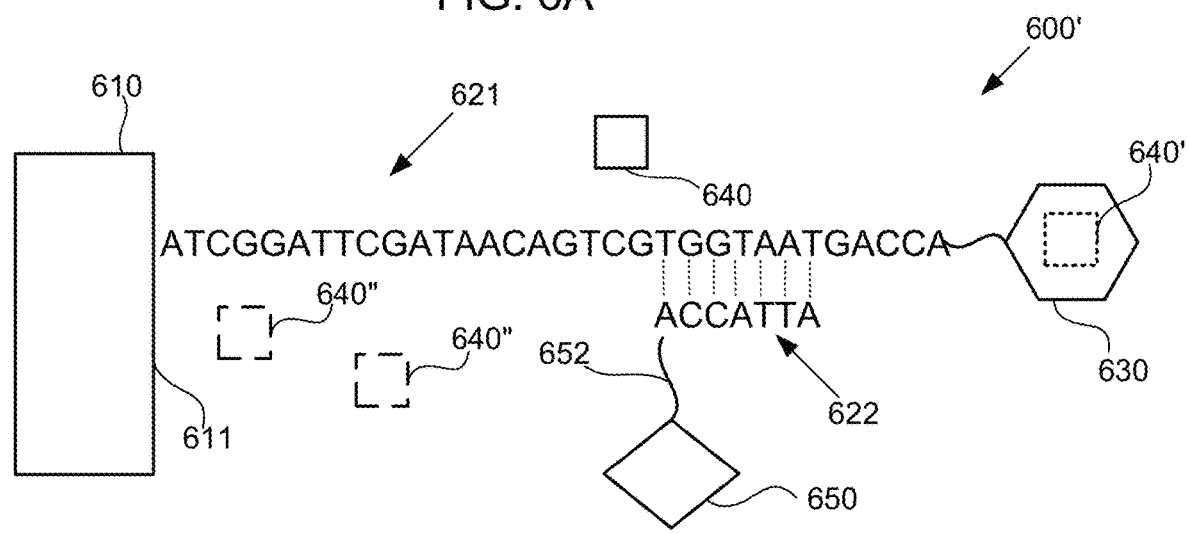
Figure 6C:
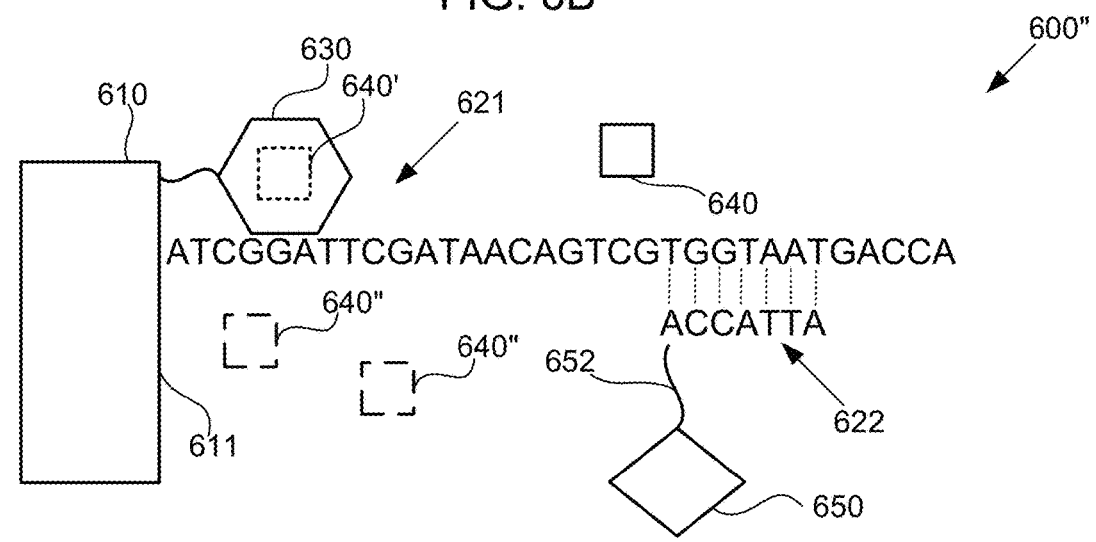

Alternatively, suppression of chemiluminescence can be used to detect the presence of nucleotides in polynucleotides. For example, FIGS. 6A-6C schematically illustrate alternative compositions for detecting the presence of nucleotides in a polynucleotides using chemiluminescence, according to some embodiments of the present invention. Composition 600 illustrated in FIG. 6 includes substrate 610; first nucleotide 621 coupled to surface 611 of substrate 610 and including a plurality of nucleotides; second polynucleotide 622 including a plurality of nucleotides, e.g., ACCATTA, that are hybridized to a corresponding plurality of nucleotides of first polynucleotide 621, e.g., to TGGTAAT of first polynucleotide 621; catalyst 630 coupled to a first selected nucleotide of second polynucleotide; and quencher 650 coupled to a second selected nucleotide of second polynucleotide 622, e.g., A, via coupling 652. Substrate 610 optionally includes an optical detector (not specifically illustrated) operable to detect one or more photons emitted by chemiluminogenic molecule(s) responsive to the presence of catalyst 630 in the absence of quencher 650. Exemplary substrates and detectors are described elsewhere herein. Catalyst 630 is operable to cause a chemiluminogenic molecule to emit a photon in the absence of quencher 650, optionally with facilitation from one or more reagent molecules, as described elsewhere herein. As illustrated in FIG. 6A, although interaction with catalyst 630 and optional reagent molecule(s) causes chemiluminogenic molecules 640 to obtain an excited state 640', quencher 650 inhibits such excited states from emitting a corresponding photon, and instead causes the excited state molecule to decay without photon emission, as represented in FIG. 6A by the dashed lines of molecule 640". Based on the inhibited photon emission, the presence of second selected nucleotide, e.g., A can be detected, e.g., using suitable circuitry configured to detect the inhibition of photons such as described further below with reference to FIGS. 10A-10B and 11A-11B. In some embodiments, quencher 650 also can be cleavable from the second selected nucleotide, e.g., A, e.g., by exposing quencher 650 and the second selected nucleotide to one or more suitable reagent molecules for cleaving the coupling between quencher and that nucleotide, so as to facilitate detecting that nucleotide. Exemplary polymers, substrates, catalysts, couplings, chemiluminogenic molecules, reagent molecules, chemiluminogenic reactions, and detection circuitry are described elsewhere herein, e.g., with reference to FIGS. 1A-1C. In a manner analogous to that described elsewhere herein, composition 600 further can include a plurality of chemiluminogenic molecules 640 and optionally can include one or more reagent molecule(s) (not specifically illustrated) that can facilitate interaction between catalyst 630 and chemiluminogenic molecules 640 so as to cause the chemiluminogenic molecules to emit respective photons in the absence of quencher 650. Based on the inhibition of photon emission resulting from interaction between quencher 650 and excited state chemiluminogenic molecules 640', the presence of the selected nucleotide, e.g., A, can be detected, e.g., using suitable circuitry configured to detect the photon such as described further below with reference to FIGS. 10A-10B and 11A-11B. Based on the detected presence of the second selected nucleotide of second polynucleotide 622, e.g., A, the presence of the corresponding nucleotide of the first polynucleotide 621 to which that selected nucleotide is hybridized, e.g., T, can be determined. Accordingly, by detecting the presence of different nucleotides in second nucleotide 622, the sequence of at least a portion of first nucleotide 621 can be determined.

Note that catalyst 630 can be provided at any suitable location that is sufficiently close to quencher 650 such that quencher 650 can inhibit photon emission from chemiluminogenic molecules 640 that otherwise can result from interactions between catalyst 630 and chemiluminogenic molecules 640. As such, catalyst 630 need not necessarily be coupled to second polynucleotide 622. For example, FIG. 6B illustrates an alternative composition 600' in which catalyst 630 is coupled to first polynucleotide 621, and FIG. 6C illustrates another alternative composition 600" in which catalyst 630 is coupled to surface 611 of substrate 610.

Figure 7:
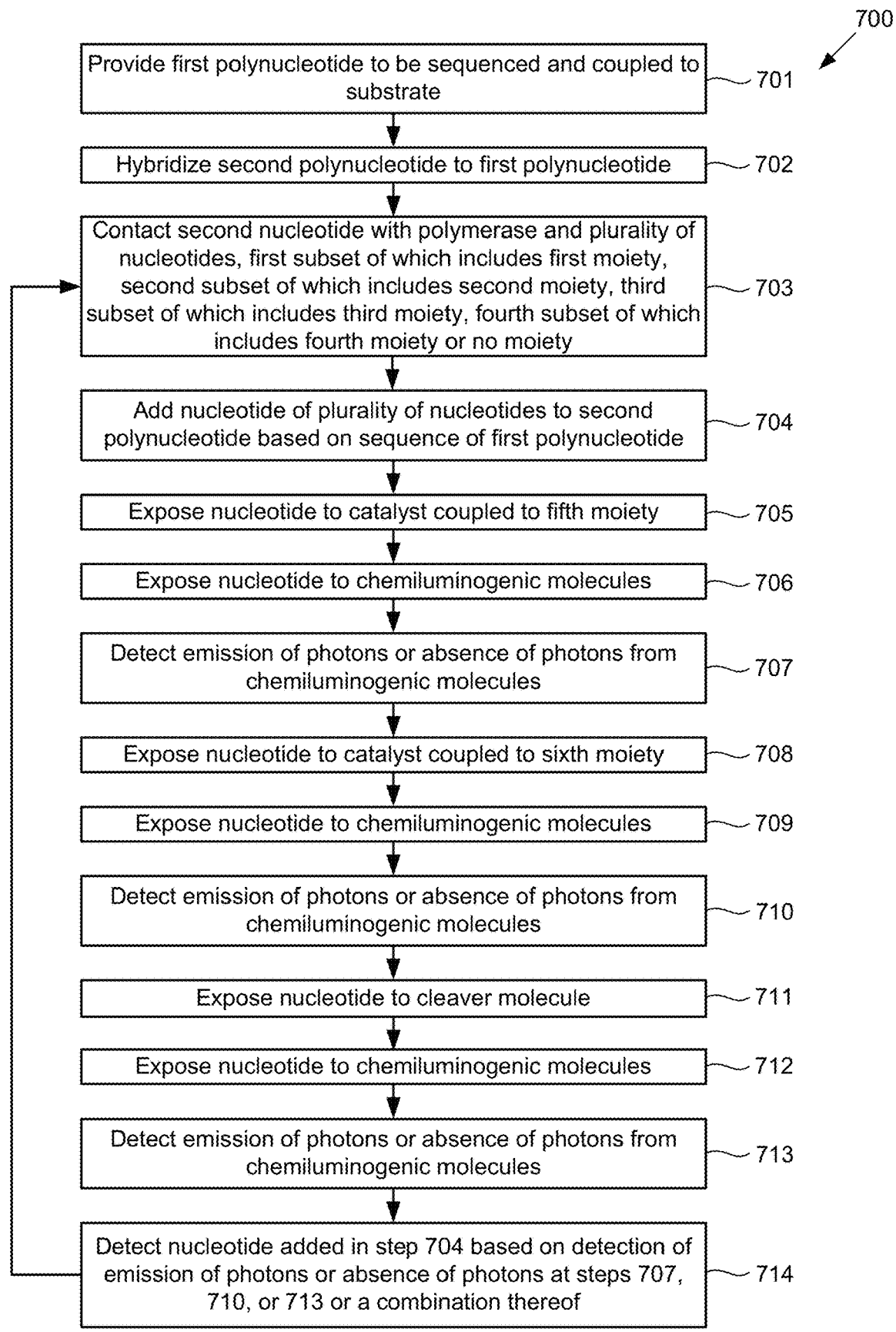
FIG. 7 illustrates a method for detecting the presence of nucleotides using in a polynucleotide using chemiluminescence, according to some embodiments of the present invention.

An illustrative sequence of steps that can be used so as to sequentially detect the presence of a plurality of nucleotides in a polynucleotide, and thus to determine the sequence of that polynucleotide, now will be described with reference to FIGS. 7 and 8A-8M. FIG. 7 illustrates a method for detecting the presence of nucleotides using in a polynucleotide using chemiluminescence, according to some embodiments of the present invention. FIGS. 8A-8M schematically illustrate compositions for detecting the presence of nucleotides in a polynucleotide using chemiluminescence, according to some embodiments of the present invention.

Figure 8A:
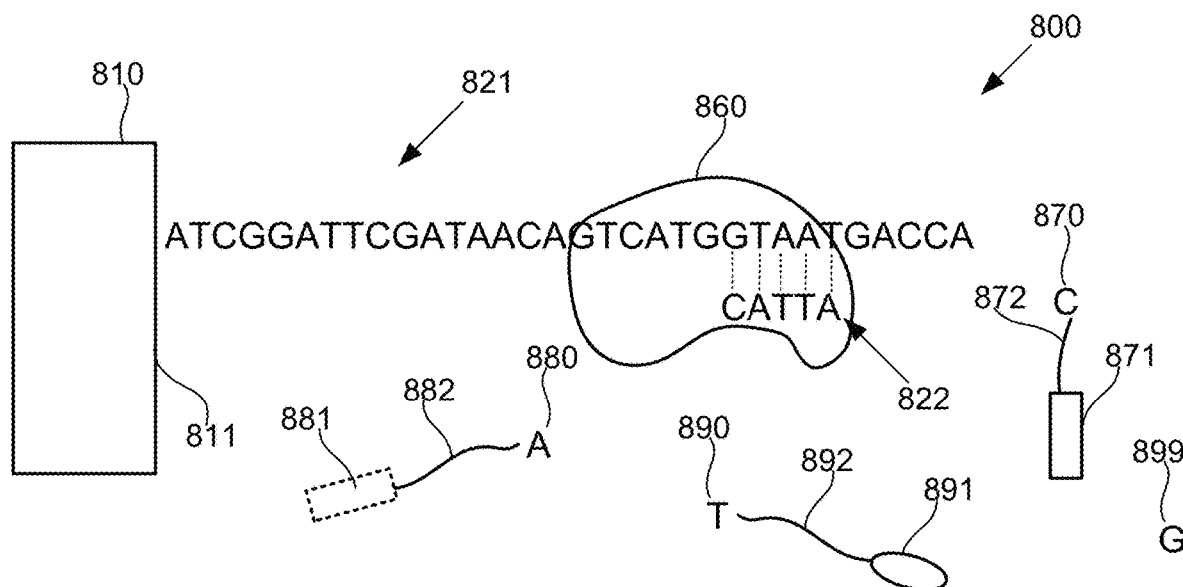
FIGS. 8A-8M schematically illustrate compositions for detecting the presence of nucleotides in a polynucleotide using chemiluminescence, according to some embodiments of the present invention.

Method 700 illustrated in FIG. 7 includes providing a first polynucleotide to be sequenced and coupled to a substrate (701). For example, first polynucleotide 821 illustrated in composition 800 of FIG. 8A can be coupled to surface 811 of substrate 810 using any suitable coupling provided herein or otherwise known in the art. Method 700 illustrated in FIG. 7 also includes hybridizing a second polynucleotide to the first polynucleotide (702). For example, second polynucleotide 822 illustrated in FIG. 8A can be hybridized to first polynucleotide 821 using any suitable technique provided herein or otherwise known in the art. Although FIG. 8A illustrates second polynucleotide 822 as having the sequence CATTA hybridized to the sequence GTAAT of first polynucleotide 821, it should be appreciated that the first and second polynucleotides can have any suitable respective sequences that hybridize to one another.

Referring again to FIG. 7, method 700 further includes contacting the second nucleotide with a polymerase and a plurality of nucleotides (703). A first subset of the plurality of nucleotides can include a first moiety, a second subset of the plurality of nucleotides can include a second moiety, a third subset of the plurality of nucleotides can include a third moiety, and a fourth subset of the plurality of nucleotides can include a fourth moiety or no moiety (703). For example, in the embodiment illustrated in FIG. 8A, composition 800 is contacted with polymerase 860 that couples to and binds first polynucleotide 821 and second polynucleotide 822 in such a manner as to be operable to add a nucleotide to second polynucleotide 822 based on the sequence of first polynucleotide 821. Composition 800 also is contacted with a plurality of nucleotides that can be coupled to one or more different moieties than one another so as to facilitate distinguishing the presence of one particular nucleotide in second polynucleotide 822 from the other nucleotides in that polynucleotide. In one illustrative, non-limiting example, nucleotide C 870 can be coupled to first moiety 871 via first coupling 872; nucleotide A 880 can be coupled to second moiety 881 via second coupling 882; nucleotide T 890 can be coupled to third moiety 891 via third coupling 892; and nucleotide G can be left "blank" without being coupled to any moiety, or alternatively can be coupled to a fourth moiety via a fourth coupling (not specifically illustrated). It should be appreciated that any nucleotide other than G alternatively can be left "blank" instead of G. The moieties to which the nucleotides are coupled, or the couplings therebetween, or both the moieties and the nucleotides, can be selected so as to facilitate identification of the particular nucleotide that has been added to second polynucleotide 822, e.g., using a series of steps in which nucleotides coupled to certain moieties are exposed to catalyst(s) coupled to certain moieties that can interact with the moieties of only certain subset(s) of the nucleotides or selectively can be cleaved from only certain subset(s) of the nucleotides, in a manner such as provided herein.

Figure 8B:
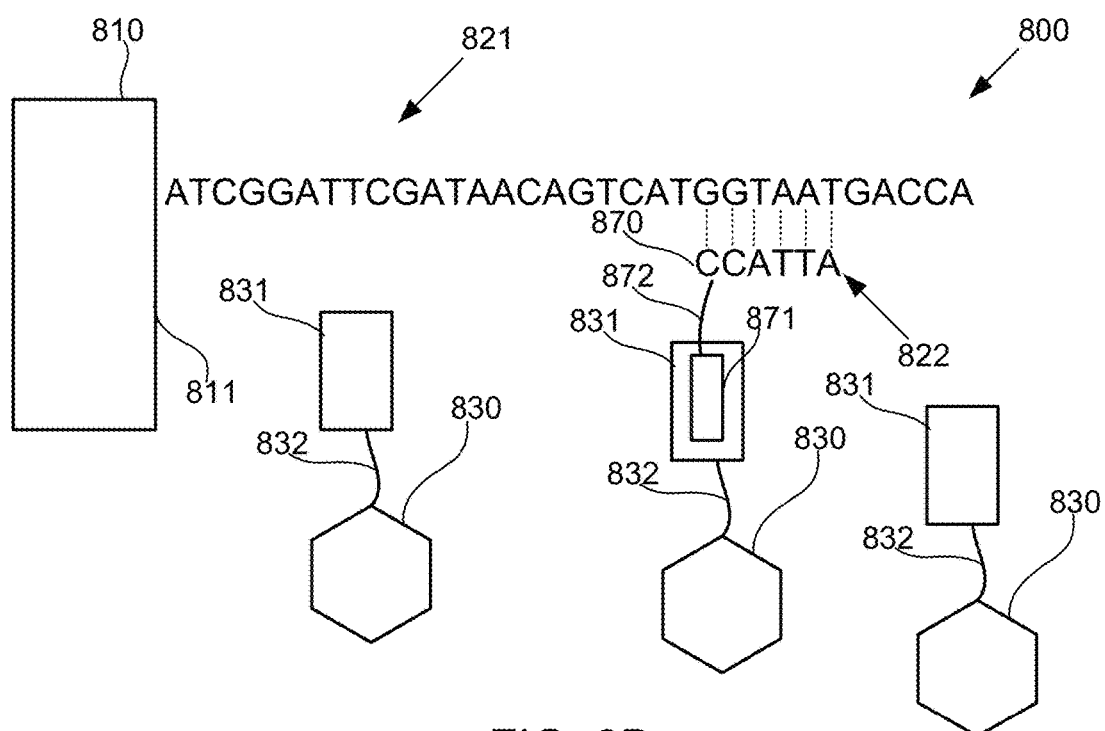

As illustrated in FIG. 7, method 700 also includes adding a nucleotide of the plurality of nucleotides to the second polynucleotide based on the sequence of the first polynucleotide (704). For example, polymerase 860 illustrated in FIG. 8A can be operable to add another nucleotide to second polynucleotide 822 based on the sequence of first polynucleotide 821, e.g., adds C 870 to second polynucleotide 822 based on the G present in the sequence of first polynucleotide 821, as illustrated in FIG. 8B. As noted further above, nucleotide C 870 is coupled to moiety 871 via coupling 872. After adding nucleotide C 870 to second polynucleotide 822, polymerase 860 can be washed away.

Referring again to FIG. 7, method 700 includes exposing the nucleotide to a catalyst coupled to a fifth moiety (705). For example, as illustrated in FIG. 8B, composition 800 can be contacted with catalyst 830 coupled to moiety 831 via coupling 832. Moiety 831 of catalyst 830 couples to moiety 871 of nucleotide C 870, thus coupling catalyst 830 to second polynucleotide 822. Moiety 831 of catalyst 830 and moiety 871 of nucleotide C 870 can be selected such that if a nucleotide other than C had been added to second polynucleotide 822 based on the sequence of first polynucleotide 821, moiety 831 may not necessarily couple to the moiety of that other nucleotide. Put another way, moieties 831 and 871 can be selected so as to couple with one another and to not necessarily couple with one or more other moieties. Additionally, or alternatively, and as described in greater detail below, coupling 872 or moiety 871 of nucleotide C 870 optionally can be selected so as to permit selective cleaving of catalyst 830 from nucleotide C during a subsequent step, which further can facilitate detection of nucleotide C. Excess catalyst 830 that did not couple to nucleotide C 870 can be washed away.

Figure 8C:
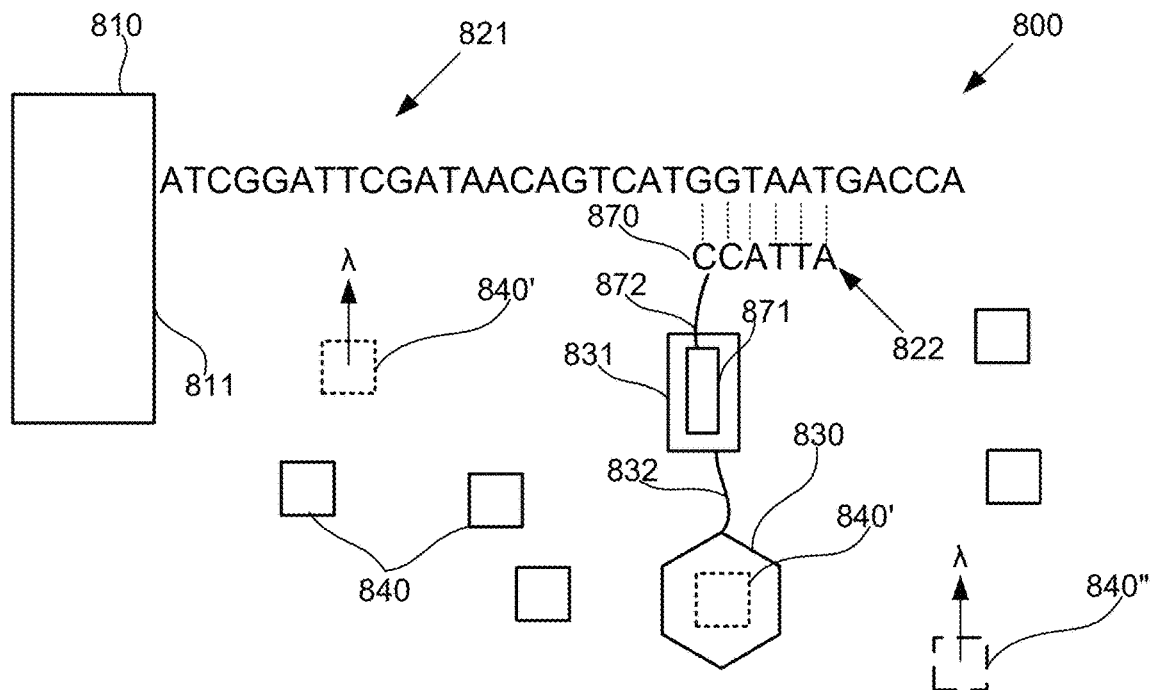

Method 700 illustrated in FIG. 7 also includes exposing the nucleotide to chemiluminogenic molecules (706). For example, as illustrated in FIG. 8C, composition 800 can be contacted with a plurality of chemiluminogenic molecules 840. Catalyst can suitably interact with a selected chemiluminogenic molecule 840' of the plurality of chemiluminogenic molecules 840, which causes that chemiluminogenic molecule to have an excited state, as represented by the dotted lines of molecule 840' in FIG. 8C. Optionally, one or more reagent molecule(s) (not specifically illustrated) also can be provided that can facilitate interaction between catalyst 830 and chemiluminogenic molecules 840 so as to cause the chemiluminogenic molecules to emit respective photons. As illustrated in FIG. 8C, after interaction with catalyst 830 and optional reagent molecule(s) causes chemiluminogenic molecules 840 to obtain an excited state 840', such excited states can decay to a ground state, as represented in FIG. 8C by the dashed lines of molecule 840", by emitting a corresponding photon, as represented by the arrow with "λ".

Method 700 illustrated in FIG. 7 includes detecting emission of photons or absence of photons from the chemiluminogenic molecules (707). For example, in the embodiment illustrated in FIG. 8C, photon emission from excited state chemiluminogenic molecules 840' can be detected, e.g., using suitable circuitry configured to detect the photon such as described further below with reference to FIGS. 10A-10B and 11A-11B. In some embodiments, catalyst 830 interacts with a plurality of chemiluminogenic molecules 840, thus causing the emission of a corresponding plurality of photons, thus increasing the detectability of nucleotide C 870, such as described further below with reference to FIG. 12. Note that if the nucleotide that had been added to second polynucleotide 822 had been a nucleotide other than C, and thus was coupled to a moiety other than first moiety 871, then moiety 831 coupled to catalyst 830 may not necessarily have coupled to moiety 871; as such, photons may not be necessarily emitted during step 705 or detected during step 706 for that nucleotide; such an absence of photons also can be detected and used to identify the nucleotide that has been added to second nucleotide 822.

Figure 8D:
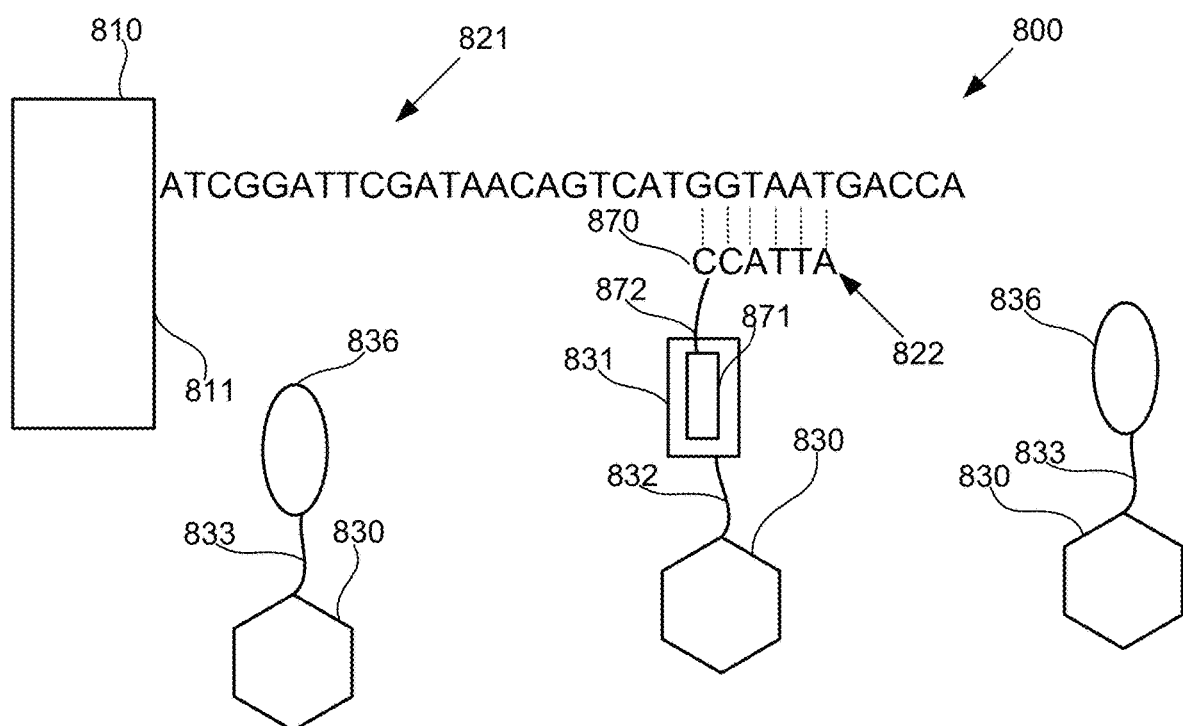

Referring again to FIG. 7, method 700 includes exposing the nucleotide to a catalyst coupled to a sixth moiety (708). For example, as illustrated in FIG. 8D, composition 800 can be contacted with catalyst 830 coupled to moiety 836 via coupling 833. However, because moiety 871 of nucleotide C 870 is already coupled to moiety 831 of catalyst 830, or because moiety 871 of nucleotide C 870 does not couple to moiety 836 of catalyst 830, or both, moiety 836 does not become coupled to nucleotide C 870 in this illustrative embodiment. Method 700 illustrated in FIG. 7 also includes exposing the nucleotide to chemiluminogenic molecules (709), e.g., in a manner analogous to that described above with reference to step 706. Method 700 illustrated in FIG. 7 also includes detecting emission of photons or absence of photons from the chemiluminogenic molecules (710), e.g., in a manner analogous to that described above with reference to step 707. Note that because nucleotide C 870 remains coupled to catalyst 830 via moieties 871 and 831 during steps 708-710, photon emission from excited state chemiluminogenic molecules 840' can be detected in a manner analogous to that described above with reference to steps 706-707.

Figure 8E:
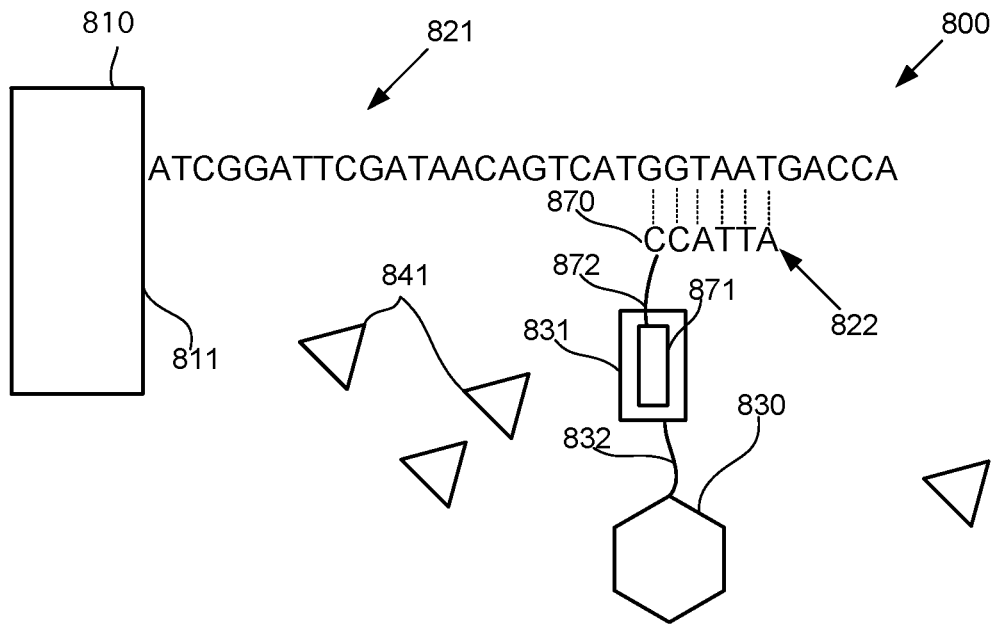

Referring again to FIG. 7, method 700 further includes exposing the nucleotide to a cleaver molecule (711). For example, FIG. 8E illustrates contacting composition 800 with molecules 841 that can selectively cleave one or more certain catalyst moieties from one or more certain nucleotide moieties, but substantially does not cleave moiety 831 of catalyst 830 from moiety 871 of nucleotide C 870. Exemplary cleaver molecules include trishydroxypropylphosphine (THP) and triscarboxyethylphosphine (TCEP), although others suitably can be used depending on the nature of the attachment between the catalyst and the nucleotide. For example, cleavage of disulfide bonds or other reductive cleavage groups can be accomplished by a reducing agent. Reduction of a disulfide bond results in the release of the catalyst moiety from the nucleotide moiety, for example a hapten or hapten conjugate. Reducing agents useful in practicing embodiments as described herein include, but are not limited to, phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol and tris (2-carboxyethyl)phosphine (TCEP), tris (hydroxymethyl)phosphine (THP) and β-[tris (hydroxymethyl)phosphine] propionic acid (THPP). In some embodiments, a reducing agent used for cleaving a disulphide bond that couples a catalyst to a nucleotide as described herein is DTT. In some embodiments, the concentration of a reducing reagent, for example DTT, utilized for cleaving a disulfide bond is at least 1 to 1000 mM, at least 20 to 800 mM, at least 40 to 500 mM, and preferably at least 50 to 200 mM. In some embodiments, a reducing agent used for cleaving a disulphide bond that couples a catalyst to a nucleotide as described herein is a phosphine reagent, a water soluble phosphine reagent, a nitrogen containing phosphine reagent and salts and derivatives thereof. Exemplary phosphine reagents include, but are not limited to, TCEP, THP and those disclosed in US patent publication 2009/0325172 (incorporated herein by reference in its entirety) such as triaryl phosphines, trialkyl phosphines, sulfonate containing and carboxylate containing phosphines and derivatized water soluble phosphines. In some embodiments, the concentration of a phosphine utilized for cleaving a disulfide bond is at least 0.5-500 mM, at least 5 to 50 mM, and preferably at least 10 to 40 mM. Methods and compositions as described herein are not limited by any particular cleavage group and alternatives will be readily apparent to a skilled artisan and are considered within the scope of the present disclosure.

Method 700 illustrated in FIG. 7 further can include exposing the nucleotide to chemiluminogenic molecules (712), e.g., in a manner analogous to that described above with reference to step 706. Method 700 illustrated in FIG. 7 also includes detecting emission of photons or absence of photons from the chemiluminogenic molecules (713), e.g., in a manner analogous to that described above with reference to step 707.

Referring still to FIG. 7, method 700 can include detecting the nucleotide that was added in step 704 based on the detection of the emission of photons or absence of photons at steps 707, 710, or 713 or a combination thereof (714). For example, without necessarily knowing a priori the identity of the selected nucleotide added in step 704, based upon the detection at step 707 of photon emission after exposing the nucleotide to the catalyst coupled to fifth moiety at step 705 and the chemiluminogenic molecules at step 706, it can be determined that the nucleotide became coupled during step 705 to catalyst 730. Additionally, based upon the detection at step 713 of photon emission after exposing the nucleotide to the cleaver molecule at step 711 and the chemiluminogenic molecules at step 712, it can be determined that the nucleotide remained coupled during step 711 to catalyst 730. Based upon these detections, and knowledge of the compatibility of moieties 831 and 871 and the action of cleaver molecule 841 thereupon, it can be determined that the nucleotide is C 870.

It should be appreciated that for any given sequence of first polynucleotide 821, it is approximately as likely that polymerase 860 added G, T, A, or C to second polynucleotide 822 during step 704. Steps 705-714 analogously can be used so as to detect nucleotides other than C. For example, in the exemplary alternative composition 800' illustrated in FIG. 8F, nucleotide A 880 was added to alternative second polynucleotide 822' based on the sequence of alternative first polynucleotide 821'.

Figure 8F:
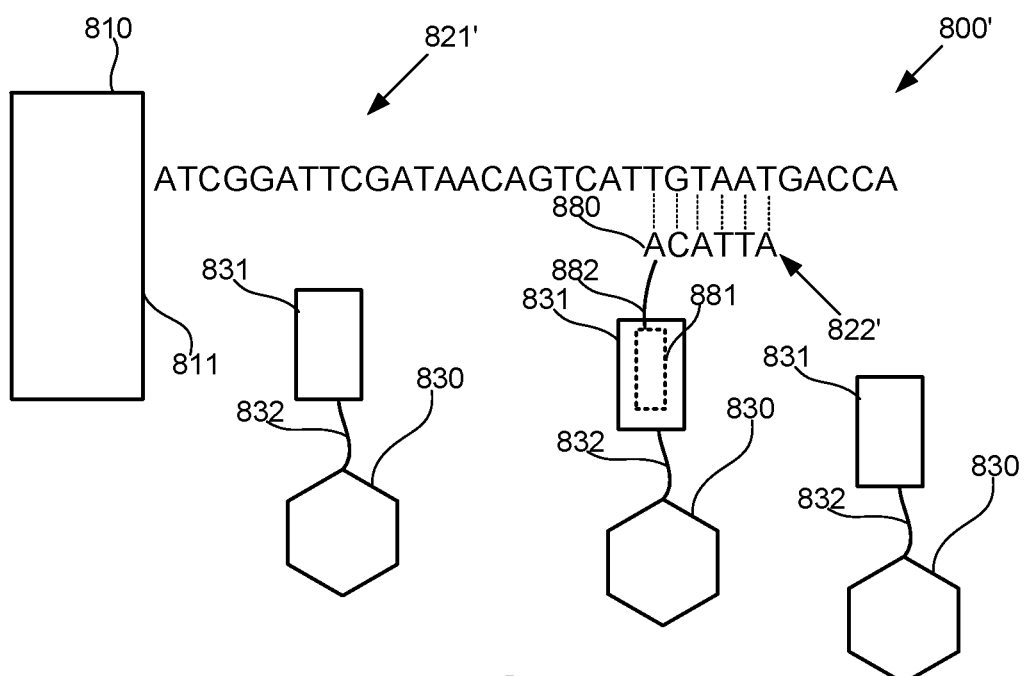

Referring again to FIG. 7, method 700 includes exposing the nucleotide to a catalyst coupled to a fifth moiety (705), in a manner analogous to that described above with reference to FIG. 8B. For example, as illustrated in FIG. 8F, alternative composition 800' can be contacted with catalyst 830 coupled to moiety 831 via coupling 832. Moiety 831 of catalyst 830 couples to moiety 881 of nucleotide A 880, thus coupling catalyst 830 to second polynucleotide 822. Moiety 831 of catalyst 830 and moiety 881 of nucleotide A 880 can be selected such that if a nucleotide other than A had been added to second polynucleotide 822 based on the sequence of first polynucleotide 821, moiety 831 may not necessarily couple to the moiety of that other nucleotide. Put another way, moieties 831 and 881 can be selected so as to couple with one another and to not necessarily couple with one or more other moieties. However, in the illustrated embodiment, moiety 831 can be selected so as to couple both with moiety 871 of nucleotide C and with moiety 881 of nucleotide A. For example, moiety 831 can include streptavidin, moiety 871 can include biotin or a biotin derivative, and moiety 881 can include a biotin or biotin derivative having a different reactivity than the biotin or biotin derivative of moiety 871. Nucleotides A and C can be distinguished from one another based on the different reactivities of the biotin or biotin derivatives coupled thereto. For example, moiety 871 of nucleotide C 870 can be selected so as to permit selective cleaving of catalyst 830 from nucleotide C during step 711, or moiety 881 of nucleotide A 880 can be selected so as to permit selective cleaving of catalyst 830 from nucleotide A during step 711, either of which further can facilitate distinguishing nucleotide C from nucleotide A. Alternatively, moieties 871 and 881 of nucleotides A and C can be the same as one another, but respective couplings 872 and 882 can have different cleavabilities than one another, thus facilitating selective cleaving of catalyst 830 from nucleotide C or from nucleotide A during step 711 and thus facilitating distinguishing nucleotide C from nucleotide A.

Figure 8G:
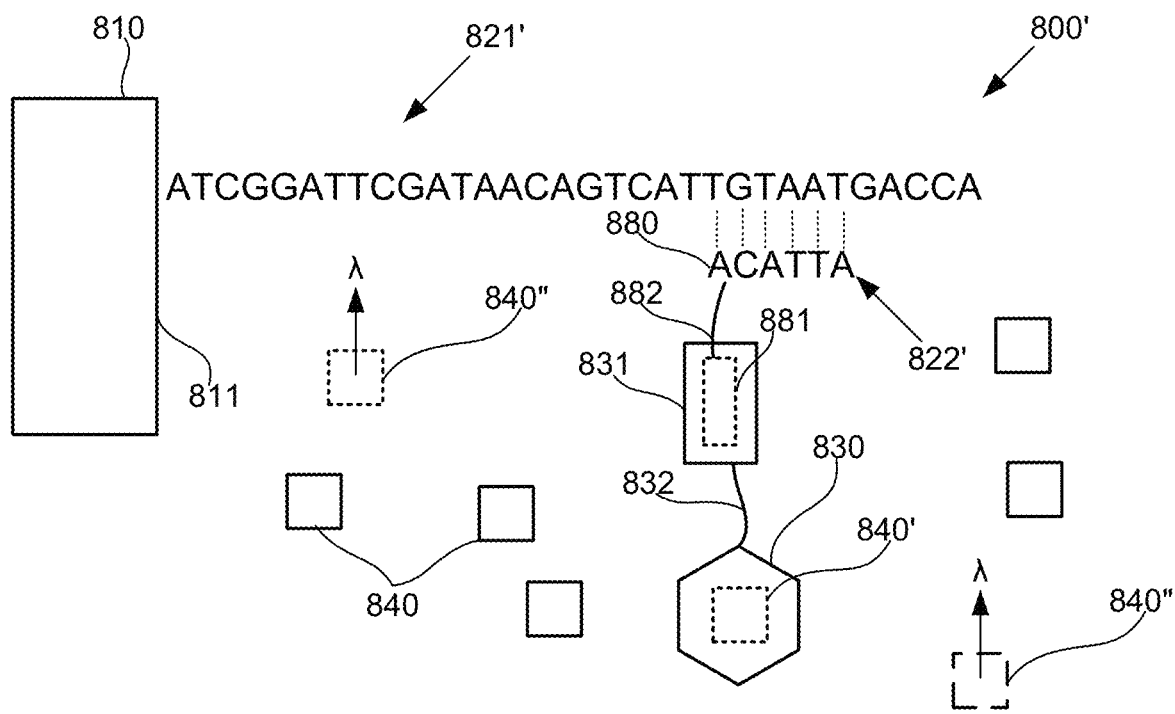

Method 700 illustrated in FIG. 7 also includes exposing the nucleotide to chemiluminogenic molecules (706) and detecting emission of photons or absence of photons from the chemiluminogenic molecules (707), e.g., as described above with reference to FIG. 8C and as illustrated in FIG. 8G. Method 700 also can include exposing the nucleotide to a catalyst coupled to a sixth moiety (708). For example, in a manner analogous to that described above with reference to FIG. 8D, composition 800 can be contacted with catalyst 830 coupled to moiety 836 via coupling 833. However, because moiety 881 of nucleotide A 880 is already coupled to moiety 831 of catalyst 830, or because moiety 881 of nucleotide A 880 does not couple to moiety 836 of catalyst 830, or both, moiety 836 does not become coupled to nucleotide A 880 in this illustrative embodiment. Method 700 illustrated in FIG. 7 also includes exposing the nucleotide to chemiluminogenic molecules (709), e.g., in a manner analogous to that described above with reference to step 706. Method 700 illustrated in FIG. 7 also includes detecting emission of photons or absence of photons from the chemiluminogenic molecules (710), e.g., in a manner analogous to that described above with reference to step 707.

Figure 8H:
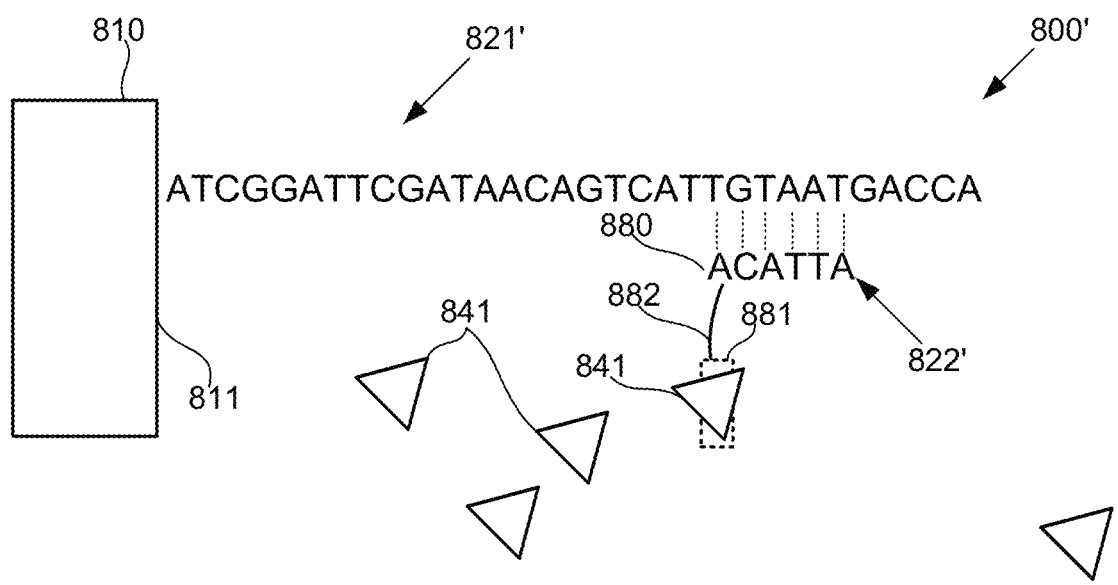

Referring still to FIG. 7, method 700 further includes exposing the nucleotide to a cleaver molecule (711) in a manner analogous to that described above with reference to FIG. 8E. For example, FIG. 8H illustrates contacting composition 800' with molecules 841 that can selectively cleave one or more certain catalyst moieties from one or more certain nucleotide moieties. However, whereas nucleotide C 870 remained coupled to catalyst 830 via moieties 871 and 831 during step 711, FIG. 8H illustrates that cleaver molecule 841 cleaves moiety 831 of catalyst 830 from moiety 881 of nucleotide A 880. Method 700 illustrated in FIG. 7 further can include exposing the nucleotide to chemiluminogenic molecules (712), e.g., in a manner analogous to that described above with reference to step 706. Method 700 illustrated in FIG. 7 also includes detecting emission of photons or absence of photons from the chemiluminogenic molecules (713), e.g., in a manner analogous to that described above with reference to step 707. An absence of photon emission from excited state chemiluminogenic molecules 840', resulting from an absence of catalyst 830, can be detected in a manner analogous to that described above with reference to steps 706-707.

Referring still to FIG. 7, method 700 can include detecting the nucleotide that was added in step 704 based on the detection of the emission of photons or absence of photons at steps 707, 710, or 713 or a combination thereof (714). For example, without necessarily knowing a priori the identity of the selected nucleotide added in step 704, based upon the detection at step 707 of photon emission after exposing the nucleotide to the catalyst coupled to fifth moiety at step 705 and the chemiluminogenic molecules at step 706, it can be determined that the nucleotide became coupled during step 705 to catalyst 730. Additionally, based upon the detection at step 713 of an absence of photons after exposing the nucleotide to the cleaver molecule at step 711 and the chemiluminogenic molecules at step 712, it can be determined that the nucleotide was cleaved during step 711 from catalyst 730. Based upon these two detections, and knowledge of the compatibility of moieties 831 and 871 and the action of cleaver molecule 841 thereupon, it can be determined that the nucleotide is A 880.

Figure 8I:
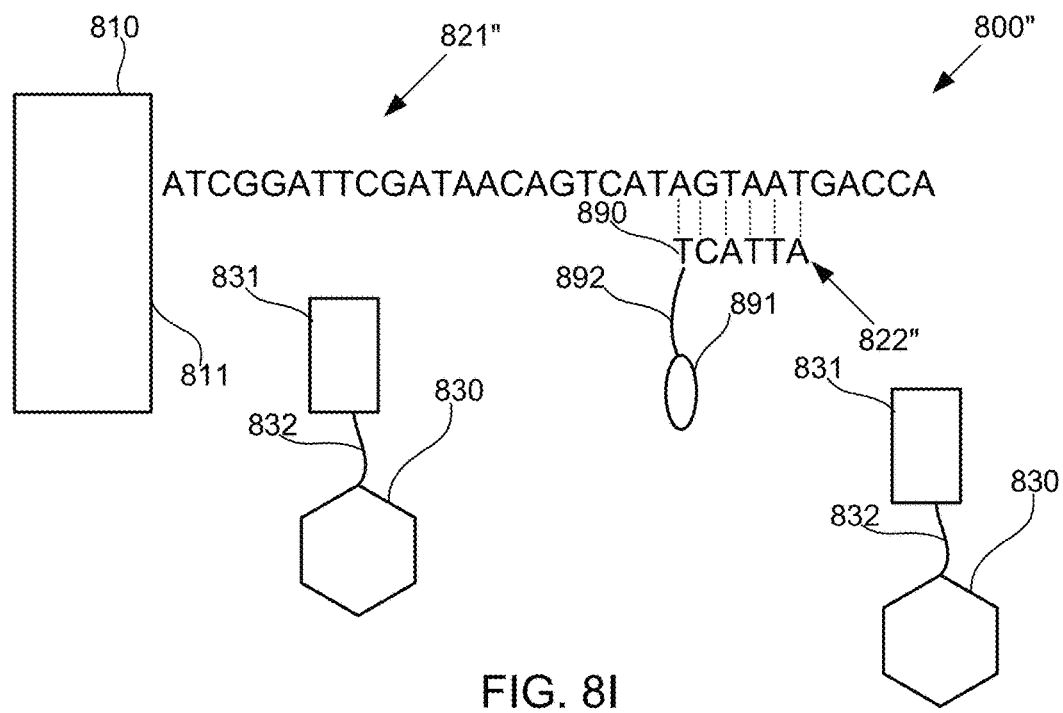
Figure 8J:
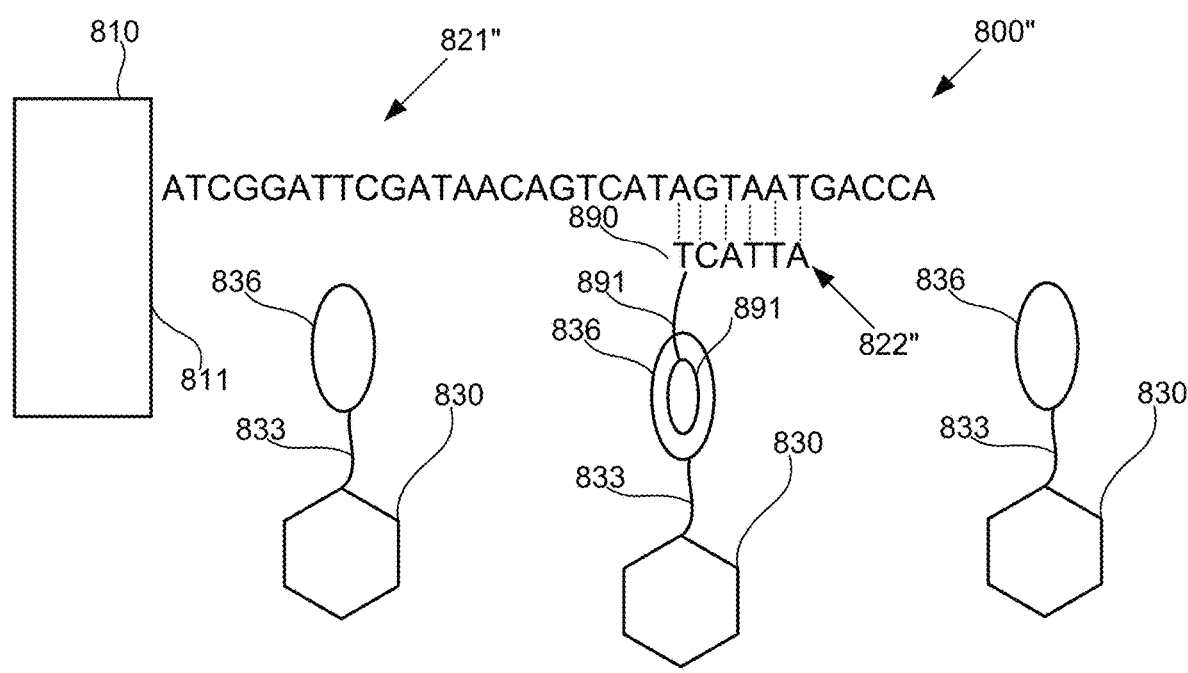
Figure 8K:
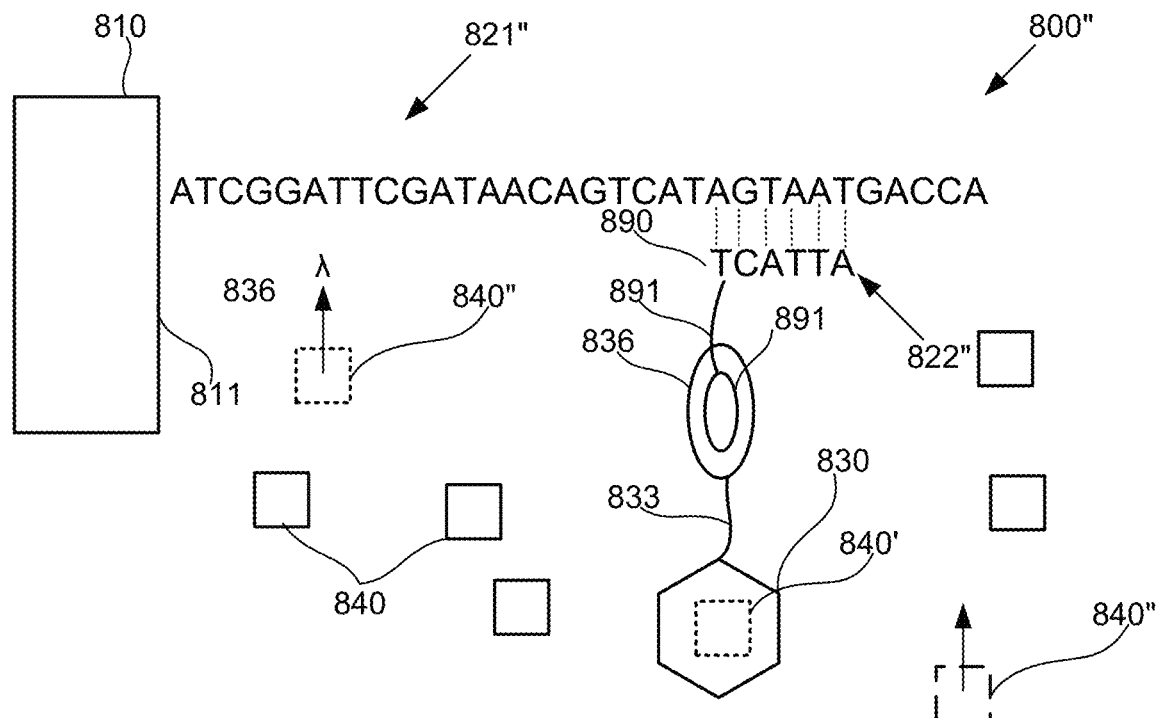

As yet another example, in the exemplary alternative composition 800" illustrated in FIG. 8K, nucleotide T 890 was added to alternative second polynucleotide 822" based on the sequence of alternative first polynucleotide 821".

Referring again to FIG. 7, method 700 includes exposing the nucleotide to a catalyst coupled to a fifth moiety (705), in a manner analogous to that described above with reference to FIGS. 8B and 8F. For example, as illustrated in FIG. 8I, alternative composition 800" can be contacted with catalyst 830 coupled to moiety 831 via coupling 832. However, moiety 831 of catalyst 830 does not couple to moiety 891 of nucleotide A 880, and as such, catalyst 830 does not become coupled to second polynucleotide 822 during step 705. For example, moiety 831 can include streptavidin, and moiety 891 can include digoxigenin or anti-digoxigenin. Method 700 illustrated in FIG. 7 also includes exposing the nucleotide to chemiluminogenic molecules (706) and detecting emission of photons or absence of photons from the chemiluminogenic molecules (707), e.g., as described above with reference to FIG. 8C. Because catalyst 830 is not present during step 706, an absence of photons can be detected during step 707 in this example. Method 700 also can include exposing the nucleotide to a catalyst coupled to a sixth moiety (708). For example, in a manner analogous to that described above with reference to FIG. 8D, and as illustrated in FIG. 8J, alternative composition 800" can be contacted with catalyst 830 coupled to moiety 836 via coupling 833. Moiety 891 of nucleotide T 890 couples to moiety 836 of catalyst 830. Method 700 illustrated in FIG. 7 also includes exposing the nucleotide to chemiluminogenic molecules (709), e.g., in a manner analogous to that described above with reference to step 706. Method 700 illustrated in FIG. 7 also includes detecting emission of photons or absence of photons from the chemiluminogenic molecules (710), e.g., in a manner analogous to that described above with reference to step 707. As illustrated in FIG. 8K, based upon the presence of catalyst 830 during step 709, excited chemiluminogenic molecules 840' emit photons that are detectable at step 710.

Figure 8L:
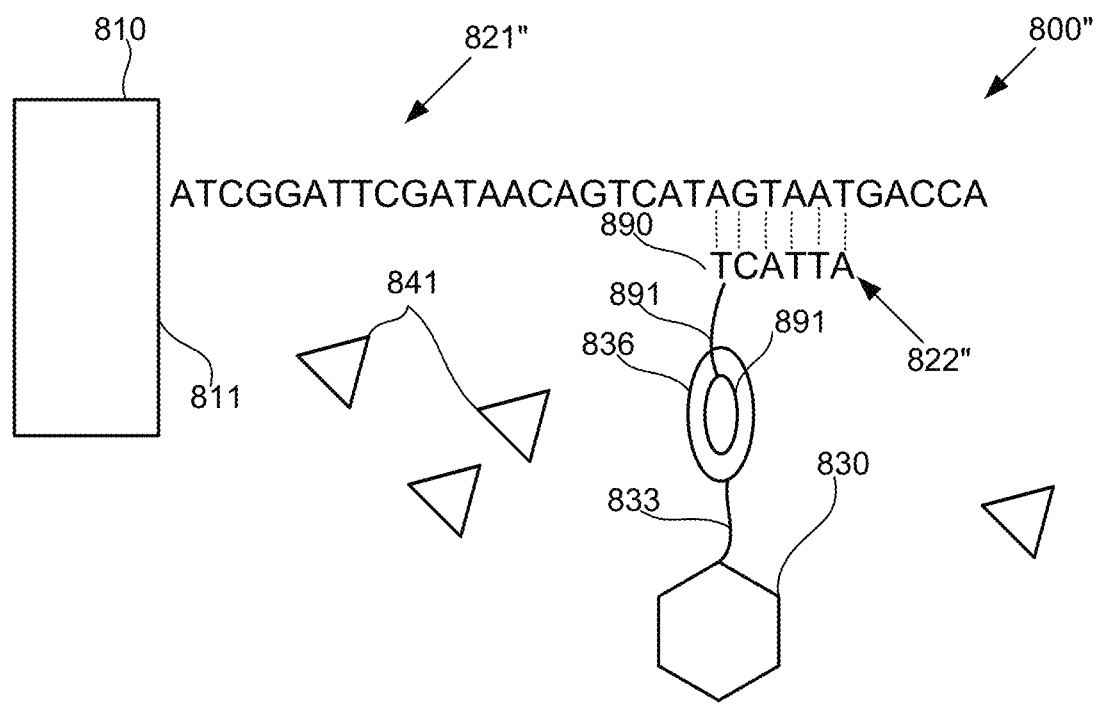

Referring still to FIG. 7, method 700 further includes exposing the nucleotide to a cleaver molecule (711) in a manner analogous to that described above with reference to FIG. 8E. For example, FIG. 8L illustrates contacting composition 800" with molecules 841 that can selectively cleave one or more certain catalyst moieties from one or more certain nucleotide moieties. However, nucleotide T 890 remains coupled to catalyst 830 via moieties 891 and 836 during step 711 because cleaver molecules 841 substantially do not cleave moiety 891 from moiety 836. Method 700 illustrated in FIG. 7 further can include exposing the nucleotide to chemiluminogenic molecules (712), e.g., in a manner analogous to that described above with reference to step 706. Method 700 illustrated in FIG. 7 also includes detecting emission of photons or absence of photons from the chemiluminogenic molecules (713), e.g., in a manner analogous to that described above with reference to step 707. Photon emission from excited state chemiluminogenic molecules 840', resulting from presence of catalyst 830, can be detected in a manner analogous to that described above with reference to steps 706-707.

Referring still to FIG. 7, method 700 can include detecting the nucleotide that was added in step 704 based on the detection of the emission of photons or absence of photons at steps 707, 710, or 713 or a combination thereof (714). For example, without necessarily knowing a priori the identity of the selected nucleotide added in step 704, based upon the detection at step 707 of an absence of photon emission after exposing the nucleotide to the catalyst coupled to fifth moiety at step 705 and the chemiluminogenic molecules at step 706, it can be determined that the nucleotide did not become coupled during step 705 to catalyst 730. Additionally, based upon the detection at step 710 of photon emission after exposing the nucleotide to the catalyst coupled to sixth moiety at step 708 and the chemiluminogenic molecules at step 709, it can be determined that the nucleotide became coupled during step 709 to catalyst 730. Additionally, based upon the detection at step 713 of photons after exposing the nucleotide to the cleaver molecule at step 711 and the chemiluminogenic molecules at step 712, it can be determined that the nucleotide was not cleaved during step 711 from catalyst 730. Based upon these detections, and knowledge of the compatibility of moieties 831, 836, and 891 and the action of cleaver molecule 841 thereupon, it can be determined that the nucleotide is T 890.

Figure 8M:
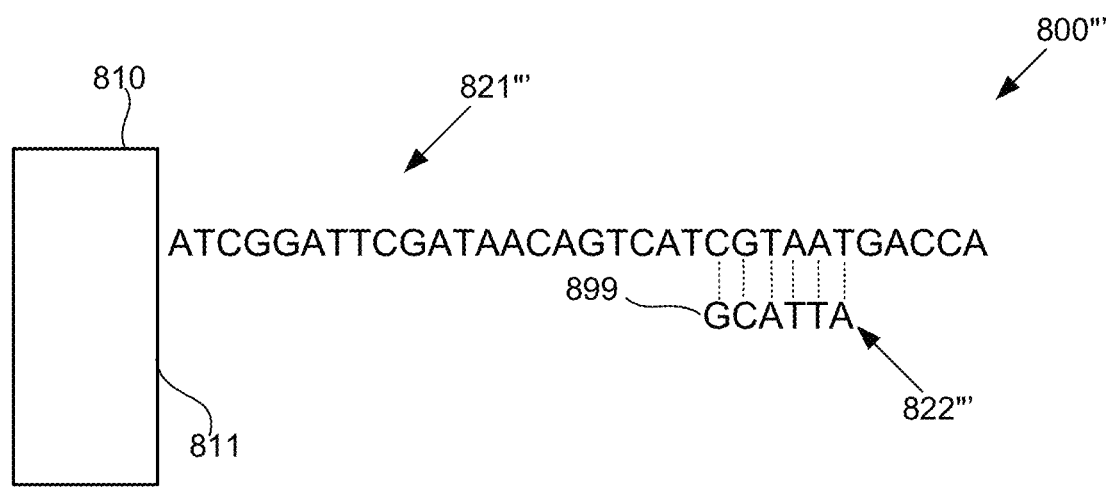

As still another example, in the exemplary alternative composition 800''' illustrated in FIG. 8M, nucleotide G 899 was added to alternative second polynucleotide 822''' based on the sequence of alternative first polynucleotide 821'''.

Referring again to FIG. 7, method 700 includes exposing the nucleotide to a catalyst coupled to a fifth moiety (705), in a manner analogous to that described above with reference to FIGS. 8B and 8F. For example, alternative composition 800''' can be contacted with catalyst 830 coupled to moiety 831 via coupling 832. However, nucleotide G does not include a moiety to which moiety 831 of catalyst 830 can couple, and as such, catalyst 830 does not become coupled to second polynucleotide 822 during step 705. Method 700 illustrated in FIG. 7 also includes exposing the nucleotide to chemiluminogenic molecules (706) and detecting emission of photons or absence of photons from the chemiluminogenic molecules (707), e.g., as described above with reference to FIG. 8C. Because catalyst 830 is not present during step 706, an absence of photons can be detected during step 707 in this example. Method 700 also can include exposing the nucleotide to a catalyst coupled to a sixth moiety (708). For example, in a manner analogous to that described above with reference to FIG. 8D and FIG. 8J, alternative composition 800''' can be contacted with catalyst 830 coupled to moiety 836 via coupling 833. However, nucleotide G does not include a moiety to which moiety 836 of catalyst 830 can couple, and as such, catalyst 830 does not become coupled to second polynucleotide 822 during step 708. Method 700 illustrated in FIG. 7 also includes exposing the nucleotide to chemiluminogenic molecules (709), e.g., in a manner analogous to that described above with reference to step 706. Method 700 illustrated in FIG. 7 also includes detecting emission of photons or absence of photons from the chemiluminogenic molecules (710), e.g., in a manner analogous to that described above with reference to step 707. Because catalyst 830 is not present during step 709, an absence of photons can be detected during step 710 in this example.

Referring still to FIG. 7, method 700 further includes exposing the nucleotide to a cleaver molecule (711) in a manner analogous to that described above with reference to FIGS. 8E and 8L. For example, composition 800''' can be contacted with molecules 841 that can selectively cleave one or more certain catalyst moieties from one or more certain nucleotide moieties. However, because nucleotide G 899 is not coupled to catalyst 830, cleaver molecules 841 substantially have no effect on composition 800'''. Method 700 illustrated in FIG. 7 further can include exposing the nucleotide to chemiluminogenic molecules (712), e.g., in a manner analogous to that described above with reference to step 706. Method 700 illustrated in FIG. 7 also includes detecting emission of photons or absence of photons from the chemiluminogenic molecules (713), e.g., in a manner analogous to that described above with reference to step 707. An absence of photon emission from excited state chemiluminogenic molecules 840', resulting from absence of catalyst 830 during step 712, can be detected in a manner analogous to that described above with reference to steps 706-707.

Referring still to FIG. 7, method 700 can include detecting the nucleotide that was added in step 704 based on the detection of the emission of photons or absence of photons at steps 707, 710, or 713 or a combination thereof (714). For example, without necessarily knowing a priori the identity of the selected nucleotide added in step 704, based upon the detection at step 707 of an absence of photon emission after exposing the nucleotide to the catalyst coupled to fifth moiety at step 705 and the chemiluminogenic molecules at step 706, it can be determined that the nucleotide did not become coupled during step 705 to catalyst 730. Additionally, based upon the detection at step 710 of an absence of photon emission after exposing the nucleotide to the catalyst coupled to sixth moiety at step 708 and the chemiluminogenic molecules at step 709, it can be determined that the nucleotide did not become coupled during step 709 to catalyst 730. Based upon these detections, and knowledge of the absence of a moiety coupled to nucleotide G 899, it can be determined that the nucleotide is G 899.

As illustrated in FIG. 7, steps 703-714 can be repeated any suitable number of times for different nucleotides that are added to the second nucleotide, e.g., based on the sequence of the first nucleotide. In some embodiments, prior to repeating step 703, an additional step can be performed so as to cleave any moieties, couplings, and catalysts from the nucleotide added during the previous implementation of steps 703-714, so that the polymerase with which the composition is contacted readily can add a new nucleotide to the second nucleotide.

Additionally, note that the catalyst(s) to which the nucleotide is exposed during steps 705 and 708 can be, but need not necessarily be, the same as one another. For example, the catalyst to which the nucleotide is exposed during step 705 can include a first catalyst, and the catalyst to which the nucleotide is exposed during step 708 can include a second catalyst that is the same as or different than the first catalyst. Additionally, the chemiluminogenic molecules to which the nucleotide is exposed during steps 706, 709, and 712 can be, but need not necessarily, be, the same as one another. For example, the chemiluminogenic molecules to which the nucleotide is exposed during step 706 can include a first type of chemiluminogenic molecules, the chemiluminogenic molecules to which the nucleotide is exposed during step 709 can include a second type of chemiluminogenic molecules that are the same as or different than the first type of chemiluminogenic molecules, and the chemiluminogenic molecules to which the nucleotide is exposed during step 712 can include a third type of chemiluminogenic molecules that are the same as or different than the first or second types of chemiluminogenic molecules. In one illustrative example, the nucleotide is exposed to a first catalyst at step 705 and first chemiluminogenic molecules at step 706 that interact with the first catalyst, and is exposed to a second catalyst at step 708 and second chemiluminogenic molecules at step 709 that interact with the second catalyst but not with the first catalyst. Other permutations are possible.

Figure 9:
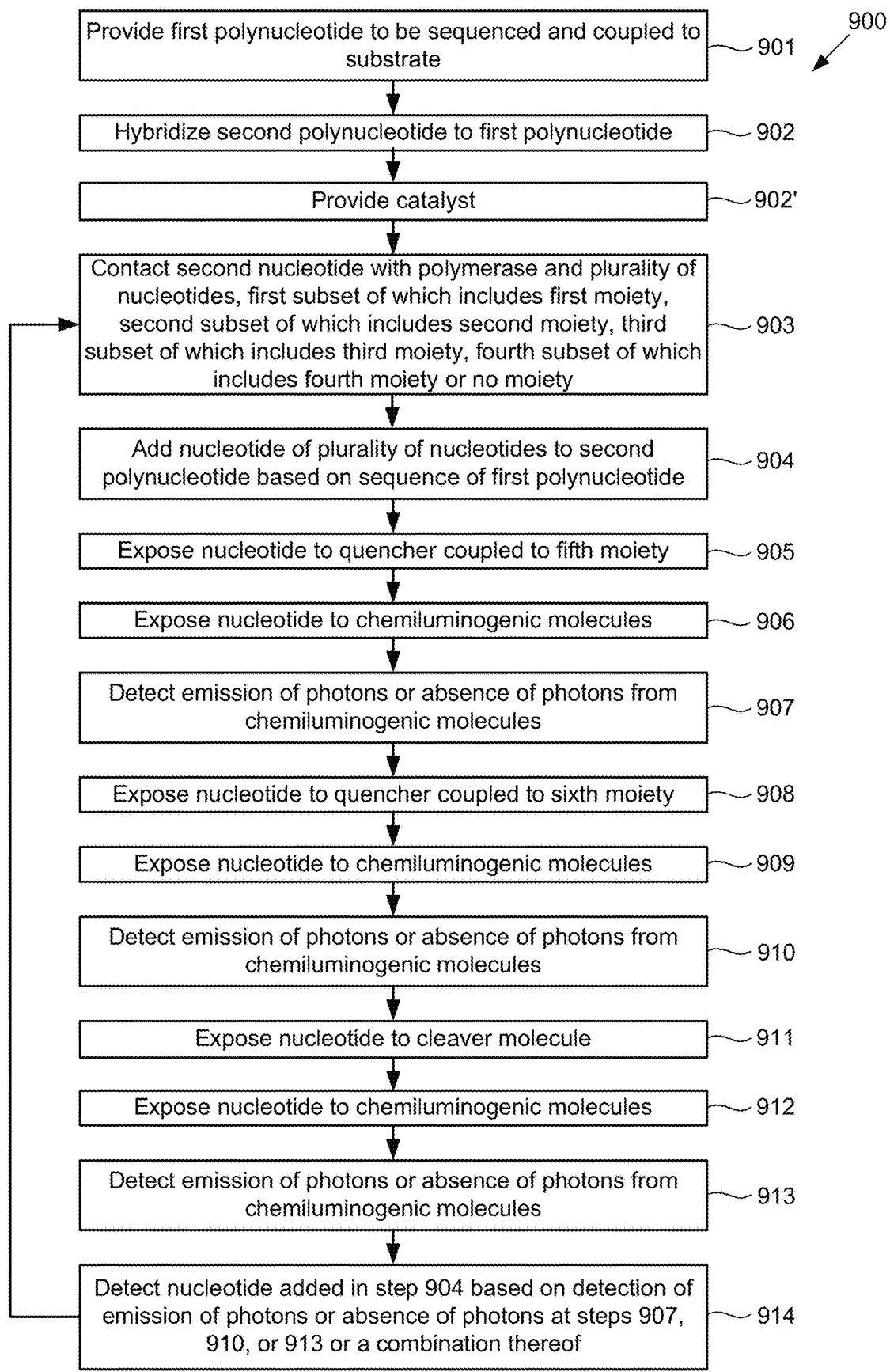
FIG. 9 illustrates an alternative method for detecting the presence of nucleotides using in a polynucleotide using chemiluminescence, according to some embodiments of the present invention.

It should be appreciated that the steps described above with reference to FIG. 7 and FIGS. 8A-8M readily can be adapted so as to include the use of a quencher such as illustrated in FIGS. 6A-6C to inhibit chemiluminescence. FIG. 9 illustrates an alternative method for detecting the presence of nucleotides using in a polynucleotide using chemiluminescence, according to some embodiments of the present invention.

Method 900 illustrated in FIG. 9 includes providing a first polynucleotide to be sequenced and coupled to a substrate (901). For example, first polynucleotide 621 respectively illustrated in compositions 600, 600', or 600" of FIGS. 6A-6C can be coupled to surface 611 of substrate 610 using any suitable coupling provided herein or otherwise known in the art. Method 900 illustrated in FIG. 9 also includes hybridizing a second polynucleotide to the first polynucleotide (902). For example, second polynucleotide 622 illustrated in FIGS. 6A-6C can be hybridized to first polynucleotide 621 using any suitable technique provided herein or otherwise known in the art. Although FIGS. 6A-6C illustrate second polynucleotide 622 as having the sequence ACCATTA hybridized to the sequence TGGTAAT of first polynucleotide 621, it should be appreciated that the first and second polynucleotides can have any suitable respective sequences that hybridize to one another.

Additionally, method 900 illustrated in FIG. 9 includes providing a catalyst coupled sufficiently close to the second polynucleotide that a quencher coupled to the second polynucleotide can inhibit photon emission from chemiluminescent molecules that interact with the catalyst (902'). For example, as illustrated in FIG. 6A, catalyst 630 can be coupled to second polynucleotide 622. As another example, illustrated in FIG. 6B, catalyst 630 can be coupled to first polynucleotide 621. As another example, illustrated in FIG. 6C, catalyst 630 can be coupled to surface 611 of substrate 610. It should be appreciated that catalyst 630 can be coupled to any suitable region of second polynucleotide 622, or to any suitable region of first polynucleotide 621, or any suitable region of surface 611, or otherwise coupled sufficiently close to second polynucleotide 622 that quencher 650 (that can be coupled to second polynucleotide 622 in a subsequent step) can inhibit photon emission from chemiluminescent molecules 640 that interact with catalyst 630.

Referring again to FIG. 9, method 900 further includes contacting the second nucleotide with a polymerase and a plurality of nucleotides (903). A first subset of the plurality of nucleotides can include a first moiety, a second subset of the plurality of nucleotides can include a second moiety, a third subset of the plurality of nucleotides can include a third moiety, and a fourth subset of the plurality of nucleotides can include a fourth moiety or no moiety (903). For example, in a manner analogous to that described above with reference to step 703 of FIG. 7 and FIG. 8A, the composition can be contacted with a polymerase that couples to and binds the first and second polynucleotides in such a manner as to be operable to add a nucleotide to the second polynucleotide based on the sequence of first polynucleotide. The composition also can be contacted with a plurality of nucleotides that can be coupled to one or more different moieties than one another so as to facilitate distinguishing the presence of one particular nucleotide in second polynucleotide from the other nucleotides in that polynucleotide. The moieties to which the nucleotides are coupled, or the couplings therebetween, or both the moieties and the nucleotides, can be selected so as to facilitate identification of the particular nucleotide that has been added to the second polynucleotide, e.g., using a series of steps in which nucleotides coupled to certain moieties are exposed to quencher(s) coupled to certain moieties that can interact with the moieties of only certain subset(s) of the nucleotides or selectively can be cleaved from only certain subset(s) of the nucleotides, in a manner such as provided herein.

As illustrated in FIG. 9, method 900 also includes adding a nucleotide of the plurality of nucleotides to the second polynucleotide based on the sequence of the first polynucleotide (904). For example, in a manner analogous to that described above with reference to step 704 of FIG. 7 and FIGS. 8A and 8B, the polymerase can be operable to add another nucleotide to the second polynucleotide based on the sequence of the first polynucleotide, e.g., adds C to the second polynucleotide based on the G present in the sequence of the first polynucleotide, based on the exemplary sequence of first nucleotide 621 illustrated in FIGS. 6A-6C. In a manner analogous to that illustrated in FIG. 8A, nucleotide C can be coupled to a certain moiety via a certain coupling. After adding nucleotide C to the second polynucleotide, the polymerase can be washed away.

Referring again to FIG. 9, method 900 includes exposing the nucleotide to a quencher coupled to a fifth moiety (905). For example, in a manner analogous to that described above with reference to step 705 of FIG. 7 and FIG. 8B, the composition can be contacted with a quencher coupled to a fifth moiety via a fifth coupling. Depending on the particular moieties to which the nucleotide and quencher are respectively coupled, those moieties may couple to one another. In one illustrative example, the moiety of the quencher can couple to the moiety of nucleotide C, thus coupling the quencher to the second polynucleotide. The moieties of the quencher and the nucleotide respectively can be selected such that if a nucleotide other than C had been added to the second polynucleotide based on the sequence of the first polynucleotide, the moiety of the quencher may not necessarily couple to the moiety of that other nucleotide. Put another way, the moiety of the quencher and the moiety of nucleotide C can be selected so as to couple with one another and to not necessarily couple with one or more other moieties. Additionally, or alternatively, and as described in greater detail herein, the coupling or moiety of the nucleotide C optionally can be selected so as to permit selective cleaving of the quencher from nucleotide C during a subsequent step, which further can facilitate detection of nucleotide C. Excess quencher that did not couple to nucleotide C can be washed away.

Method 900 illustrated in FIG. 9 also includes exposing the nucleotide to chemiluminogenic molecules (906). For example, in a manner analogous to that described above with reference to step 706 of FIG. 7 and FIG. 8C, and also as illustrated in FIGS. 6A-6C, the composition can be contacted with a plurality of chemiluminogenic molecules. The catalyst can suitably interact with a selected chemiluminogenic molecule of the plurality of chemiluminogenic molecules, which can cause that chemiluminogenic molecule to have an excited state. Optionally, one or more reagent molecule(s) (not specifically illustrated) also can be provided that can facilitate interaction between the catalyst and chemiluminogenic molecules so as to cause the chemiluminogenic molecules to emit respective photons in the absence of the quencher. However, although interaction with the catalyst and optional reagent molecule(s) can cause the chemiluminogenic molecules to obtain an excited state, the quencher coupled to the selected nucleotide can inhibit such excited states from emitting a corresponding photon.

Method 900 illustrated in FIG. 9 includes detecting emission of photons or absence of photons from the chemiluminogenic molecules (907). For example, in a manner analogous to that described above with reference to step 707 of FIG. 7 and FIG. 8C, an absence of photon emission from the excited state chemiluminogenic molecules can be detected, e.g., using suitable circuitry configured to detect the photon such as described further below with reference to FIGS. 10A-10B and 11A-11B. In some embodiments, the catalyst interacts with a plurality of chemiluminogenic molecule, and thus would causes the emission of a corresponding plurality of photons in the absence of the quencher, thus increasing the detectability of nucleotide C, such as described further below with reference to FIG. 12. Note that if the nucleotide that had been added to the second polynucleotide had been a nucleotide other than C, and thus was coupled to a moiety other than the first moiety, then the moiety coupled to the quencher may not necessarily have coupled to the first moiety; as such, photons may be emitted during step 905 or detected during step 906 for that nucleotide; such emission of photons also can be detected and used to identify the nucleotide that has been added to the second nucleotide.

Referring again to FIG. 9, method 900 includes exposing the nucleotide to a quencher coupled to a sixth moiety (908). For example, in a manner analogous to that described above with reference to step 708 of FIG. 7 and FIG. 8D, the composition can be contacted with the quencher coupled to a sixth moiety via a sixth coupling. In an illustrative embodiment, because the moiety of nucleotide C is already coupled to moiety of the quencher, or because the moiety of nucleotide C does not couple to the sixth moiety of the quencher, or both, the sixth moiety of the quencher does not become coupled to nucleotide C in this illustrative embodiment. Method 900 illustrated in FIG. 9 also includes exposing the nucleotide to chemiluminogenic molecules (909), e.g., in a manner analogous to that described above with reference to step 906. Method 900 illustrated in FIG. 9 also includes detecting emission of photons or absence of photons from the chemiluminogenic molecules (910), e.g., in a manner analogous to that described above with reference to step 907. Note that because nucleotide C remains coupled to the quencher via the first and fifth moieties during steps 908-710, an absence of photon emission from the excited state chemiluminogenic molecules can be detected in a manner analogous to that described above with reference to steps 906-707.

Referring again to FIG. 9, method 900 further includes exposing the nucleotide to a cleaver molecule (911). For example, in a manner analogous to that described above with reference to step 711 of FIG. 7 and FIG. 8E, the composition can be contacted with molecules that can selectively cleave one or more certain quencher moieties from one or more certain nucleotide moieties, but, in this illustrative embodiment, substantially does not cleave the fifth moiety of the quencher from the first moiety of nucleotide C. Method 900 illustrated in FIG. 9 further can include exposing the nucleotide to chemiluminogenic molecules (912), e.g., in a manner analogous to that described above with reference to step 906. Method 900 illustrated in FIG. 9 also includes detecting emission of photons or absence of photons from the chemiluminogenic molecules (913), e.g., in a manner analogous to that described above with reference to step 907.

Referring still to FIG. 9, method 900 can include detecting the nucleotide that was added in step 904 based on the detection of the emission of photons or absence of photons at steps 907, 910, or 913 or a combination thereof (914). For example, without necessarily knowing a priori the identity of the selected nucleotide added in step 904, based upon the detection at step 907 of an absence of photon emission after exposing the nucleotide to the quencher coupled to fifth moiety at step 905 and the chemiluminogenic molecules at step 906, it can be determined that the nucleotide became coupled during step 905 to the quencher. Additionally, based upon the detection at step 913 of an absence of photon emission after exposing the nucleotide to the cleaver molecule at step 911 and the chemiluminogenic molecules at step 912, it can be determined that the nucleotide remained coupled during step 911 to the quencher. Based upon these detections, and knowledge of the compatibility of the respective moieties to which the nucleotide and quencher are coupled and the action of the cleaver molecule thereupon, it can be determined that the nucleotide is C.

It should be appreciated that for any given sequence of the first polynucleotide, it is approximately as likely that the polymerase added G, T, A, or C to the second polynucleotide during step 904. Steps 905-714 analogously can be used so as to detect nucleotides other than C, in a manner such as described above with reference to FIGS. 8F-8M.

Additionally, note that the quencher(s) to which the nucleotide is exposed during steps 905 and 908 can be, but need not necessarily be, the same as one another. For example, the quencher to which the nucleotide is exposed during step 905 can include a first quencher, and the quencher to which the nucleotide is exposed during step 908 can include a second quencher that is the same as or different than the first quencher. Additionally, the chemiluminogenic molecules to which the nucleotide is exposed during steps 906, 909, and 912 can be, but need not necessarily be, the same as one another. For example, the chemiluminogenic molecules to which the nucleotide is exposed during step 906 can include a first type of chemiluminogenic molecules, the chemiluminogenic molecules to which the nucleotide is exposed during step 909 can include a second type of chemiluminogenic molecules that are the same as or different than the first type of chemiluminogenic molecules, and the chemiluminogenic molecules to which the nucleotide is exposed during step 912 can include a third type of chemiluminogenic molecules that are the same as or different than the first or second types of chemiluminogenic molecules. In one illustrative example, the nucleotide is exposed to a first quencher at step 905 and first chemiluminogenic molecules at step 706 that interact with the first quencher, and is exposed to a second quencher at step 708 and second chemiluminogenic molecules at step 909 that interact with the second quencher but not with the first quencher. Other permutations are possible.

Exemplary Systems

Exemplary systems for detecting the presence of polymer subunits now will be described with reference to FIGS. 10A-10B and 11A-11B.

Figure 10A:
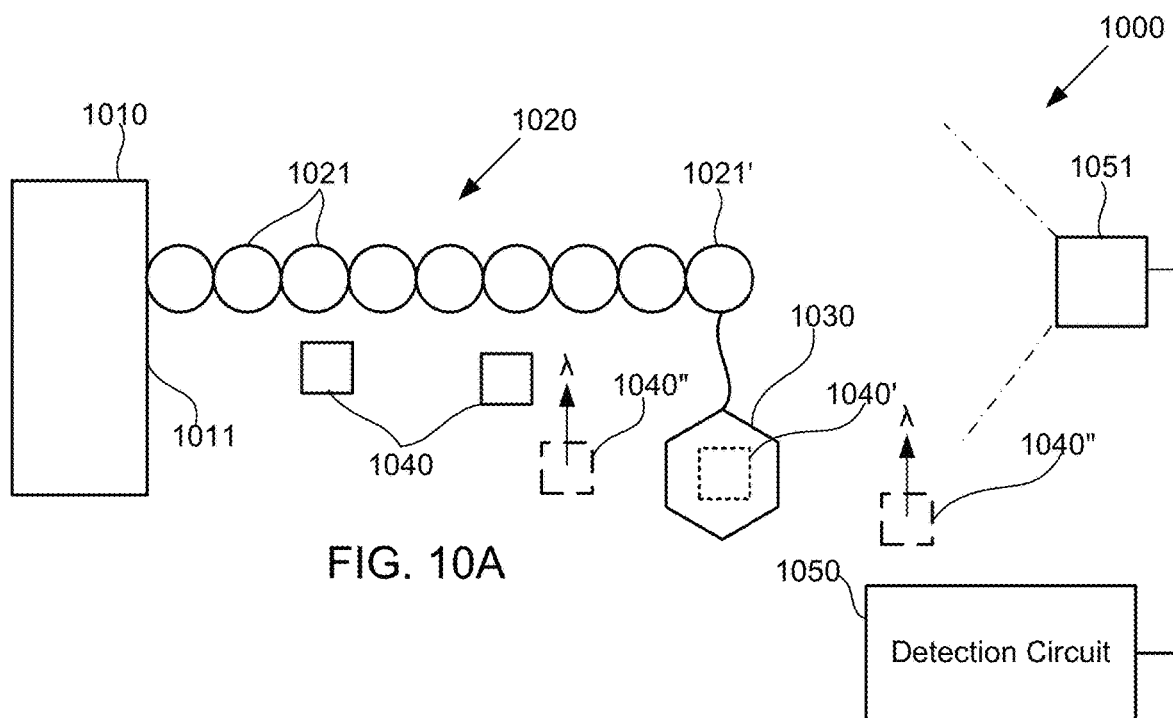
FIGS. 10A-10B schematically illustrate systems including detection circuitry configured to detect the presence of polymer subunits using chemiluminescence, according to some embodiments of the present invention.
Figure 10B:
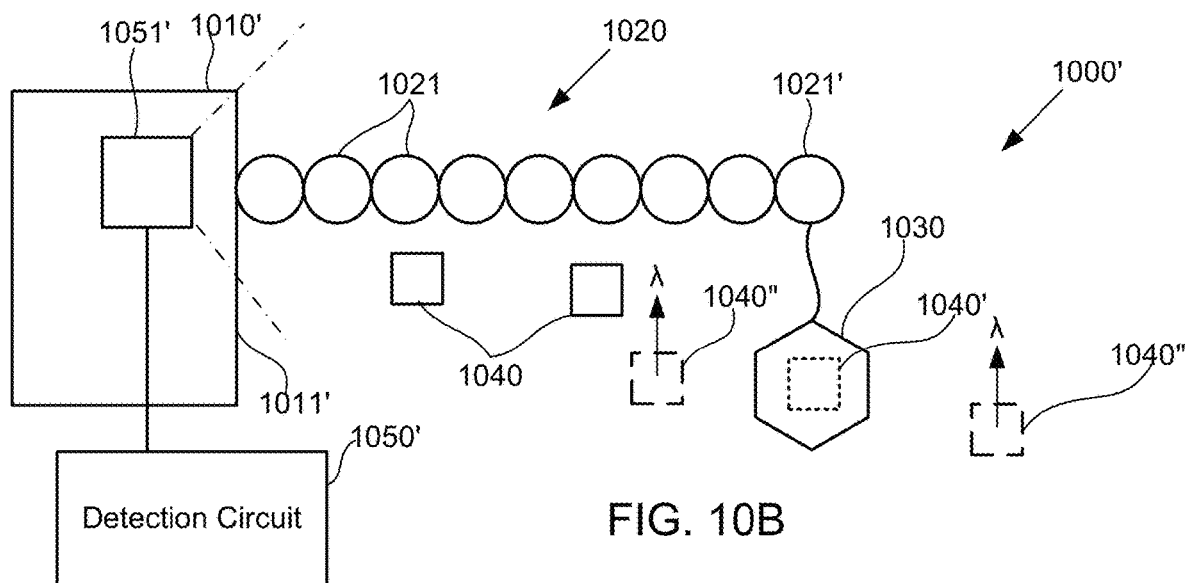

FIGS. 10A-10B schematically illustrate systems including detection circuitry configured to detect the presence of polymer subunits using chemiluminescence, according to some embodiments of the present invention. System 1000 illustrated in FIG. 10A includes substrate 1010, polymer 1020 including a plurality of subunits 1021 and coupled to surface 1011 of substrate 1010, catalyst 1030 coupled to selected subunit 1021', and circuitry configured to detect photons emitted by chemiluminogenic molecules 1040 with which system 1000 can be contacted. In the illustrated embodiment, the circuitry includes detection circuit 1050, and optical detector 1051 disposed at a spaced distance from substrate 1010. Optical detector 1051 is configured to generate an electrical signal based on the emission of photons or absence of photons within the field of view of optical detector 1051, schematically illustrated in FIG. 10A using the dash-dot lines, and to provide such an electrical signal to detection circuit 1050 for analysis. For example, detection circuit 1050 can be configured to detect the presence of subunit 1021' of polymer 1020 based on detection of photons (or absence thereof) emitted by excited state chemiluminogenic molecules 1040' as they decay to ground state molecules 1040" with photon emission, represented by the arrow and λ.

Optical detector 1051 can include any suitable device configured to generate an electrical or fiber-optic based signal based on photons received (or not received) by the device. As one example, optical detector 1051 can include an active-pixel sensor (APS) including an array of amplified photodetectors configured to generate an electrical signal based on photons received by the photodetectors. APSs can be based on complementary metal oxide semiconductor (CMOS) technology known in the art. CMOS-based detectors can include field effect transistors (FETs), e.g., metal oxide semiconductor field effect transistors (MOSFETs). In particular embodiments, a CMOS imager having a single-photon avalanche diode (CMOS-SPAD) can be used, for example, to distinguish fluorophores using fluorescence lifetime imaging (FLIM). Exemplary CMOS based systems are described in US 2008/0037008 A1; Giraud et al., Biomedical Optics Express 1: 1302-1308 (2010); and Stoppa et al., IEEE European Solid-State Device Conference (ESS-CIRC), Athens, Greece, IEEE, pp. 204-207 (2009), each of which is incorporated herein by reference in its entirety. Other useful detection devices that can be used include, for example, those described in U.S. Pat. No. 7,329,860 and US 2010/0111768 A1, each of which is incorporated herein by reference in its entirety.

As another example, optical detector 1051 can include a photodiode, such as an avalanche photodiode. As yet another example, optical detector 1051 can include a charge-coupled device (CCD). As yet another example, optical detector 1051 can include a cryogenic photon detector. As yet another example, optical detector 1051 can include a reverse-biased light emitting diode (LED). As yet another example, optical detector 1051 can include a photoresistor. As yet another example, optical detector 1051 can include a phototransistor. As yet another example, optical detector 1051 can include a photovoltaic cell. As yet another example, optical detector 1051 can include a photomultiplier tube. As yet another example, optical detector 1051 can include a quantum dot photoconductor or photodiode. Any other suitable device configured to generate an electrical signal based on photons received (or not received) can be included in optical detector 1051.

Detection circuit 1050 can include any suitable combination of hardware and software in operable communication with optical detector 1051 so as to receive the electrical or fiber-optic based signal therefrom, and configured to detect subunit 1021' of polymer 1020 based on such signal, e.g., based on optical detector 1051 detecting one or more photons from excited chemiluminescent molecules 1040'. For example, detection circuit 1050 can include a memory and a processor coupled to the memory (not specifically illustrated). The memory also can store data regarding couplings between polymer subunits and catalysts, e.g., data indicating that photons can be expected to be emitted if subunit 121' is present. The memory can store instructions for causing the processor to receive the signal from optical detector 1051 and to detect the subunit 1021' based thereon. For example, the instructions can cause the processor to determine, based on the signal from optical detector 1051, that photons are being emitted within the field of view of optical detector 1051; to determine, based on the data, that photons can be expected to be emitted if subunit 1021' is present; and to determine, based on both of these determinations, that subunit 1021' is present.

More complex instructions and data also can be included in the memory of detection circuit. For example, in embodiments such as described above with reference to FIGS. 7-9, in which the polymer includes a second polynucleotide that is hybridized to a first polynucleotide to be sequenced, the memory of detection circuit 1050 can store instructions causing the processor to appropriately control or otherwise monitor the exposure of the second nucleotide to nucleotides, catalysts, quenchers, chemiluminogenic molecules, or cleaver molecules or any combination thereof at appropriate steps during method 700 illustrated in FIG. 7 or during method 900 illustrated in FIG. 9. For example, the processor can be in operable communication with one or more dispensers for nucleotides, catalysts, quenchers, chemiluminogenic molecules, or cleaver molecules so as to control or monitor a timing or amount of exposure of the second nucleotide to such nucleotides, catalysts, quenchers, chemiluminogenic molecules, or cleaver molecules. The memory also can store data regarding couplings between different nucleotides and catalysts or quenchers, and data indicating that photons can be expected to be emitted or absent following exposure to such catalysts or quenchers or following exposure to cleaver molecules, if a particular nucleotide is present.

Alternative system 1000' illustrated in FIG. 10B includes alternative substrate 1010', polymer 1020 including a plurality of subunits 1021 and coupled to surface 1011' of substrate 1010', catalyst 1030 coupled to selected subunit 1021', and alternative circuitry configured to detect photons emitted by chemiluminogenic molecules 1040 with which system 1000 can be contacted. In the illustrated embodiment, the alternative circuitry includes alternative detection circuit 1050', and alternative optical detector 1051' disposed within alternative substrate 1010'. Alternative optical detector 1051' is configured to generate an electrical signal based on the emission of photons or absence of photons within the field of view of optical detector 1051', schematically illustrated in FIG. 10B using the dash-dot lines, and to provide such an electrical signal to detection circuit 1050' for analysis. For example, detection circuit 1050' can be configured to detect the presence of subunit 1021' of polymer 1020 based on detection of photons (or absence thereof) emitted by excited state chemiluminogenic molecules 1040' as they decay to ground state molecules 1040" with photon emission, represented by the arrow and k.

Alternative detection circuit 1050' and alternative optical detector 1051' respectively can be configured substantially analogously as detection circuit 1050 and optical detector 1051 described above with reference to FIG. 10A. In one illustrative embodiment, optical detector 1051' can include an active-pixel sensor (APS) including an array of amplified photodetectors configured to generate an electrical signal based on photons received by the photodetectors. APSs can be based on complementary metal oxide semiconductor (CMOS) technology known in the art. CMOS-based detectors can include field effect transistors (FETs), e.g., metal oxide semiconductor field effect transistors (MOSFETs). In another illustrative embodiment, optical detector 1051' can include a CCD.

It should be appreciated that systems 1000 and 1000' readily can be adapted for use with quenchers, e.g., such as described above with reference to FIGS. 3, 4, 6A-6B, and 9. Additionally, it should be appreciated that systems 1000 and 1000' suitably can be modified so as to detect subunits of a plurality of polymers using chemiluminescence in parallel with one another. For example, FIGS. 11A-11B schematically illustrate systems including detection circuitry configured to detect the presence of polymer subunits in arrays of polymers using chemiluminescence, according to some embodiments of the present invention.

Figure 11A:
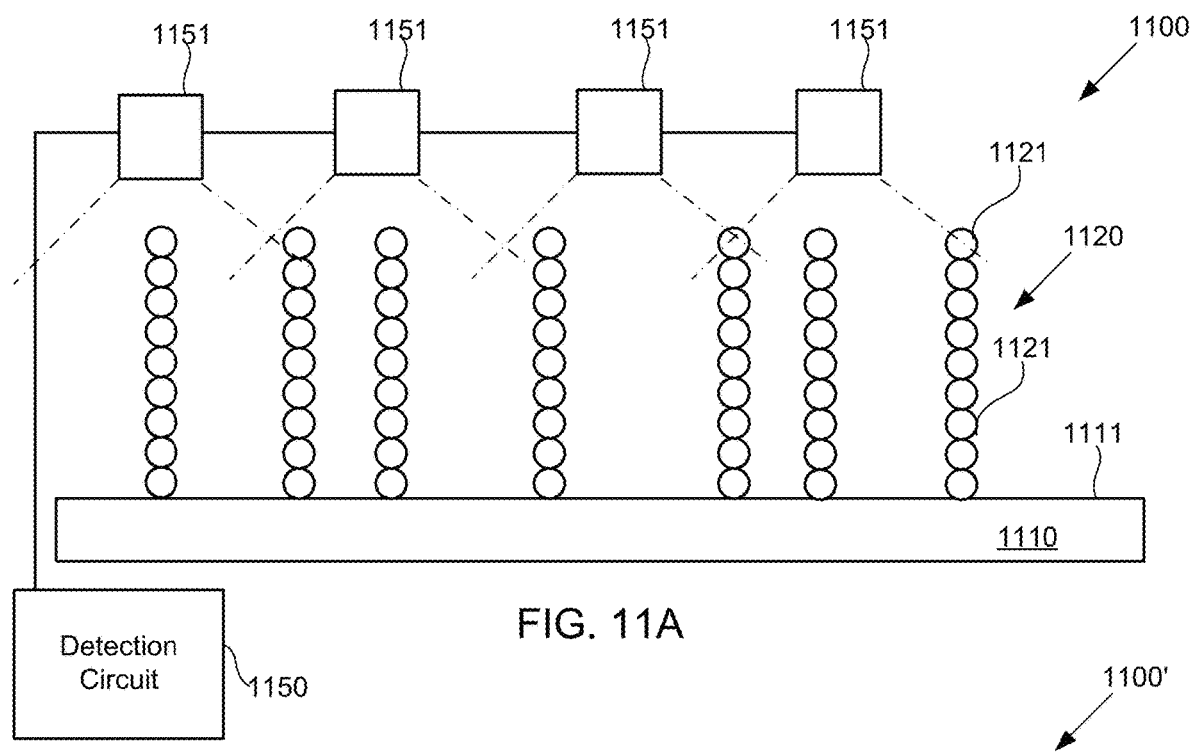
FIGS. 11A-11B schematically illustrate systems including detection circuitry configured to detect the presence of polymer subunits in arrays of polymers using chemiluminescence, according to some embodiments of the present invention.

System 1100 illustrated in FIG. 11A includes substrate 1110, a plurality of polymers 1120 that each can include a respective subunit 1121 and coupled to surface 1111 of substrate 1110, a catalyst (not specifically illustrated) coupled to selected subunit 1121, and circuitry configured to detect photons emitted by chemiluminogenic molecules (not specifically illustrated) with which system 1100 can be contacted. In the illustrated embodiment, the circuitry includes detection circuit 1150, and a plurality of optical detectors 1151 disposed at a spaced distance from substrate 1110 and in operable communication with detection circuit 1150. Optical detectors 1151 each are configured to generate an electrical signal based on the emission of photons or absence of photons within the field of view of that optical detector 1151, schematically illustrated in FIG. 11A using the dash-dot lines, and to provide such an electrical signal to detection circuit 1150 for analysis. For example, detection circuit 1150 can be configured to detect the presence of subunit 1121 of each polymer 1120 based on detection of photons (or absence thereof) emitted by excited state chemiluminogenic molecules (not specifically illustrated) as they decay to ground state molecules with photon emission. Detection circuit 1150 and optical detectors 1151 respectively can be configured substantially analogously as detection circuit 1050 and optical detector 1051 described above with reference to FIG. 10A. The memory of detection circuit 1150 can include instructions causing the processor of detection circuit 1150 to receive a respective signal from each optical detector 1151 and to detect the presence of subunit 1121 in each polymer 1120.

Note that any suitable number of optical detectors 1151 can be provided so as to facilitate detecting subunits of polymers 1120 illustrated in FIG. 11A. For example, in some embodiments, a plurality of optical detectors 1151 can be included, each corresponding to a respective polymer 1120. In other embodiments, a plurality of optical detectors 1151 can be included, each corresponding to a plurality of polymers 1120. For example, as illustrated in FIG. 11A, one or more of optical detectors 1151 can include a plurality of polymers 1120 within its field of view. In still other embodiments, a single optical detector 1151 can be included, that includes each of polymers 1120 within its field of view.

Figure 11B:
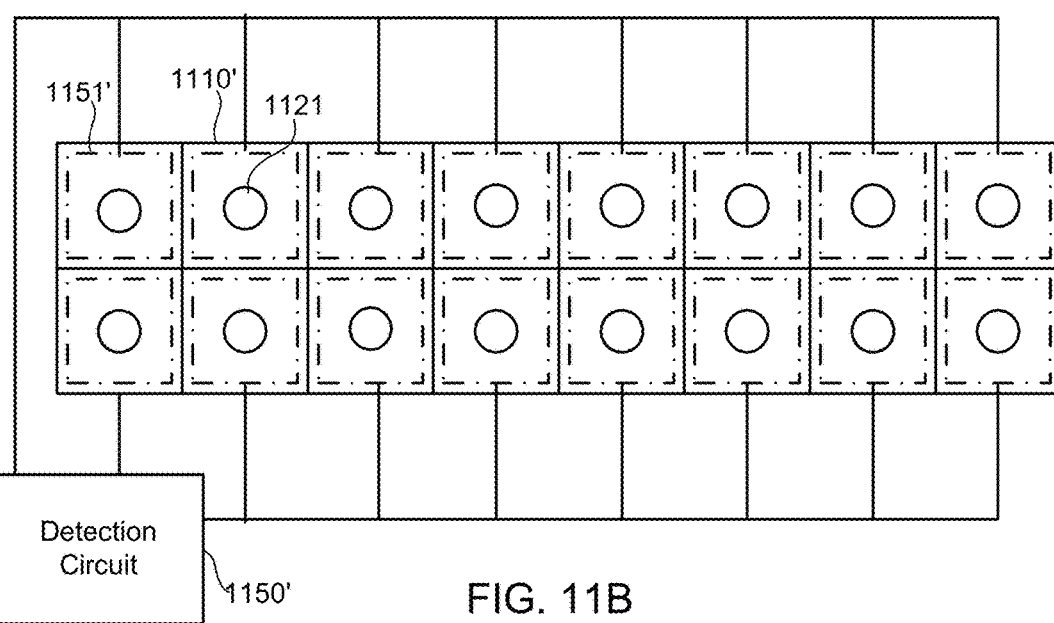

Alternative system 1100' illustrated in FIG. 11B includes substrate 1110', a plurality of polymers (not specifically illustrated) that each can include a respective subunit 1121 and coupled to the surface of alternative substrate 1110', a catalyst (not specifically illustrated) coupled to selected subunit 1121, and circuitry configured to detect photons emitted by chemiluminogenic molecules (not specifically illustrated) with which system 1100' can be contacted. In the illustrated embodiment, the circuitry includes detection circuit 1150', and a plurality of optical detectors 1151' disposed within substrate 1110' and in operable communication with detection circuit 1150'. Optical detectors 1151' each are configured to generate an electrical signal based on the emission of photons or absence of photons within the field of view of that optical detector 1151', schematically illustrated in FIG. 11B using the dash-dot lines, and to provide such an electrical signal to detection circuit 1150' for analysis. For example, detection circuit 1150' can be configured to detect the presence of subunit 1121 of each polymer based on detection of photons (or absence thereof) emitted by excited state chemiluminogenic molecules (not specifically illustrated) as they decay to ground state molecules with photon emission. Detection circuit 1150' and optical detectors 1151' respectively can be configured substantially analogously as detection circuit 1050' and optical detector 1051' described above with reference to FIG. 10B. In one illustrative embodiment, each optical detector 1151' can include an active-pixel sensor (APS) including an array of amplified photodetectors configured to generate an electrical signal based on photons received by the photodetectors. APSs can be based on complementary metal oxide semiconductor (CMOS) technology known in the art. CMOS-based detectors can include field effect transistors (FETs), e.g., metal oxide semiconductor field effect transistors (MOSFETs). In another illustrative embodiment, each optical detector 1151' can include a CCD. The memory of detection circuit 1150' can include instructions causing the processor of detection circuit 1150' to receive a respective signal from each optical detector 1151' and to detect the presence of subunit 1121 in each polymer.

Note that any suitable number of optical detectors 1151' can be provided so as to facilitate detecting subunits 1121 of the polymers illustrated in FIG. 11B. For example, as illustrated in FIG. 11B, in some embodiments, a plurality of optical detectors 1151' can be included, each corresponding to a respective polymer. In other embodiments, a plurality of optical detectors 1151' can be included, each corresponding to a plurality of polymers. Or, for example, one or more of optical detectors 1151' can include a plurality of polymers within its field of view. In still other embodiments, a single optical detector 1151' can be included, that includes each of polymers within its field of view. Additionally, it should be appreciated that systems 1100 and 1100' readily can be adapted for use with quenchers, e.g., such as described above with reference to FIGS. 3, 4, 6A-6B, and 9.

In one illustrative embodiment, optical detector 1151' can include an active-pixel sensor (APS) including an array of amplified photodetectors configured to generate an electrical signal based on photons received by the photodetectors. APSs can be based on complementary metal oxide semiconductor (CMOS) technology known in the art. CMOS-based detectors can include field effect transistors (FETs), e.g., metal oxide semiconductor field effect transistors (MOSFETs). In another illustrative embodiment, optical detector 1051' can include a CCD.

Exemplary Lifetime and Catalytic Effects

Note that the respective lifetimes of the excited state chemiluminogenic molecules can affect whether those molecules are within the field of view of an appropriate optical detector, e.g., detector 1051, 1051', 1151, or 1151' respectively illustrated in FIG. 10A, 10B, 11A, or 11B. For example, if the lifetime is relatively long, then the excited state molecules can be transported (e.g., by diffusion or by directional flow) out of the field of view of the optical detector before emitting a photon. In some embodiments, the field of view of the optical detector and the chemiluminogenic molecules are co-selected such that the respective lifetimes of the excited state chemiluminogenic molecules are sufficiently short so as to emit photons substantially within the field of view of an appropriate optical detector. In one nonlimiting, illustrative embodiment, the chemiluminogenic molecule is selected so as to have an excited state lifetime on the order of µs, resulting in a spatial extent of emission of approximately 500 nm or less under room-temperature diffusion conditions. For example, luminol can be expected to have an excited state lifetime resulting in a spatial extent of emission of approximately 200-400 nm under room-temperature diffusion conditions.

Additionally, as mentioned further above, the catalysts provided herein can interact with a plurality of chemiluminogenic molecules (which also may be referred to as emitters), thus causing the emission of a corresponding plurality of photons, and thus increasing the detectability of a polymer subunit. The signal to noise (S/N) ratio, or SNR, of a signal such as may be generated by an appropriate optical detector, e.g., detector 1051, 1051', 1151, or 1151', can be expressed as follows:

$$SNR = \frac{N(t/\tau)Q_r Q_c Q_e}{\sqrt{N(t/\tau)(1+X)Q_r Q_c Q_e + Dt + N_r^2}}$$

where N is the number of identical (clonal) polynucleotides to which a selected nucleotide is being added; t is integration time of the optical sensor (which also can be referred to as data acquisition time); τ is the turnover time of the catalyst (which also can be referred to as the inverse of the turnover rate of the catalyst, and has units of time); the ratio t/τ can be referred to as the emitter turnover, e.g., how many times the catalyst turns over during the integration time; $Q_r$ is reaction efficiency of the catalytic reaction, e.g., the fraction of catalytic interactions between the catalyst and chemiluminogenic molecule that cause emission of a photon; $Q_c$ is the collection efficiency of the optical sensor, e.g., the fraction of emitted photons that are captured by the optical sensor; $Q_e$ is the so-called quantum efficiency of the optical sensor, e.g., the fraction of photons received by the sensor that produce an electrical signal; X is the cross-talk between optical sensors, e.g., the fraction of photons that were received by an unintended optical sensor; D is the dark current of the optical sensor; and $N_r$ is the readout noise (electronic noise) of the optical sensor.

Figure 12:
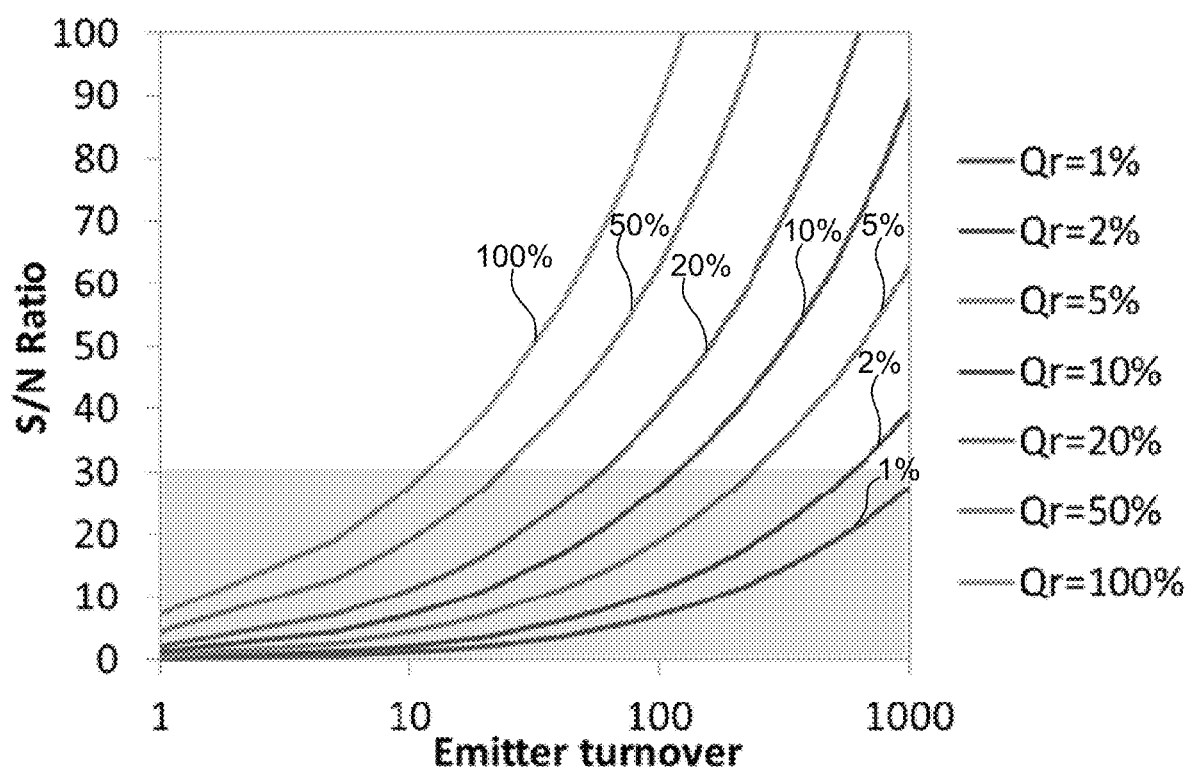
FIG. 12 illustrates a plot of calculated signal-to-noise (S/N) ratio as a function of turnover for chemiluminogenic molecules having different quantum efficiencies than one another, according to some embodiments of the present invention.

FIG. 12 illustrates a plot of calculated S/N ratio as a function of turnover for chemiluminogenic molecules (emitters) having different quantum efficiencies than one another, according to some embodiments of the present invention. The S/N ratios illustrated in FIG. 12 were based on an assumption of N=1000, t=1 second, $Q_c$=30%, $Q_e$=40%, X=50%, $N_r$=5 electrons/second, D=15 electrons/second, and $Q_r$=1%, 2%, 5%, 10%, 20%, 50%, or 100%. The value of τ was varied between 1 second and 0.001 second such that the emitter turnover (the ratio t/τ, corresponding to the x-axis of FIG. 12) varied between 1 and 1000. So as to achieve a S/N ratio of approximately 30 or greater in a single frame (single signal), it can be understood from FIG. 12 that at least 1% reaction efficiency (Qr) with a catalytic turnover time τ of approximately 1.0 ms or less can be useful.

Additionally, it can be understood from FIG. 12 that even for chemiluminogenic molecules having a reaction efficiency (Qr) of 100%, an emitter turnover of greater than 10 can be useful for achieving a S/N ratio of approximately 30 or greater in a single frame (single signal). However, it should be appreciated that other S/N ratios suitably can be used. In one nonlimiting example, a S/N ratio of approximately 5 or greater suitably can be used. In another nonlimiting example, a S/N ratio of approximately 10 or greater suitably can be used. In another nonlimiting example, a S/N ratio of approximately 15 or greater suitably can be used. In another nonlimiting example, a S/N ratio of approximately 20 or greater suitably can be used. In another nonlimiting example, a S/N ratio of approximately 25 or greater suitably can be used. In another nonlimiting example, a S/N ratio of approximately 30 or greater suitably can be used. In another nonlimiting example, a S/N ratio of approximately 35 or greater suitably can be used. In another nonlimiting example, a S/N ratio of approximately 40 or greater suitably can be used. In another nonlimiting example, a S/N ratio of approximately 45 or greater suitably can be used. In another nonlimiting example, a S/N ratio of approximately 50 or greater suitably can be used.

EXAMPLES

Some exemplary results obtained using different catalysts and chemiluminogenic molecules with polynucleotides now will be described with reference to FIGS. 13A-15.

In one example, FIGS. 13A-13E illustrate images obtained during an illustrative method of detecting the presence of nucleotides in a polynucleotide using chemiluminescence, according to one exemplary embodiment of the present invention. A plurality of polynucleotides were coupled to a substrate surface, wherein at least some of the polynucleotides included different sequences than one another. A second polynucleotide was hybridized to each of the polynucleotide coupled to the substrate surface. The polynucleotides then were contacted with a polymerase and with a solution including nucleotides A, G, T, and C. Of these, only nucleotide C was coupled to a biotin moiety. Depending on the sequence of the particular polynucleotide coupled to the substrate surface, either A, G, T, or C was added to the polynucleotide hybridized to that particular polynucleotide, in a manner analogous to that described above with reference to steps 701-704 of method 700 illustrated in FIG. 7. The polymerase and unreacted nucleotides were washed away, and the polynucleotides then were exposed to a solution including horseradish peroxidase (HRP) coupled to a streptavidin moiety in a manner analogous to that described above with reference to step 705 of method 700 illustrated in FIG. 7. For polynucleotides to which nucleotide C had been added, the biotin moiety of that nucleotide C coupled to the streptavidin moiety of HRP, thus coupling the HRP to that nucleotide C. Excess HRP then was washed away. The polynucleotides then were exposed to chemiluminogenic molecule luminol in a manner analogous to that described above with reference to step 706 of method 700 illustrated in FIG. 7.

Subsequently, the HRP was cleaved from nucleotide C, the cleaved HRP and luminol were washed away, and the polynucleotides then again were contacted with a polymerase and with a solution including nucleotides A, G, T, and C, again with only nucleotide C was coupled to a biotin moiety. Depending on the sequence of the particular polynucleotide coupled to the substrate surface, either A, G, T, or C was added to the polynucleotide hybridized to that particular polynucleotide. Because the sequences of the various polynucleotides were different than each other, nucleotide C may have been added to different polynucleotides than in the previous cycle. The polymerase and unreacted nucleotides were washed away, and the polynucleotides then were exposed to a solution including horseradish peroxidase (HRP) coupled to a streptavidin moiety in a manner analogous to that described above with reference to step 705 of method 700 illustrated in FIG. 7. For polynucleotides to which nucleotide C had been added, the biotin moiety of that nucleotide C coupled to the streptavidin moiety of HRP, thus coupling the HRP to that nucleotide C. Excess HRP then was washed away. The polynucleotides then were exposed to chemiluminogenic molecule luminol in a manner analogous to that described above with reference to step 706 of method 700 illustrated in FIG. 7. Such cycles of adding nucleotides, coupling nucleotide C to HRP, and exposing the polynucleotides to luminol were repeated multiple times.

Figure 13A:
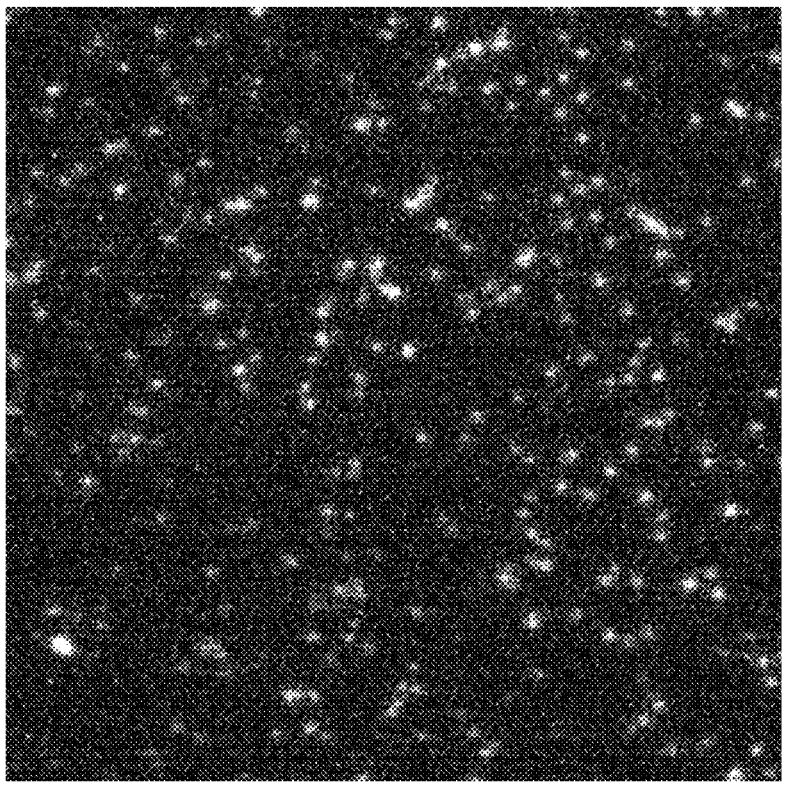
FIGS. 13A-13E illustrate images obtained during an illustrative method of detecting the presence of nucleotides in a polynucleotide using chemiluminescence, according to one exemplary embodiment of the present invention.
Figure 13B:
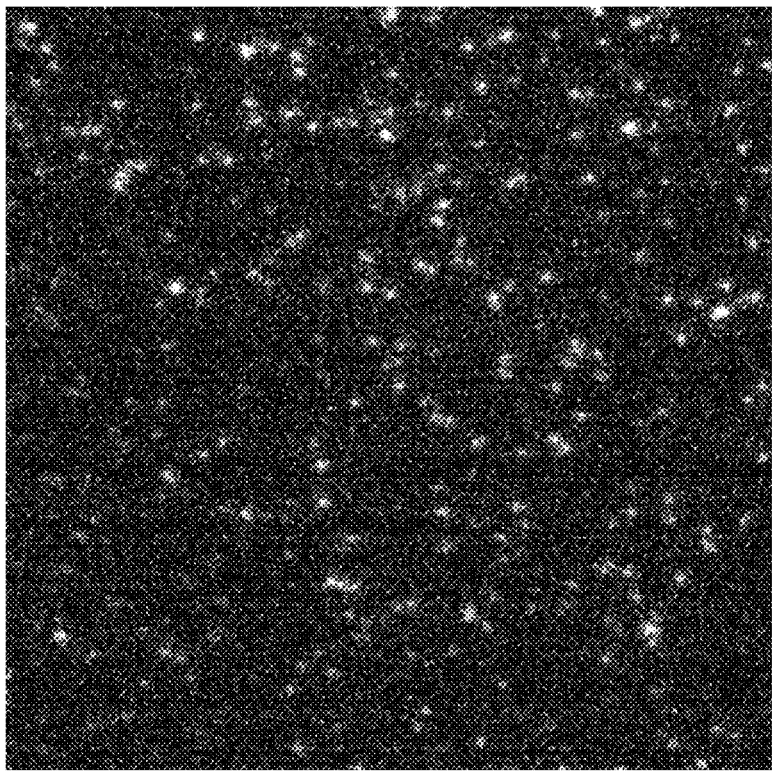

The images illustrated in FIGS. 13A-13E were obtained using a CCD camera disposed at a spaced distance from the substrate in a manner analogous to that described above with reference to FIGS. 10A and 11A. The CCD camera detected photons emitted resulting from interactions between the luminol and the HRP in a manner analogous to that described above with reference to step 707 illustrated in FIG. 7. The gain of the CCD camera was equal to 10, and the integration time t for each image was approximately 1 second. The image illustrated in FIG. 13A corresponds to a first cycle such as described above. As such, the bright spots in FIG. 13A correspond to locations at which a nucleotide C was added to the polynucleotide that was hybridized to another polynucleotide coupled to the substrate surface, that is, for polynucleotides coupled to the substrate surface for which the next nucleotide in the sequence was G. The image illustrated in FIG. 13B corresponds to a second cycle such as described above. As such, the bright spots in FIG. 13B correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 13B are in different locations than the bright spots in FIG. 13A.

Figure 13C:
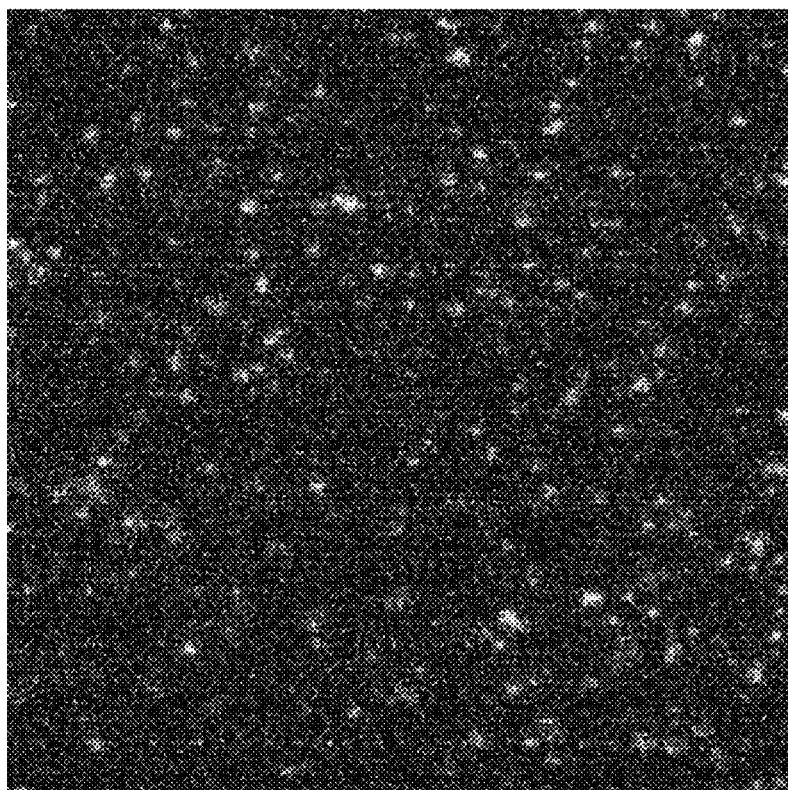
Figure 13D:
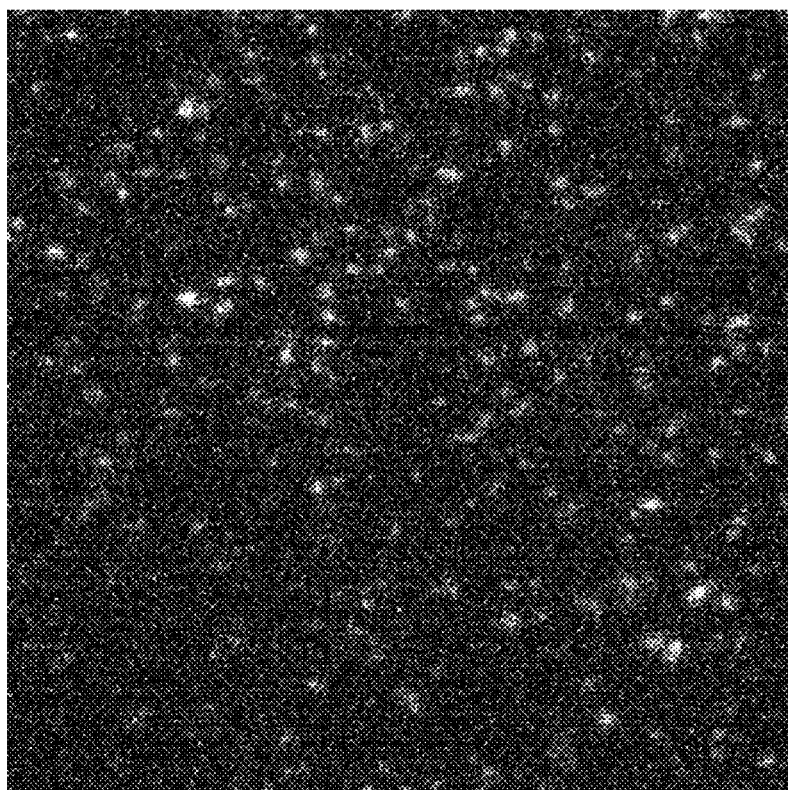

The image illustrated in FIG. 13C corresponds to a third cycle such as described above. As such, the bright spots in FIG. 13C correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 13C are in different locations than the bright spots in FIG. 13A or FIG. 13B. The image illustrated in FIG. 13D corresponds to a fourth cycle such as described above. As such, the bright spots in FIG. 13D correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 13D are in different locations than the bright spots in FIG. 13A, 13B, or 13C.

Figure 13E:
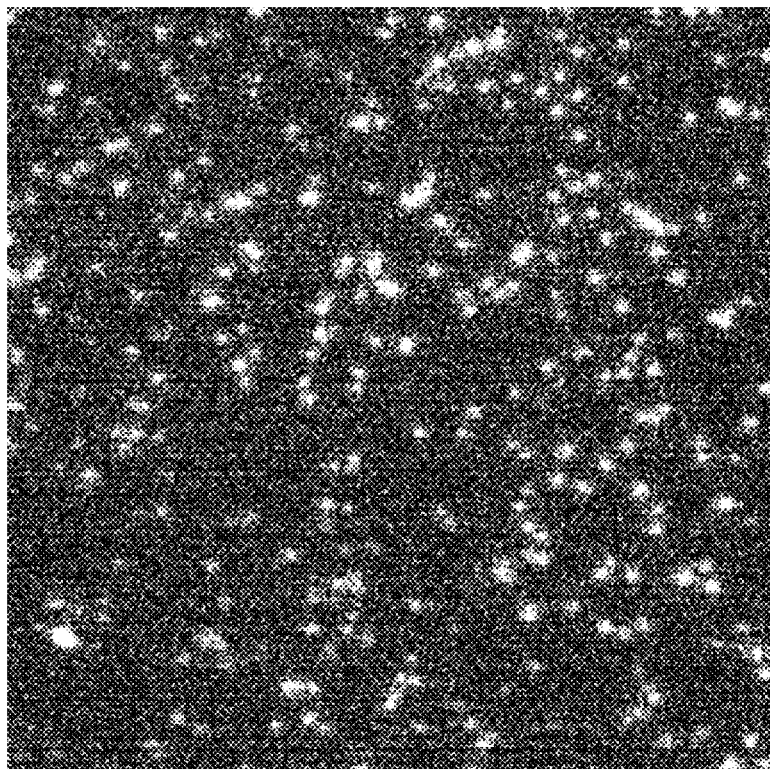

The image illustrated in FIG. 13E corresponds to a "reset" cycle following the first, second, third, and fourth cycles. During the "reset" cycle, polynucleotides that were hybridized to the polynucleotide coupled to the substrate surface were washed away, and a first cycle such as described above subsequently performed. As such, the bright spots in FIG. 13E correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the sequences of the various polynucleotides coupled to the substrate surface remained constant between the first through fourth cycles and the reset cycle, it would be expected that the bright spots resulting from the reset cycle would be in approximately the same location as in FIG. 13A, which appears to be the case.

In another example, FIGS. 14A-14E illustrate images obtained during another illustrative method of detecting the presence of nucleotides in a polynucleotide using chemiluminescence, according to one exemplary embodiment of the present invention. A plurality of polynucleotides were coupled to a substrate surface, wherein at least some of the polynucleotides included different sequences than one another. A second polynucleotide was hybridized to each of the polynucleotides coupled to the substrate surface. The polynucleotides then were contacted with a polymerase and with a solution including nucleotides A, G, T, and C. Of these, only nucleotide C was coupled to a biotin moiety. Depending on the sequence of the particular nucleotide coupled to the substrate surface, either A, G, T, or C was added to the polynucleotide hybridized to that particular polynucleotide, in a manner analogous to that described above with reference to steps 701-704 of method 700 illustrated in FIG. 7. The polymerase and unreacted nucleotides were washed away, and the polynucleotides then were exposed to a solution including *Gaussia* luciferase coupled to a streptavidin moiety in a manner analogous to that described above with reference to step 705 of method 700 illustrated in FIG. 7. For polynucleotides to which nucleotide C had been added, the biotin moiety of that nucleotide C coupled to the streptavidin moiety of the *Gaussia* luciferase, thus coupling the *Gaussia* luciferase to nucleotide C. Excess *Gaussia* luciferase then was washed away. The polynucleotides then were exposed to chemiluminogenic molecule d-luciferin in a manner analogous to that described above with reference to step 706 of method 700 illustrated in FIG. 7.

Subsequently, the *Gaussia* luciferase was cleaved from nucleotide C, the cleaved *Gaussia* luciferase and d-luciferin were washed away, and the polynucleotides then again were contacted with a polymerase and with a solution including nucleotides A, G, T, and C, again with only nucleotide C was coupled to a biotin moiety. Depending on the sequence of the particular polynucleotide coupled to the substrate surface, either A, G, T, or C was added to the polynucleotide hybridized to that particular polynucleotide. Because the sequences of the various polynucleotides were different than each other, nucleotide C may have been added to different polynucleotides than in the previous cycle. The polymerase and unreacted nucleotides were washed away, and the polynucleotides then were exposed to a solution including *Gaussia* luciferase coupled to a streptavidin moiety in a manner analogous to that described above with reference to step 705 of method 700 illustrated in FIG. 7. For polynucleotides to which nucleotide C had been added, the biotin moiety of that nucleotide C coupled to the streptavidin moiety of *Gaussia* luciferase, thus coupling the *Gaussia* luciferase to that nucleotide C. Excess *Gaussia* luciferase then was washed away. The polynucleotides then were exposed to chemiluminogenic molecule d-luciferin in a manner analogous to that described above with reference to step 706 of method 700 illustrated in FIG. 7. Such cycles of adding nucleotides, coupling nucleotide C to *Gaussia* luciferase, and exposing the polynucleotides to d-luciferin were repeated multiple times.

Figure 14A:
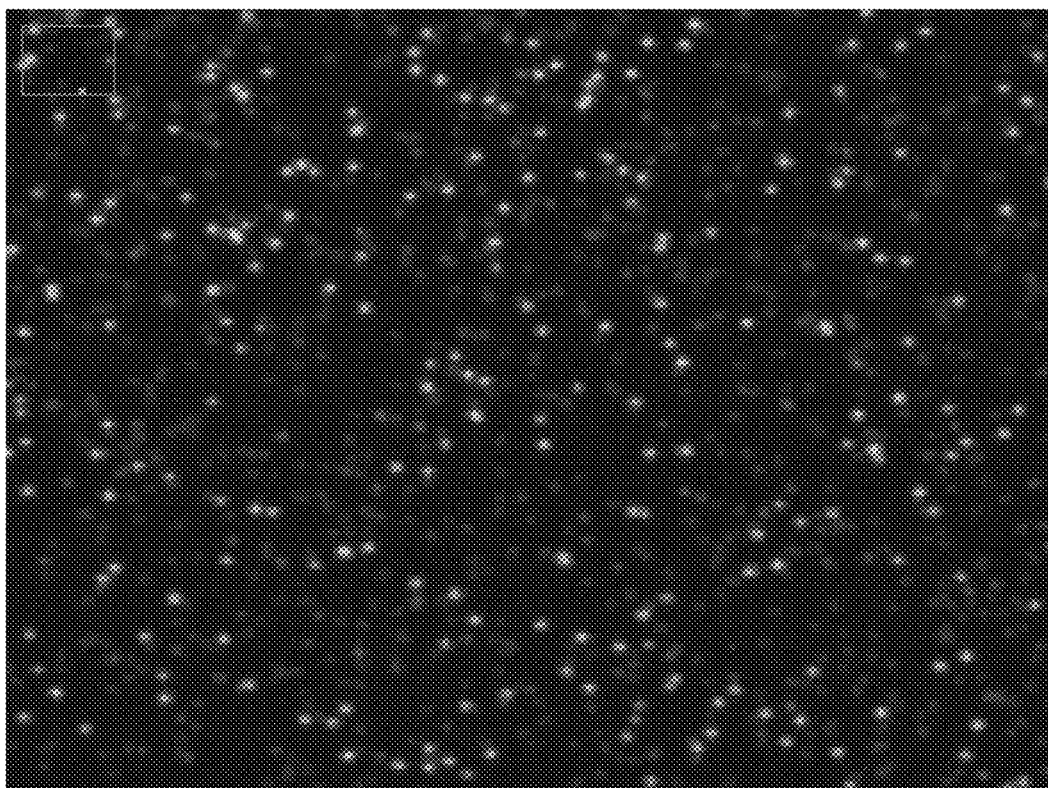
FIGS. 14A-14E illustrate images obtained during another illustrative method of detecting the presence of nucleotides in a polynucleotide using chemiluminescence, according to one exemplary embodiment of the present invention.
Figure 14B:
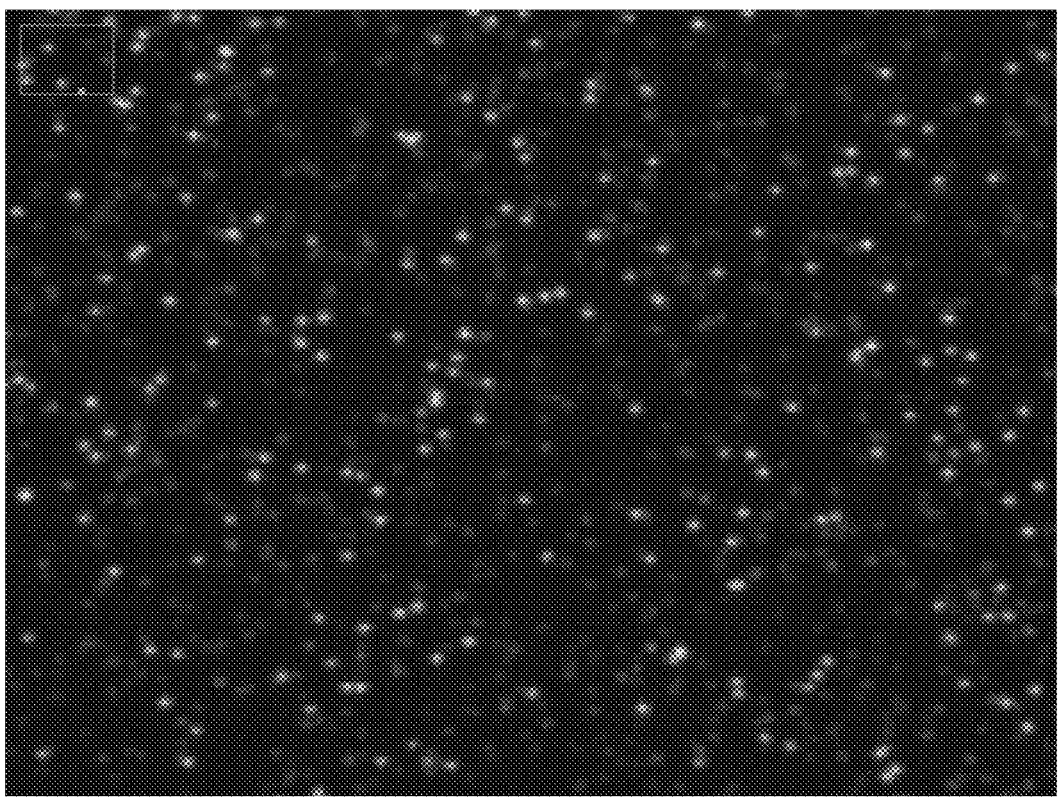

The images illustrated in FIGS. 14A-14E were obtained using a CCD camera disposed at a spaced distance from the substrate in a manner analogous to that described above with reference to FIGS. 10A and 11A. The CCD camera detected photons emitted resulting from interactions between the d-luciferin and the *Gaussia* luciferase in a manner analogous to that described above with reference to step 707 illustrated in FIG. 7. The gain of the CCD camera was equal to 8, and the integration time t for each image was approximately 1 second. The image illustrated in FIG. 14A corresponds to a first cycle such as described above. As such, the bright spots in FIG. 14A correspond to locations at which a nucleotide C was added to the polynucleotide that was hybridized to another polynucleotide coupled to the substrate surface, that is, for polynucleotides coupled to the substrate surface for which the next nucleotide in the sequence was G. The image illustrated in FIG. 14B corresponds to a second cycle such as described above. As such, the bright spots in FIG. 14B correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 14B are in different locations than the bright spots in FIG. 14A.

Figure 14C:
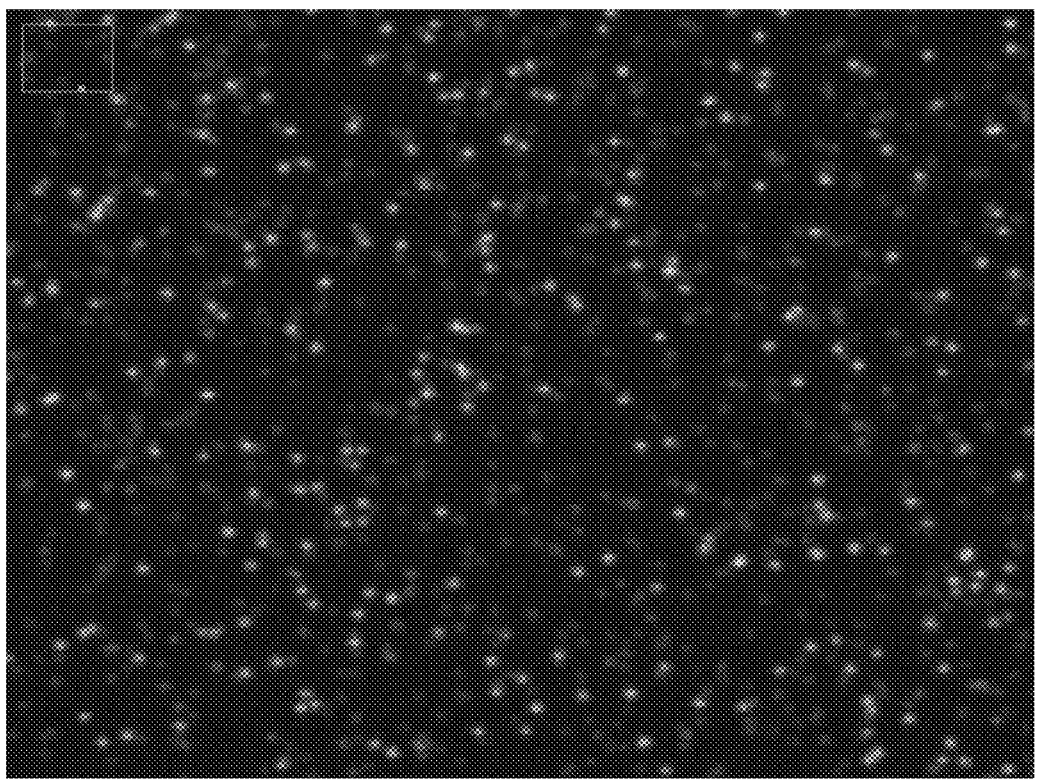
Figure 14D:
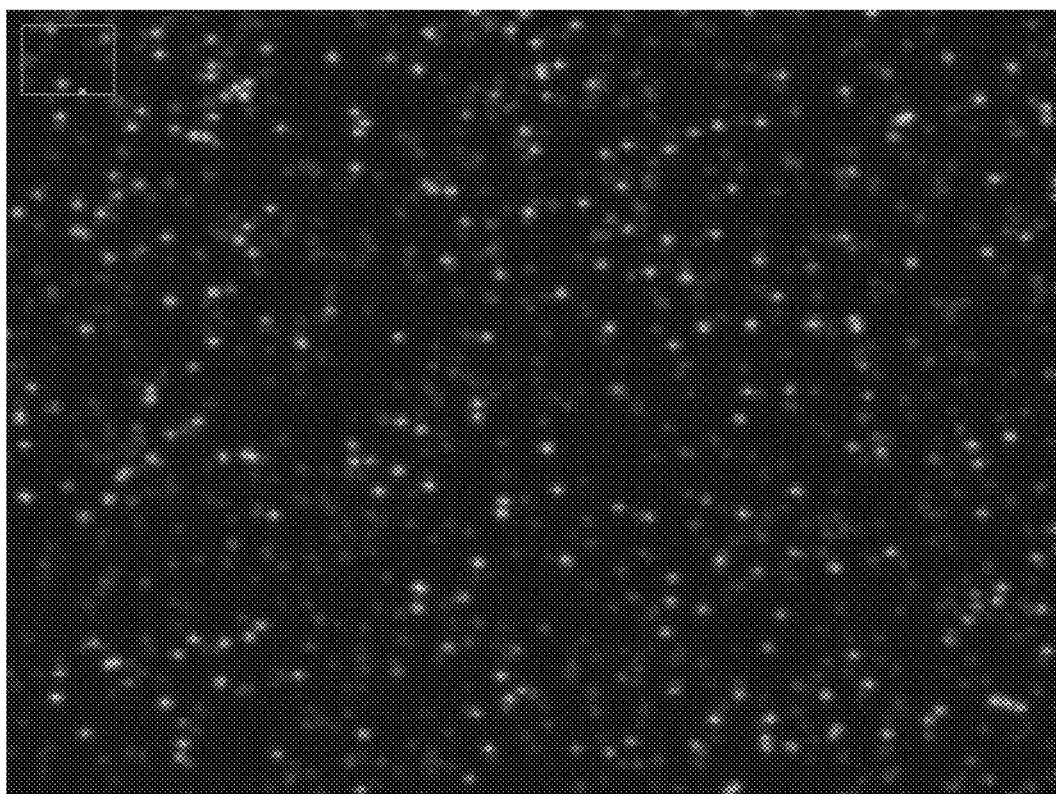

The image illustrated in FIG. 14C corresponds to a third cycle such as described above. As such, the bright spots in FIG. 14C correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 14C are in different locations than the bright spots in FIG. 14A or FIG. 14B. The image illustrated in FIG. 14D corresponds to a fourth cycle such as described above. As such, the bright spots in FIG. 14D correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 14D are in different locations than the bright spots in FIG. 14A, 14B, or 14C.

Figure 14E:
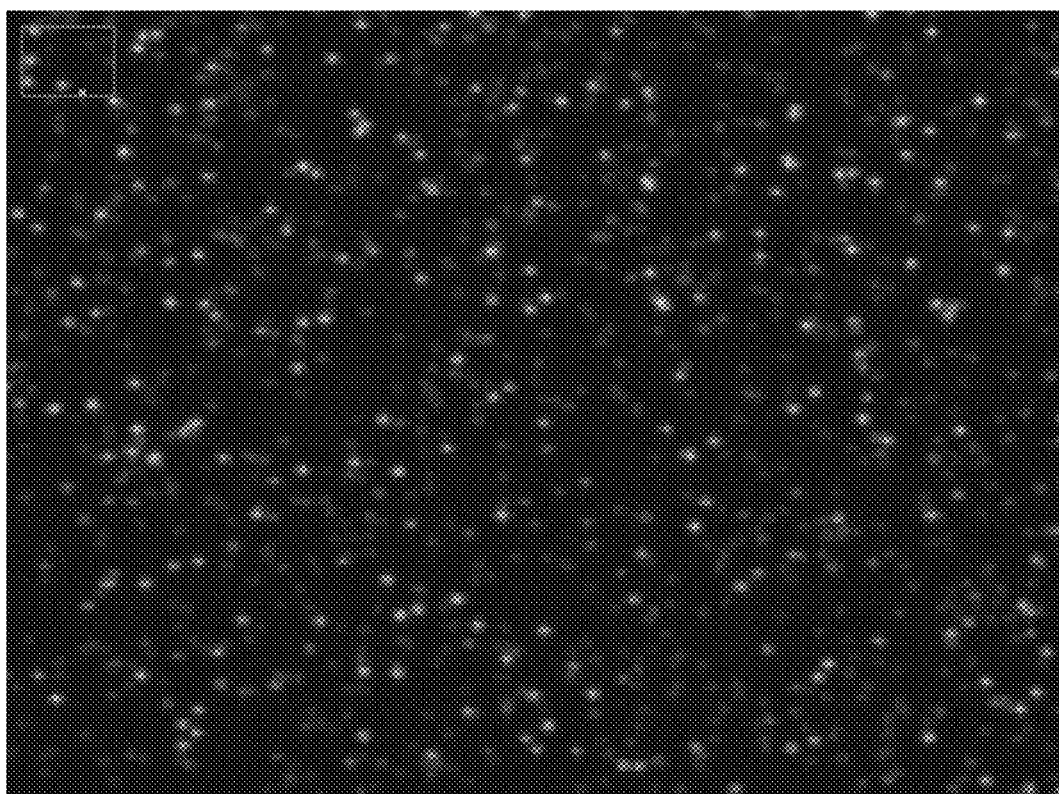

The image illustrated in FIG. 14E corresponds to a fifth cycle such as described above. As such, the bright spots in FIG. 14E correspond to locations at which a nucleotide C was added to the polynucleotide that was hybridized to another polynucleotide coupled to the substrate surface, that is, for polynucleotides coupled to the substrate surface for which the next nucleotide in the sequence was G. Because the various polynucleotides coupled to the substrate surface have different sequences than one another, it can be seen that at least some of the bright spots in FIG. 14E are in different locations than the bright spots in FIG. 14A, 14B, 14C, or 14D.

Figure 15A:
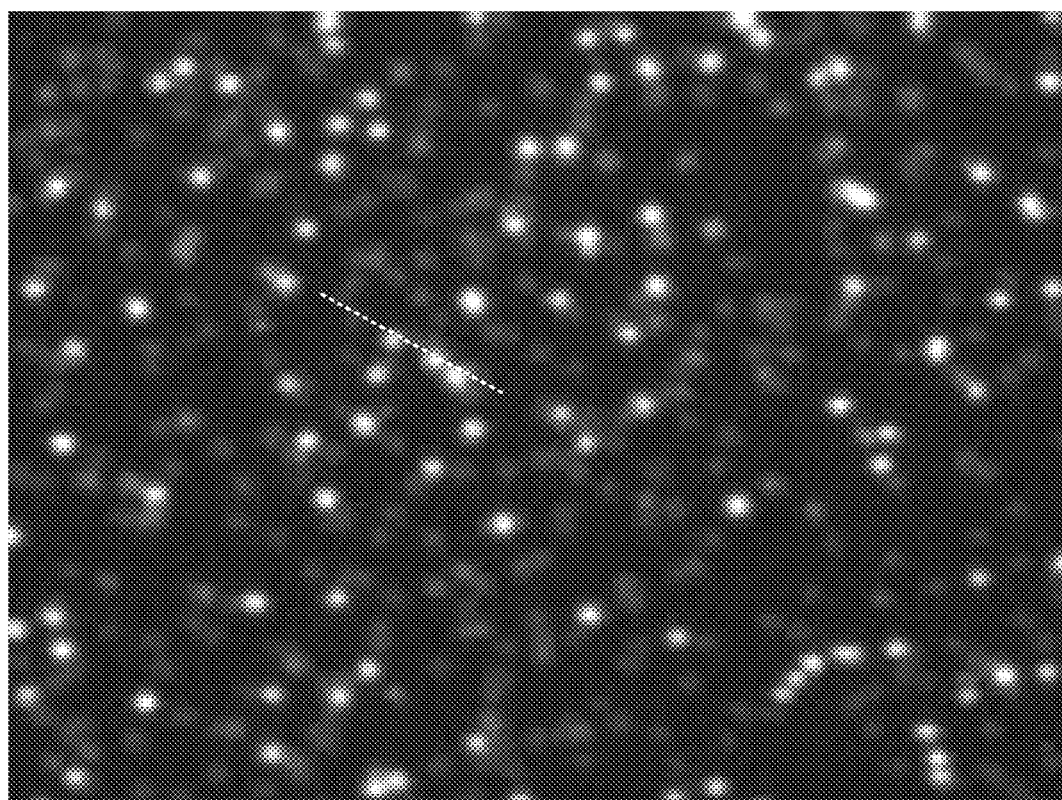
FIG. 15A illustrates an image obtained during another illustrative method of detecting the presence of nucleotides in a polynucleotide using chemiluminescence, according to one exemplary embodiment of the present invention.
Figure 15B:
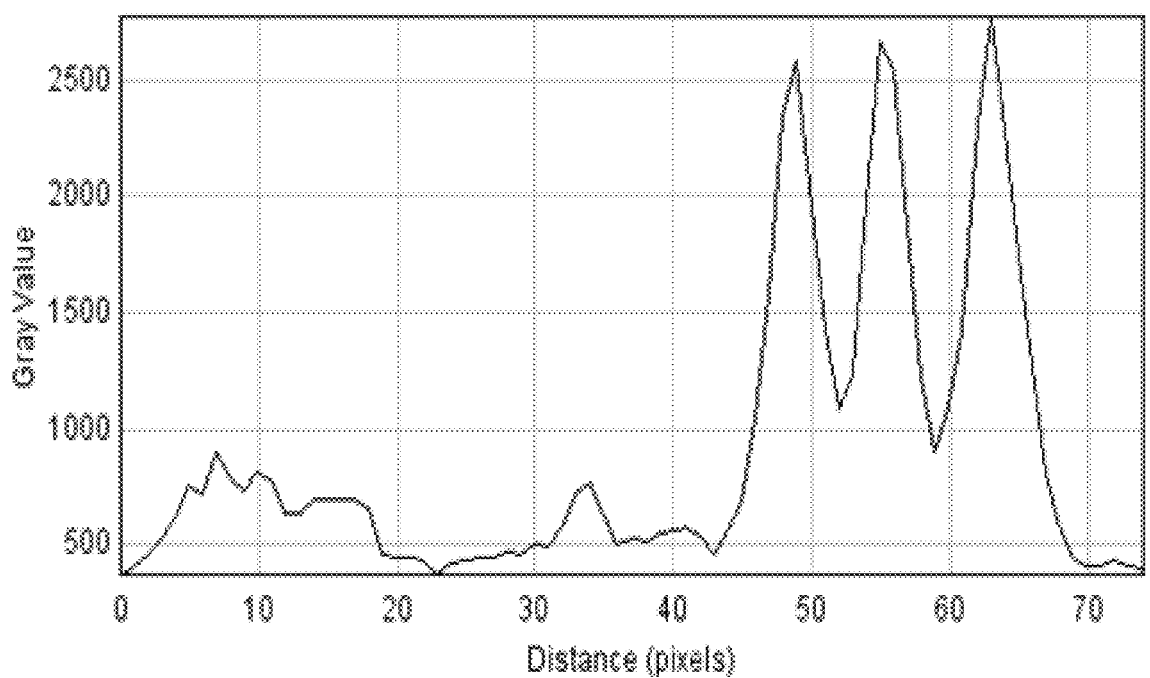
FIG. 15B illustrates a plot of pixel intensity as a function of distance in the image of FIG. 15A, according to one exemplary embodiment of the present invention.

FIG. 15A illustrates an image obtained during another illustrative method of detecting the presence of nucleotides in a polynucleotide using chemiluminescence, according to one exemplary embodiment of the present invention. More specifically, the image was obtained in a manner analogous to that described above with reference to FIGS. 14A-14E, e.g., by coupling nucleotide C to *Gaussia* luciferase and exposing the polynucleotides to d-luciferin. FIG. 15B illustrates a plot of pixel intensity as a function of distance in the image of FIG. 15A, according to one exemplary embodiment of the present invention. More specifically, the intensities (gray values) of pixels that lay approximately along the dotted line illustrated in FIG. 15A were plotted as a function of distance. It can be seen that pixels corresponding to the three bright spots had intensities of approximately 2500-2700 units. Without wishing to be bound by any theory, the regions of FIG. 15B having intensities of less than about 500 units, or less than about 400 units, are believed to correspond to regions without significant chemiluminescence, and thus can correspond to noise. As such, the S/N ratio of the intensities of the three bright spots to the noise can be estimated to be in the range of approximately 5 to 6.75 in this example. Thus, it can be understood that even with relatively low S/N ratios, e.g., of approximately 5, usable information about the sequence of a nucleotide readily can be obtained. Additionally, without wishing to be bound by any theory, the regions of FIG. 15B having intensities of between about 500 units and about 1000 units are believed to correspond to regions with low levels of chemiluminescence that do not necessarily correspond to locations at which nucleotide C has been added to a polynucleotide.

Additional Alternative Embodiments

In one nonlimiting embodiment, chemiluminescence-based SBS can be performed using an integrated CMOS flow cell. In one nonlimiting example, nucleotides and modified forms of luciferase can be coupled to one another via hapten moieties, and used for nucleotide discrimination (nucleotide detection) in a chemiluminescent SBS sequencing scheme. But it should be appreciated that other catalysts can be used, e.g., as described elsewhere herein. For example, a catalyst can be coupled to a nucleotide that has been incorporated into a polynucleotide, e.g., via hapten moieties, and a solution of chemiluminogenic molecules can be used for nucleotide discrimination in a chemiluminescent SBS sequencing scheme. Alternatively, the catalyst can be immobilized at sites of a patterned flow cell and the nucleotides coupled to chemiluminescence quenchers, e.g., via hapten moieties. In yet another example, the catalyst can be attached to a first nucleotide, such as a sequencing primer, and the nucleotides coupled to luminescence quenchers, e.g., via hapten moieties. Compositions, systems, and methods for chemiluminescence-based SBS on a droplet actuator also are provided.

Figure 16:
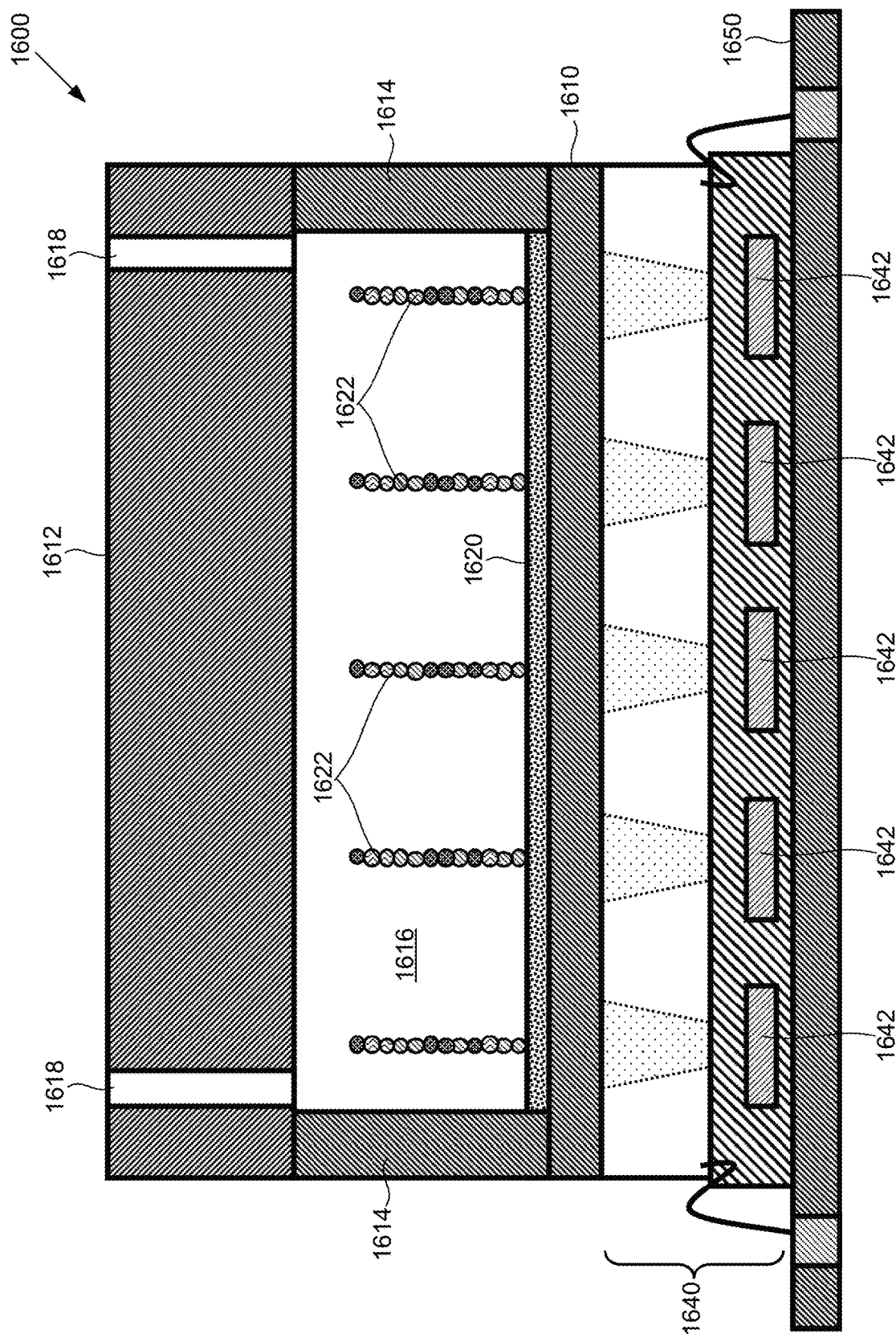
FIG. 16 illustrates a side cross-sectional view of an example of a flow cell that uses chemiluminescence for providing a substantially light-free luminescent sequencing by synthesis (SBS) scheme, according to one exemplary embodiment of the present invention.

FIG. 16 illustrates a side cross-sectional view of an example of a flow cell 1600 that uses for providing a substantially illumination-free luminescent SBS scheme, that is, SBS that needs not necessarily include the use of an illumination source, but instead can use light emitted by excited state chemiluminogenic molecules to detect the presence of nucleotides in a polynucleotide. Flow cell 1600 can include an integrated CMOS flow cell that can be illumination-free. For example, flow cell 1600 is designed to generate spatially localized chemiluminescence from excited state chemiluminogenic molecules, and to detect such chemiluminescence using an integrated CMOS sensor without the need for a separate illumination source such as a laser or lamp.

In the nonlimiting embodiment illustrated in FIG. 16, flow cell 1600 includes bottom substrate 1610 and top substrate 1612 that are separated from one another by spacers 1614. Bottom substrate 1610 can include, for example, a glass substrate, plastic substrate, CMOS substrate, or other suitable substrate. In one nonlimiting example, substrate 1610 includes a silicon dioxide ($SiO_2$) substrate to which CMOS circuitry 1640 is coupled. Top substrate 1612 can include, for example, a glass substrate, plastic substrate, or other suitable substrate. In one nonlimiting example, top substrate 1612 is about 0.4 mm thick, although other suitable thicknesses can be used, e.g., a thickness between about 0.1 mm and about 2 mm, or between about 0.2 mm and about 1 mm. In one nonlimiting example, spacers 1614 include adhesive spacers that are about 100 µm in height, although other suitable thicknesses can be used, e.g., a thickness between about 10 µm and about 1 mm, or between about 50 µm and about 500 µm. Accordingly, there is a space between bottom substrate 1610 and top substrate 1612, which forms, for example, a sequencing chamber 1616 in flow cell 1600. Sequencing chamber 1616 can include a flow channel that is supplied by inlets or outlets 1618 that are defined, for example, through top substrate 1612, although it should be appreciated that inlets or outlets 1618 suitably can be defined in, through, or between one or more of substrate 1610, substrate 1612, or spacers 1614. Liquid can be flowed into or out of sequencing chamber 1616 using any suitable combination of inlets or outlets 1618. Additionally, flow cell 1600 can be patterned so as to define one or more sequencing chambers 1616, each of which can have one or more corresponding inlets or outlets 1618 and can be configured to receive a corresponding one or more nucleotide primers 1622 such as described further below.

In certain embodiments, a hydrophilic layer 1620 can be disposed on, or can be provided as part of, bottom substrate 1610 and at least partially located inside sequencing chamber 1616. Hydrophilic layer 1620 can include any hydrophilic material suitable for conducting surface-based SBS chemistry in flow cell 1600. Hydrophilic layer 1620 can have a thickness, for example, from about 300 nm to about 400 nm thick, although other thicknesses suitably can be used, e.g., from about 1 nm to about 1 mm, or from about 10 nm to about 100 µm, or from about 20 nm to about 20 µm, or from about 50 nm to about 500 nm. In one example, hydrophilic layer 1620 includes a polyacrylamide gel coating, such as a mixture of norbornene (or norbornylene or norcamphene) and poly(N-(5-azidoacetamidylpentyl) acrylamide-co-acrylamide), also known as PAZAM. In another example, hydrophilic layer 1620 includes poly(N-(5-azidoacetamidylpentyl) acrylamide-co-acrylamide-co-acrylonitrile), also known as PAZAM-PAN. In some embodiments, the PAZAM and/or PAZAM-PAN can be modified to be thermally responsive, thereby forming a thermo-responsive polyacrylamide gel. More details about PAZAM can be found with reference to George et al., U.S. Patent Publication No. 2014/0079923, the entire contents of which are incorporated by reference herein.

A plurality of oligonucleotide primers 1622 are immobilized on hydrophilic layer 1620 in sequencing chamber 1616. Oligonucleotide primers 1622 can include capture primers to which single-stranded DNA fragments can be hybridized and amplified to form clonal DNA template clusters for SBS. The single-stranded DNA fragments can define a first polynucleotide to be sequenced; a second polynucleotide can be hybridized to the first polynucleotide, and nucleotides added to the second polynucleotide based on the sequence of the first polynucleotide. The identities of such nucleotides of the second polynucleotide can be determined, e.g., using one or more of the compositions, systems, and methods provided herein.

In the embodiment illustrated in FIG. 16, exemplary flow cell 1600 also includes a CMOS device, such as a CMOS image sensor 1640 that is mechanically and optically coupled to, or provided as part of, bottom substrate 1610. CMOS image sensor 1640 can include an array of pixels 1642 that respectively are directed toward a corresponding one of oligonucleotide primers 1622. CMOS image sensor 1640 can include, for example, any off-the-shelf CMOS image sensor. In one example, CMOS image sensor 1640 can be mounted on, coupled to, or provided as a part of a printed circuit board (PCB) 1650.

In flow cell 1600, the signal generated by the SBS reaction is generated via chemiluminescence and need not necessarily require excitation radiation. The lack of excitation radiation can obviate the need for a blocking filter and light curtains, therefore greatly simplifying the structure of the integrated CMOS flow cell (e.g., flow cell 1600) and eliminating a significant liability of photoluminescence-based designs based on fluorescence, which can require a light blocking filter so as to reduce background radiation from an excitation light source, and also the need to protect that filter from the sequencing chemistry. Therefore, as compared with photoluminescence-based flow cells that can include complex light blocking filters and light curtains and an illumination source, an aspect of flow cell 1600 is that it uses a chemiluminescence-based detection scheme, which in some embodiments can feature the absence of blocking filters, few or no light curtains, and the absence of illumination sources, thereby providing a relatively simpler and lower cost design that can be used in SBS.

In some embodiments, the photoluminescent catalyst is *Gaussia* luciferase. For example, in one exemplary reaction, *Gaussia* luciferase catalyzes the oxidation of the chemiluminogenic substrate coelenterazine to coelenteramide in a reaction that produces light and carbon dioxide. Coelenteramide is the light-emitting molecule found in many aquatic organisms across seven phyla. The *Gaussia* luciferase enzyme can be provided in two modified forms (1) a "flash" type and (2) a "glow" type, can have an efficiency approaching 90%. As such, the *Gaussia* luciferase enzyme can be used for nucleotide discrimination in a chemiluminescent SBS sequencing scheme, such as described herein, e.g., with reference to FIGS. 17 and 18.

Figure 17:
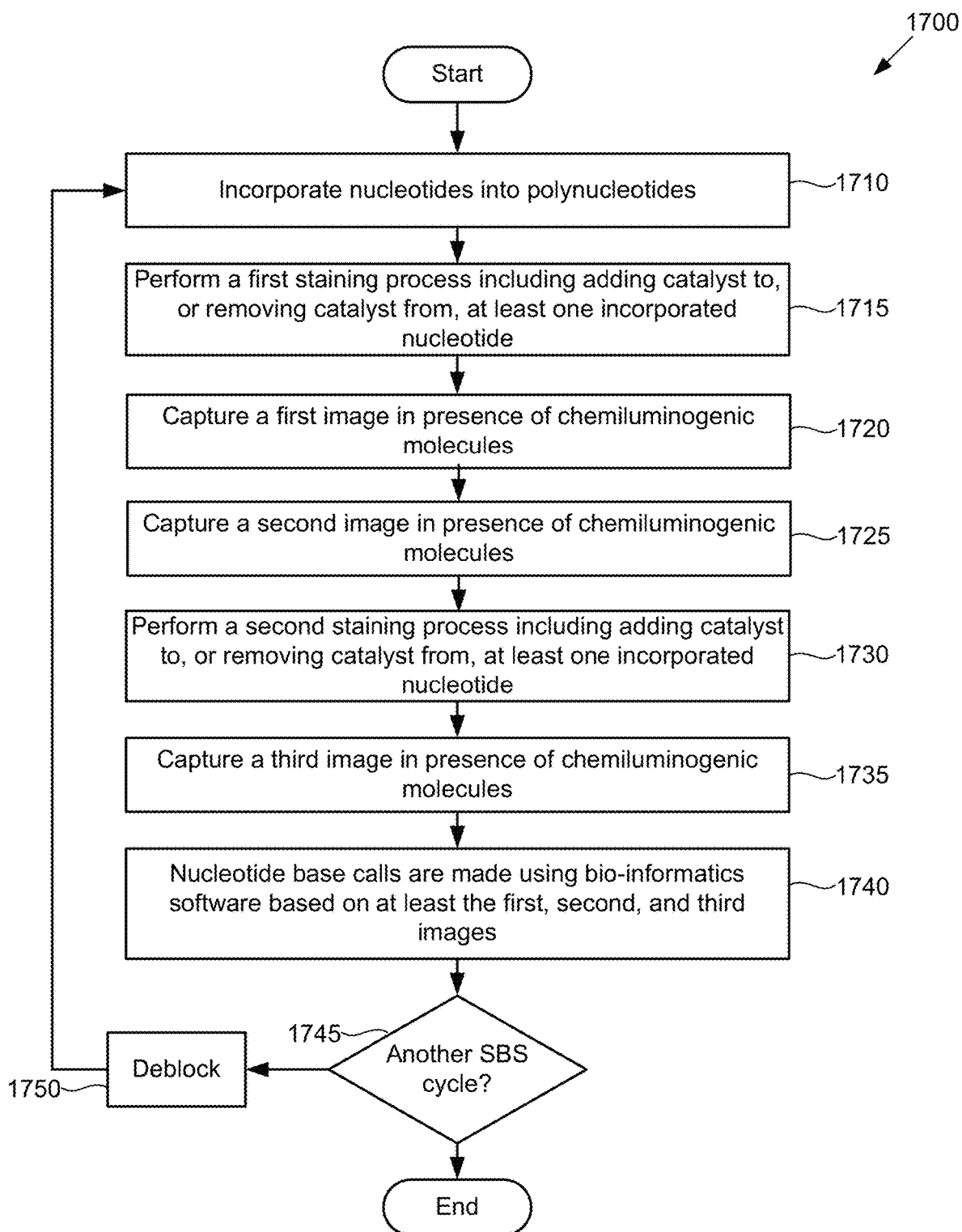
FIG. 17 illustrates a flow diagram of an example of a method of base discrimination in a chemiluminescent SBS sequencing scheme using the flow cell of FIG. 16, according to one exemplary embodiment of the present invention.
Figure 18:
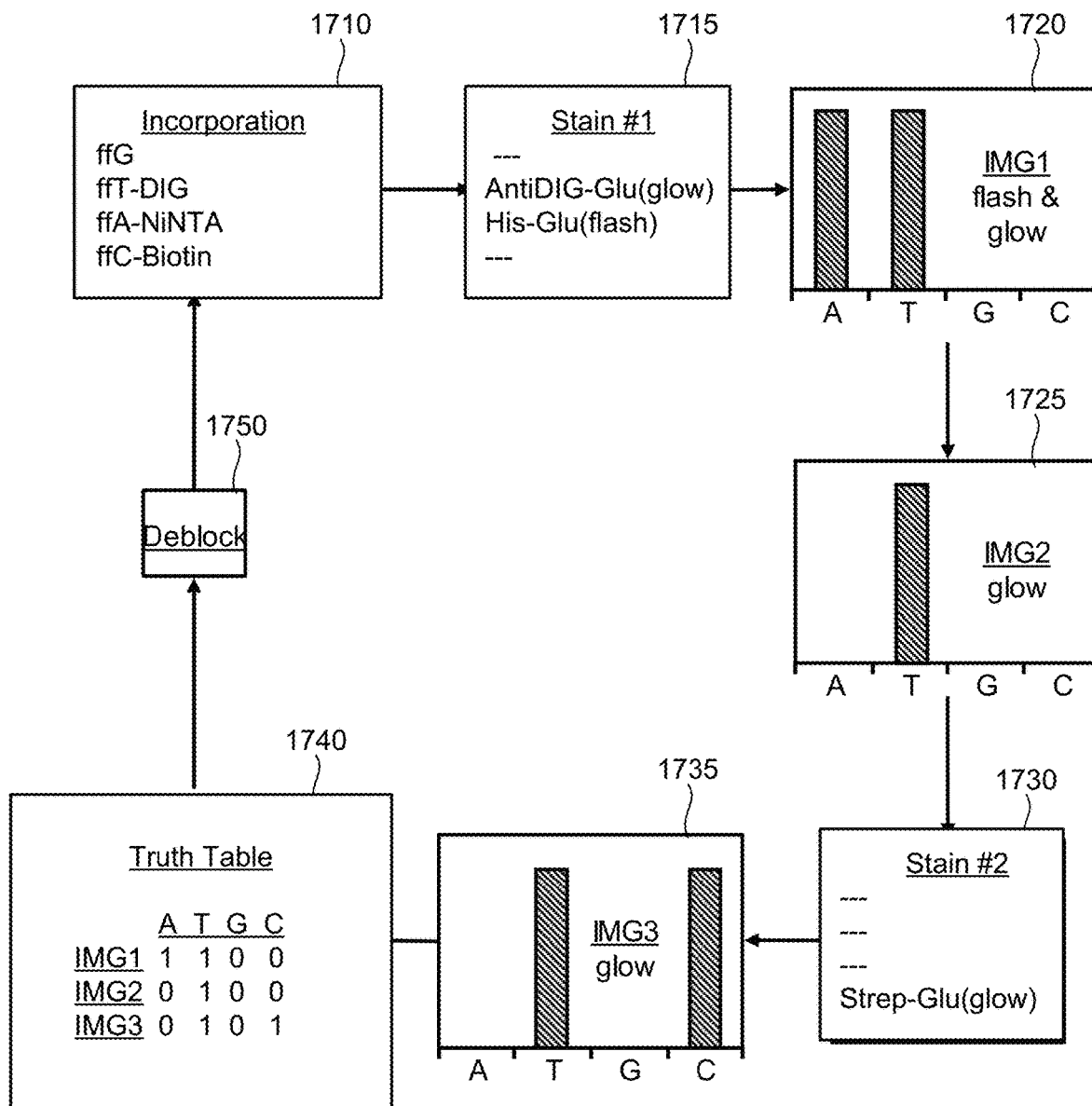
FIG. 18 illustrates a schematic diagram showing pictorially the steps of the method of FIG. 17, according to one exemplary embodiment of the present invention.

FIG. 17 illustrates a flow diagram of an example of a method 1700 of base discrimination in a chemiluminescent SBS sequencing scheme using, for example, flow cell 1600 of FIG. 16. FIG. 18 illustrates a schematic diagram showing pictorially the steps of method 1700 of FIG. 17. In one illustrative embodiment, method 1700 uses hapten labeled fully functionalized (ff) nucleotides (ffA, ffT, ffC, and ffG), and hapten labeled *Gaussia* luciferase (Glu) "flash" and "glow" enzymes for detection and discrimination of a nucleotide incorporation event. In one nonlimiting example, method 1700 uses digoxigenin (DIG)-labeled ffT (ffT-DIG) and "glow" Glu labeled with an antibody (or antibody fragment) specific for DIG (e.g., antiDIG-Glu(glow)) to detect incorporation of ffT, Ni-NTA labeled ffA (ffA-NiNTA, where NTA is nitrilotiacetic acid that, when chelated with Ni, binds to histidine) and histidine-labeled "flash" Glu (His-Glu(flash)) to detect incorporation of ffA, and biotin labeled ffC (ffC-Biotin) and streptavidin-labeled "glow" Glu (strep-Glu(glow)) to detect incorporation of ffC. The ffG nucleotide can be "dark", e.g., ffG need not necessarily be labeled for detection. Other labeling schemes and other hapten pairs can be analogous to those described elsewhere herein. Referring now to FIG. 17, method 1700 includes, but is not limited to, the following steps.

At step 1710, nucleotides respectively are incorporated into polynucleotides, e.g., growing complementary strands, e.g., are incorporated into a second polynucleotide hybridized to a first polynucleotide that is hybridized to a corresponding one of sequencing primers 1622 illustrated in FIG. 16, using a polymerase (not specifically illustrated) in an SBS cycle. The nucleotide incorporated into a given one of such second polynucleotides can be ffT-DIG, ffA-NiNTA, ffC-biotin, or ffG, depending upon the particular sequence of the corresponding first polynucleotide. This step is also shown pictorially in the schematic diagram of FIG. 18. It should be appreciated that the nucleotides incorporated into different second polynucleotides can be different than one another, based on the different sequences of the first polynucleotides.

At step 1715, a first staining process is performed that includes adding a catalyst to, or removing a catalyst from, at least one incorporated nucleotide. In one exemplary staining process, step 1715 using antiDIG-Glu(glow) and His-Glu (flash) is performed to detect incorporation of A and T nucleotides. For example, a first staining solution that includes antiDIG-Glu(glow) and His-Glu(flash) can be flowed through flow cell 1600. Complex formation between any incorporated ffT-DIG nucleotides and anti-DIG-Glu (glow) selectively stains the corresponding cluster with the "glow" form of the *Gaussia* luciferase enzyme. Similarly, complex formation between incorporated ffA-NiNTA nucleotides and His-Glu(flash) selectively stains a cluster with luciferase enzyme. This step is also shown pictorially in the schematic diagram of FIG. 18.

At step 1720, a first image is captured in the presence of chemiluminogenic molecules. In one nonlimiting example, a first image is captured for detection of both antiDIG-Glu (glow) and His-Glu(flash) signals. For example, using CMOS detector 1640 of flow cell 1600, a first image (e.g., IMG1) is captured for detection of both antiDIG-Glu(glow) and His-Glu(flash) signals during or following flow of a solution of appropriate chemiluminogenic molecules, (e.g., a solution of coelenterazine or colenterazine derivative) through flow cell 1600 to generate a localized chemiluminescent signal. In one nonlimiting example, the first image is captured using a 1-second integration time. The first image captures both a flash emission signal generated by the formation of an ffA-NiNTA/His-Glu(flash) binding complex (corresponding to incorporation of an A nucleotide into a corresponding second polynucleotide) and a glow emission signal generated by the formation of an ffT-Dig/antiDIG-Glu(glow) binding complex (corresponding to incorporation of a T nucleotide into a corresponding second polynucleotide). This step is also shown pictorially in the schematic diagram of FIG. 18.

At step 1725, a second image is captured in the presence of chemiluminogenic molecules. In one nonlimiting example, a second image is captured for discrimination of incorporated A from T. For example, using CMOS detector 1640 of flow cell 1600, a second image (e.g., IMG2) is captured for discrimination of incorporated A from T. The second image is captured after the exemplary 1-second integration time used to capture the first image. Note that the flash emission signal, corresponding to incorporation of an A nucleotide, has a relatively limited lifetime, typically less than one second. Thereafter, the flash emission signal can be extinguished following capture of the first image, and as such, in the second image, substantially only the glow emission signal generated by the formation of the ffT-DIG/ antiDIG-Glu(glow) binding complex (corresponding to incorporation of a T nucleotide into a corresponding second polynucleotide) is captured. This step is also shown pictorially in the schematic diagram of FIG. 18.

At step 1730, a second staining process is performed that includes adding a catalyst to, or removing a catalyst from, at least one incorporated nucleotide. In one example, a second staining process using strep-Glu(glow) is performed to detect incorporation of a C nucleotide. For example, a second staining solution that includes strep-Glu(glow) is flowed through flow cell 1600. Complex formation between incorporated ffC-Biotin nucleotides and strep-Glu(glow) selectively stains a cluster with the "glow" form of the *Gaussia* luciferase enzyme. This step is also shown pictorially in the schematic diagram of FIG. 18.

At step 1735, a third image is captured in the presence of chemiluminogenic molecules. In one illustrative embodiment, a third image is captured for detection of a strep-Glu (glow) signal from incorporated C nucleotides in addition to antiDIG-Glu(glow) signal from incorporated T nucleotides. For example, using CMOS detector 1640 of flow cell 1600, a third image (e.g., IMG3) is captured. A new glow signal is detected by the formation of an ffC-Biotin/strep-Glu(glow) binding complex and indicates incorporation of a C nucleotide into a corresponding second polynucleotide following or during flow of a solution of appropriate chemiluminogenic molecules through flow cell 1600 to generate a localized chemiluminescent signal. The glow signal from the incorporation of a T nucleotide previously captured in the first (step 1720) and second (step 1725) images is also captured in this third imaging step. This step is also shown pictorially in the schematic diagram of FIG. 18. Note that in some embodiments, IMG3 can be captured following a greater than approximately 1 second delay after step 1730, so that any flash signal resulting from additional introduction of the chemiluminogenic molecules can be extinguished before capture of IMG3, so that substantially only glow signals from C and T incorporation are included in IMG3. Alternatively, IMG3 can be obtained immediately following step 1730, so as to capture both flash signal from incorporation of A and glow signals from incorporation of C and T. In this regard, note that such an image can be used instead of, or in addition to, the first image at step 1720 that captures both flash and glow signals; an additional image, e.g., a fourth image, subsequently can be obtained after the flash signal is extinguished.

At step 1740, nucleotide base calls are made using bioinformatics software based on at least the first, second, and third images. In this example, incorporation of A is detected as a flash emission signal, and incorporation of T is detected as a glow emission signal in the first image and A is discriminated from T in the second image based on the absence of the flash emission signal in the second image. Incorporation of C is detected as a glow signal in the third image, and is discriminated from T based on an absence of the glow signal from C in the first image. Incorporation of G is determined based on the lack of an emission signal in images 1 through 3. This step is also shown pictorially in the schematic diagram of FIG. 18, in the form of a truth table wherein the "1" in each row means that the nucleotide in that column corresponds to a bright signal (either glow or flash) in the corresponding image.

At decision step 1745, it is determined whether another cycle of SBS is desired. If another SBS cycle is desired, then method 1700 proceeds to step 1750. If another SBS cycle is not desired, then method 1700 ends.

At a step 1750, a deblocking reaction is performed to remove a blocking group on each of the incorporated nucleotides so as to facilitate the next nucleotide addition in the next SBS cycle. Method 1700 returns to step 1710. This step is also shown pictorially in the schematic diagram of FIG. 18.

In another example, incorporation of a C nucleotide is detected as a flash signal in the third image. In this example, a Strep-Glu(flash) enzyme is used in step 1730 and an exemplary 1-second integration time is used in step 1735.

In another example, luminol-based chemiluminescence can be used for SBS sequencing by coupling a catalyst (e.g., HRP or a Ni-NTA complex) to a fully functionalized nucleotide(s) (ffN), e.g., after the ffN is incorporated into a polynucleotide in a manner such as described elsewhere herein. Each ffN then generates multiple singlet oxygen atoms that interact with excess luminol in the flow cell to generate light.

Figure 19:
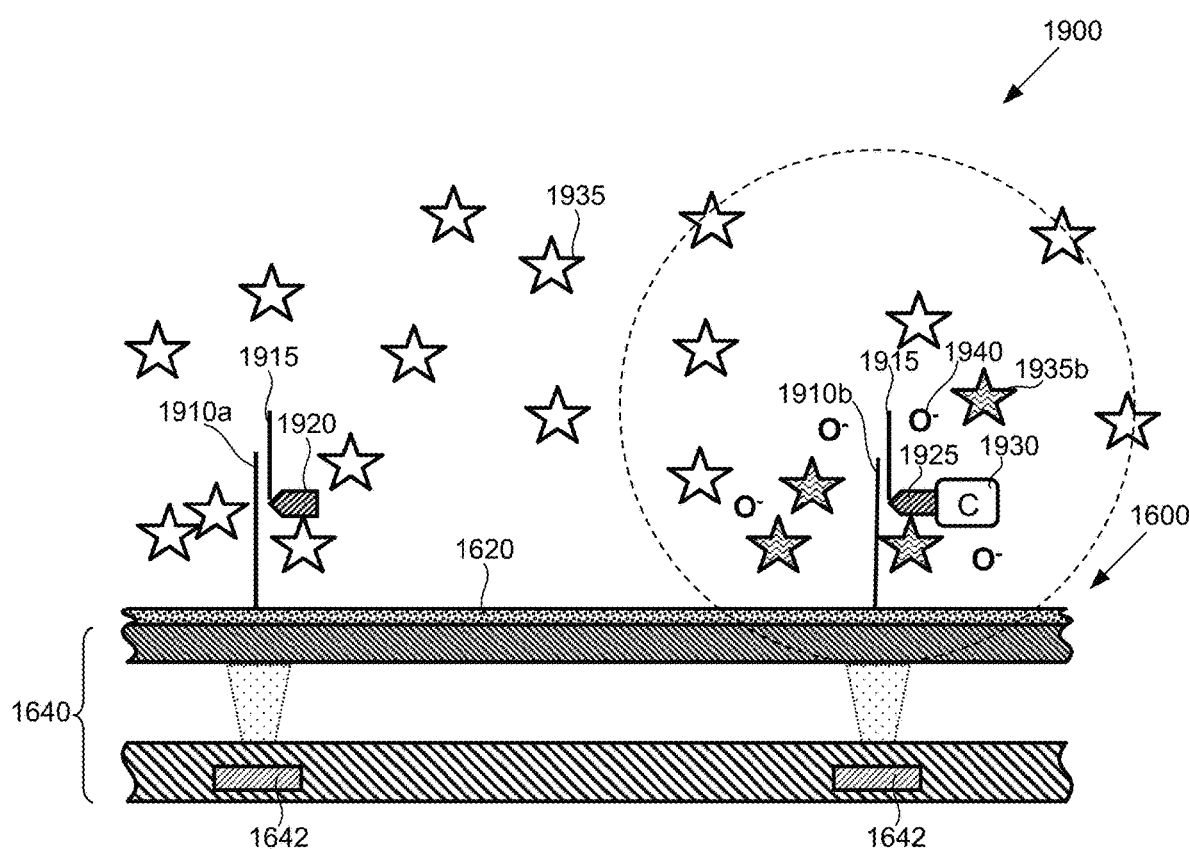
FIG. 19 shows a portion of the flow cell of FIG. 16 and depicts an example of a chemiluminescent SBS scheme, wherein a catalyst immobilized on a nucleotide is used to generate a chemiluminescent signal, according to one exemplary embodiment of the present invention.

In one illustrative embodiment, FIG. 19 shows a portion of flow cell 1600 of FIG. 16 and depicts an example of another nonlimiting chemiluminescent SBS scheme 1900, wherein a catalyst coupled to a nucleotide is used to generate a chemiluminescent signal. In this example, DNA template strands 1910 (e.g., DNA template strands 1910a and 1910b) formed in a cluster amplification process are immobilized on hydrophilic layer 1620 via oligonucleotide primer 1622 (not shown). DNA template strand 1910a is one template strand of a first clonal cluster and DNA template strand 1910b is one template strand in a second clonal cluster. Hybridized to DNA template strands 1910 are sequencing primers 1915, e.g., second polynucleotides to which a nucleotide can be added based on the sequence of the corresponding DNA template strand 1910a or 1910b.

In an exemplary SBS cycle, sequencing primers 1915 are extended and a nucleotide 1920 is incorporated based on the sequence of DNA template strand 1910a and a nucleotide 1925 is incorporated based on the sequence of DNA template strand 1910b, e.g., using corresponding polymerases (not specifically illustrated). Nucleotide 1925 is coupled to catalyst 1930, e.g., by coupling a moiety coupled to nucleotide 1925 to a moiety coupled to catalyst 1930. A solution of chemiluminogenic molecules 1935 is flowed into flow cell 1600. In one nonlimiting example, chemiluminogenic molecules 1935 include luminol and catalyst 1930 includes a bio-compatible Ni-NTA complex that is a catalyst for the luminol reaction. Catalyst 1930 coupled to incorporated nucleotide 1925 triggers the decomposition of $H_2O_2$ (that can be flowed into flow cell 1600, not shown) to singlet oxygen (O) 1940 and water (not shown). Singlet O 1940 reacts with excess chemiluminogenic molecules 1935, which generate light responsive to interaction with the singlet O. In certain embodiments, light is only generated by chemiluminogenic molecules 1935 within a certain distance from catalyst 1930, e.g., by excited state chemiluminogenic molecules 1935b. Based on published values, the approximate radius of the reaction zone (denoted by dashed circle) around each catalyst center is estimated to be approximately 200-400 nm. Light from the emitting excited state chemiluminogenic molecules 1935b within the reaction zone can be collected by, for example, a corresponding pixel 1642 of CMOS image sensor 1640. In this example, light emission is detected substantially only at the corresponding pixel 1642 in proximity of DNA template 1910b with nucleotide 1925 coupled to catalyst 1930. Note that such a chemiluminescence-based detection scheme, an absence of excitation radiation also can reduce or eliminate an optical background signal and can enhance the signal-to-noise (S/N) ratio of the CMOS sensor. Additionally, note that optical sensors other than CMOS sensors suitably can be used, such as described elsewhere herein.

Figure 20:
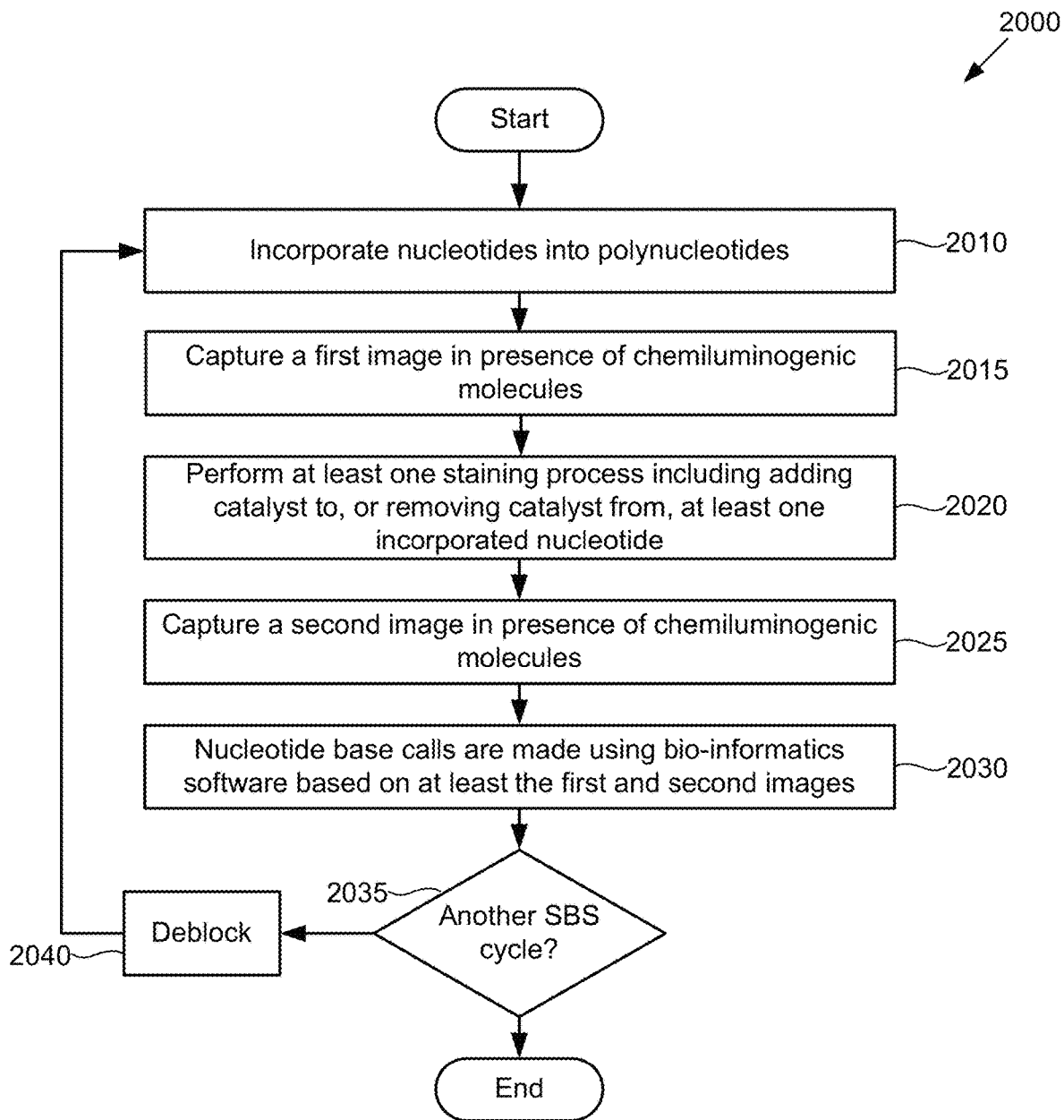
FIG. 20 illustrates a flow diagram of an example of a method of base discrimination in a chemiluminescent SBS sequencing scheme using the flow cell of FIG. 16, according to one exemplary embodiment of the present invention.
Figure 21:
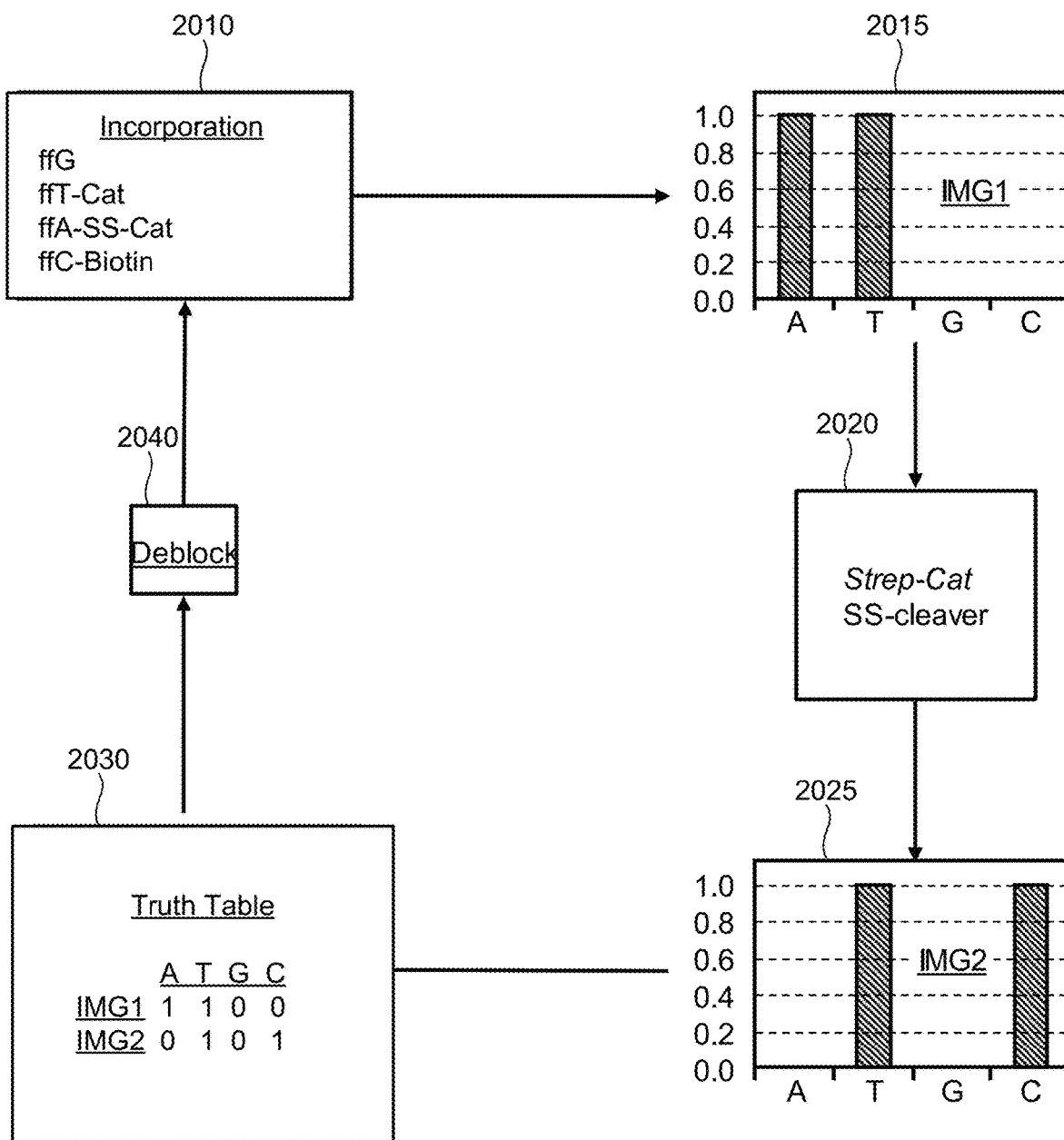
FIG. 21 illustrates a schematic diagram showing pictorially the steps of the method of FIG. 20, according to one exemplary embodiment of the present invention.

FIG. 20 illustrates a flow diagram of an example of a method 2000 of nucleotide discrimination in a chemiluminescent SBS sequencing scheme using, for example, flow cell 1600 of FIG. 16. FIG. 21 illustrates a schematic diagram showing pictorially the steps of method 2000 of FIG. 20. Method 2000 uses a catalyst coupled to an incorporated nucleotide and a chemiluminogenic molecule for detection and discrimination of a nucleotide incorporation event. Exemplary catalysts can include, but are not limited to, bio-mimicking Fe, Cu, or Ni catalysts, such as an Ni-NTA complex. For further details on exemplary compounds that can be used as catalysts, see Daeid et al., "Synthetic porphyrins/metalloporphyrins which mimic states in catalytic cycle of cytochrome P-450 and peroxidases," Pure and Applied Chemistry 65(7): 1541-1548 (1993), and Xu et al, "Manganese Porphyrin-dsDNA Complex: A Mimicking Enzyme for Highly Efficient Bioanalysis," Analytical Chemistry 85: 3374-3379 (2013), the entire contents of both of which are incorporated herein by reference. In one example, method 2000 uses a catalyst coupled to ffT nucleotides (ffT-Cat), a catalyst coupled to ffA nucleotides via a cleavable disulfide (SS) bond (ffA-SS-Cat), and biotin labeled ffC nucleotides (ffC-Biotin). The ffG nucleotide can be "dark", e.g., ffG is not labeled for detection, or can include another suitable moiety such as provided further herein. Other suitable couplings or haptens such as described herein can be used. Referring now to FIG. 20, method 2000 includes, but is not limited to, the following steps.

At step 2010, nucleotides are incorporated into polynucleotides, e.g., into growing complementary strands, e.g., into second polynucleotides that are hybridized to a first polynucleotide that is hybridized to a corresponding one of sequencing primers 1622 illustrated in FIG. 16, using a polymerase (not specifically illustrated), in an SBS cycle. In the illustrated embodiment, the particular nucleotide incorporated into the second polynucleotide can be ffT-Cat, ffA-SS-Cat, ffC-biotin, or dark ffG, depending upon the particular sequence of the first polynucleotide to which the second polynucleotide is hybridized. This step is also shown pictorially in the schematic diagram of FIG. 21.

At step 2015, a first image is captured in the presence of chemiluminogenic molecules. In one example, a first image is captured for detection of incorporated of A or T nucleotides. For example, using CMOS detector 1640 of flow cell 1600, a first image (e.g., IMG1) is captured for detection of incorporated of A or T nucleotides following or during flow of a solution of chemiluminogenic molecules through flow cell 1600 to generate a localized chemiluminescent signal at all sites (clusters) with incorporation of A or T. This step is also shown pictorially in the schematic diagram of FIG. 21.

At step 2020, at least one staining process is performed that includes adding catalyst to, or removing catalyst from, at least one incorporated nucleotide. In one nonlimiting example, a solution that includes streptavidin-catalyst (Strep-Cat) and a disulfide cleaver (SS-cleaver) is flowed through flow cell 1600. Suitable disulfide cleavers include, but are not limited to, strong reducing agents such as trishydroxypropylphosphine (THP), triscarboxyethylphosphine (TCEP), a number of other organic phosphines, and 2-mercaptoethanol. Exemplary complex formation between incorporated ffC-Biotin nucleotides and Strep-Cat selectively identifies sites (clusters) with incorporation of C. The SS-cleaver cleaves the disulfide bond in incorporated ffA-SS-Cat nucleotides and effectively removes the catalyst from A nucleotides thereby eliminating chemiluminescent signals that may be generated from those sites. This step is also shown pictorially in the schematic diagram of FIG. 21. It should be appreciated that the SS-cleaver and catalyst bound to a hapten, such as streptavidin, need not be added concurrently with one another, but can be added in any suitable order.

At step 2025, a second image is captured in the presence of chemiluminogenic molecules. In one example, a second image is captured for detection of incorporated C nucleotides. For example, using CMOS detector 1640 of flow cell 1600, a second image (e.g., IMG2) is captured for detection of incorporated C nucleotides following or during flow of a solution of chemiluminogenic molecules through flow cell 1600 to generate a localized chemiluminescent signal at all sites with incorporation of C. A chemiluminescent signal from incorporation of a T nucleotide is also captured. This step is also shown pictorially in the schematic diagram of FIG. 21.

At step 2030, nucleotide base calls are made using bioinformatics software based on at least the first and second images. In this example, incorporation of A and T are detected in the first image. Incorporation of C and T are detected in the second image. Because SS-cleaver was flowed through the flow cell at step 2020, the signal from incorporated A nucleotides is absent in the second image. Incorporation of G is determined based on the lack of an emission signal in images 1 and 2. This step is also shown pictorially in the schematic diagram of FIG. 21, in the form of a truth table wherein the "1" in each row means that the nucleotide in that column corresponds to a bright signal (corresponding to presence of the catalyst) in the corresponding image.

At a decision step 2035, it is determined whether another cycle of SBS is desired. If another SBS cycle is desired, then method 2000 proceeds to step 2040. If another SBS cycle is not desired, then method 2000 ends.

At step 2040, a deblocking reaction is performed to remove a blocking group on the incorporated nucleotides for the next nucleotide addition in the next SBS cycle. Method 2000 returns to step 2010. This step is also shown pictorially in the schematic diagram of FIG. 21.

Figure 22:
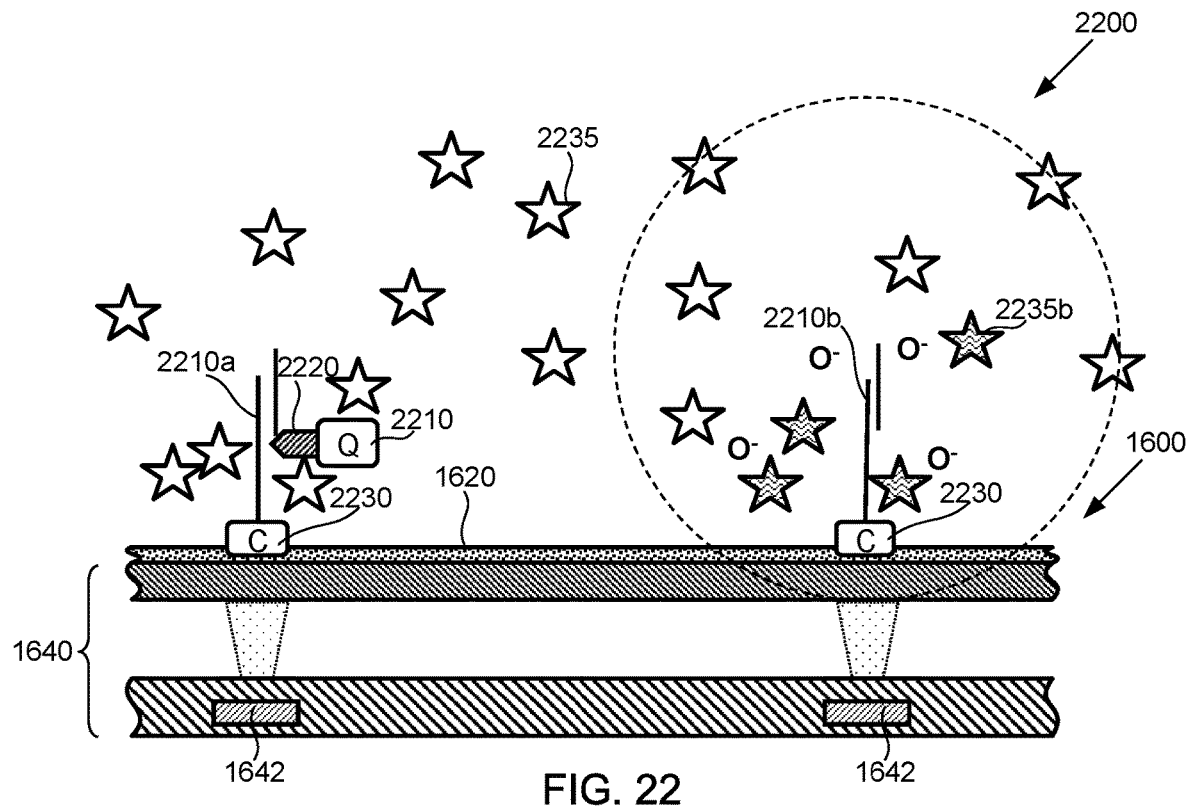
FIG. 22 illustrates an example of a chemiluminescent SBS scheme that is an alternative of the SBS scheme of FIG. 19, wherein the catalyst is immobilized at every site of a patterned flow cell and nucleotides are labeled with luminescence quenchers, according to one exemplary embodiment of the present invention.

FIG. 22 shows an example of a chemiluminescent SBS scheme 2200 that is an alternative to the SBS scheme of FIG. 19, and wherein the catalyst is immobilized at every site of a patterned flow cell and nucleotides are coupled to corresponding luminescence quenchers. In this example, catalyst 2230 is immobilized on hydrophilic layer 1620 atop bottom substrate 1610. Nucleotide 2220 is coupled to a luminescence quencher (Q) 2210. Luminescence quencher 2210 can include, for example, a small organic molecule such as BHQ, DABCYL, DNP, or QSY-1; other exemplary quenchers are described elsewhere herein. Light is substantially only generated by chemiluminogenic molecules 2235 within a certain distance from catalyst 2230 where there is no nucleotide incorporation, e.g., by excited state chemiluminogenic molecules 2235b at DNA template 2210b. Intensity at sites with incorporation of nucleotide 2220 with luminescence quencher 2210 coupled thereto (e.g., at DNA template 2210a) is suppressed. The quencher-based scheme offers the potential of four-color discrimination based on a unique level of suppression by the quencher Q used for each nucleotide. For example, one nucleotide is not coupled to a quencher, and the other three nucleotides respectively are coupled to quenchers of different efficiency than one another. Therefore, the brightness of each site provides information about which nucleotide is being incorporated. Schemes based on cleaving and blinking similar to those described herein also are possible. For example, one-color discrimination can be used in a manner such as described elsewhere herein.

Figure 23:
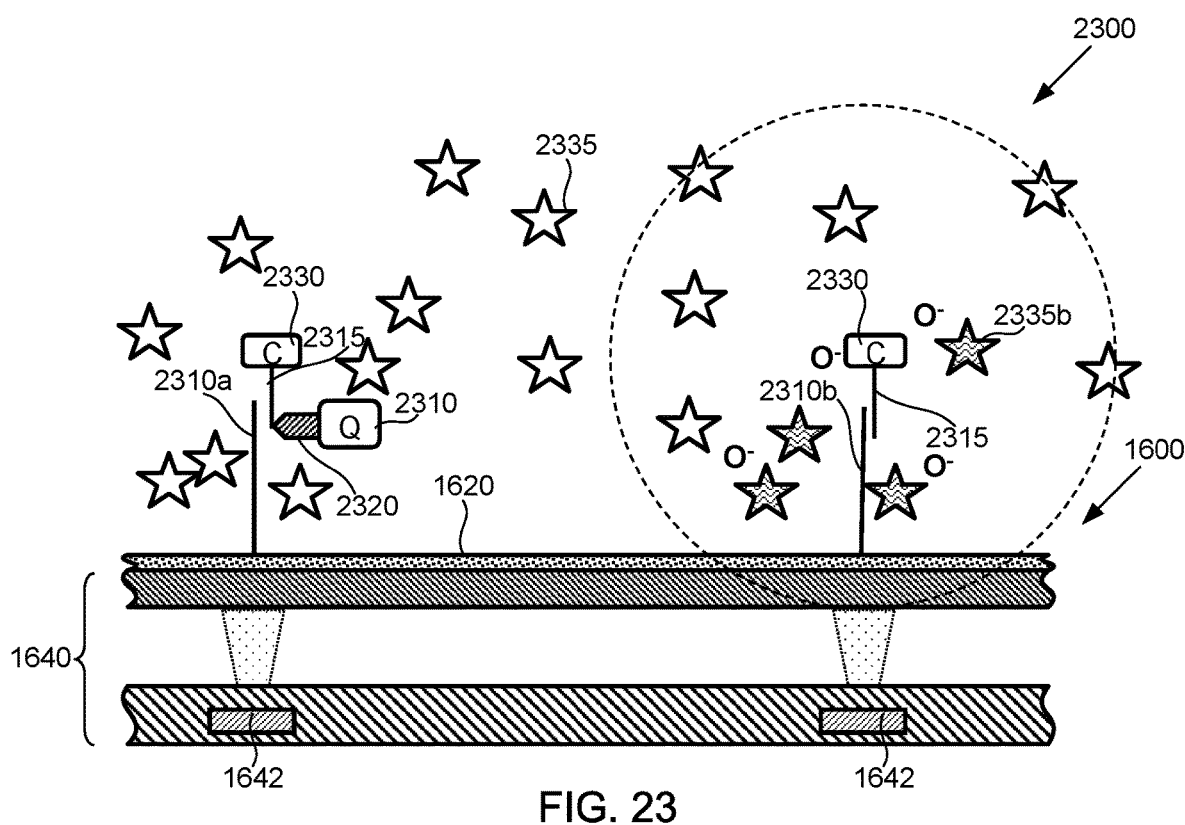
FIG. 23 illustrates an example of a chemiluminescent SBS scheme that is another alternative of the SBS scheme of FIG. 19, wherein the catalyst is attached to the sequencing primer and the nucleotides are labeled with luminescence quenchers, according to one exemplary embodiment of the present invention.

FIG. 23 shows an example of a chemiluminescent SBS scheme 2300 that is another alternative to the SBS scheme of FIG. 19, and wherein the catalyst is attached to the sequencing primer and the nucleotides are coupled to corresponding luminescence quenchers. In this example, catalyst 2330 is immobilized on sequencing primers 2315. Nucleotide 2320 is coupled to luminescence quencher 2310. Light is only generated by chemiluminogenic molecules 2335 within a certain distance from catalyst 2330 where there is no incorporation of a nucleotide to which quencher 2310 is coupled, e.g., by excited state chemiluminogenic molecules 2335b at DNA template 2310b. Intensity at sites with incorporation of nucleotide 2320 with luminescence quencher 2310 coupled thereto (at DNA template 2310a) is suppressed. Chemiluminescent SBS scheme 2300 is a relatively high throughput and manufacturing-friendly scheme, wherein the catalyst can be attached to the sequencing primer and each nucleotide labeled with a luminescence quencher.

Figure 24:
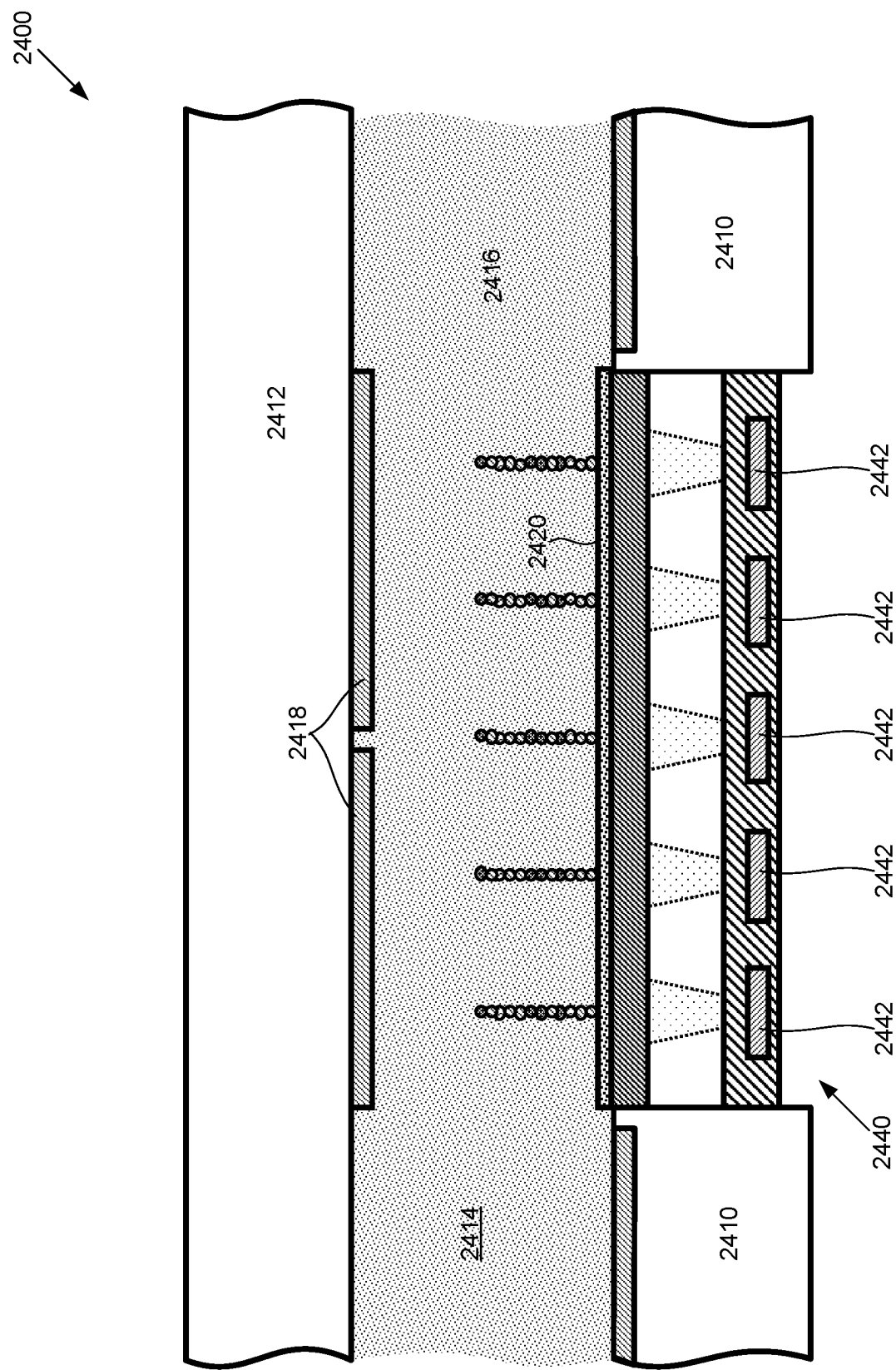
FIG. 24 illustrates a side cross-sectional view of an example of a droplet actuator that uses chemiluminescence for providing a substantially light-free luminescent SBS scheme, according to one exemplary embodiment of the present invention.

It should be appreciated that the presently disclosed chemiluminescence-based detection schemes are not limited to flow cell technology. The chemiluminescence-based detection schemes can be used, for example, in digital fluidics applications. For example, FIG. 24 illustrates a side cross-sectional view of an example of a droplet actuator 2400 that uses chemiluminescence for providing a substantially light-free luminescent SBS scheme. Droplet actuator 2400 can include an integrated CMOS-based digital fluidics device that is illumination-free. Namely, droplet actuator 2400 can be configured to generate spatially localized chemiluminescence and detect such chemiluminescence using an integrated CMOS sensor.

Droplet actuator 2400 includes a bottom substrate 2410 and a top substrate 2412 that are separated by a droplet operations gap 2414. Droplet operations gap 2414 contains filler fluid 2416. The filler fluid 2416 is, for example, low-viscosity oil, such as silicone oil or hexadecane filler fluid. Top substrate 2412 can include an arrangement of droplet operations electrodes 2418 (e.g., electrowetting electrodes). Bottom substrate 2410 can include a ground reference plane or electrode (not shown). Droplet operations are conducted adjacent to droplet operations electrodes 2418 on a droplet operations surface.

Further, CMOS detector 2440 can be integrated into bottom substrate 2410, and hydrophilic layer 2420 can be disposed atop CMOS detector 2440. CMOS detector 2440 and hydrophilic layer 2420 can be configured analogously to CMOS detector 1640 and hydrophilic layer 1620 described above with reference to FIG. 16. For example, CMOS detector 2440 can include pixels 2442. Because chemiluminescence-based detection schemes need not require illumination through top substrate 2412 onto hydrophilic layer 2420, features that are not optically transparent can be installed on top substrate 2412. For example, in droplet actuator 2400, additional droplet operations electrodes 2418 can be installed on, or provided as part of, top substrate 2412 in the vicinity of hydrophilic layer 2420 to assist electrowetting across the surface of hydrophilic layer 2420.

Figure 25:
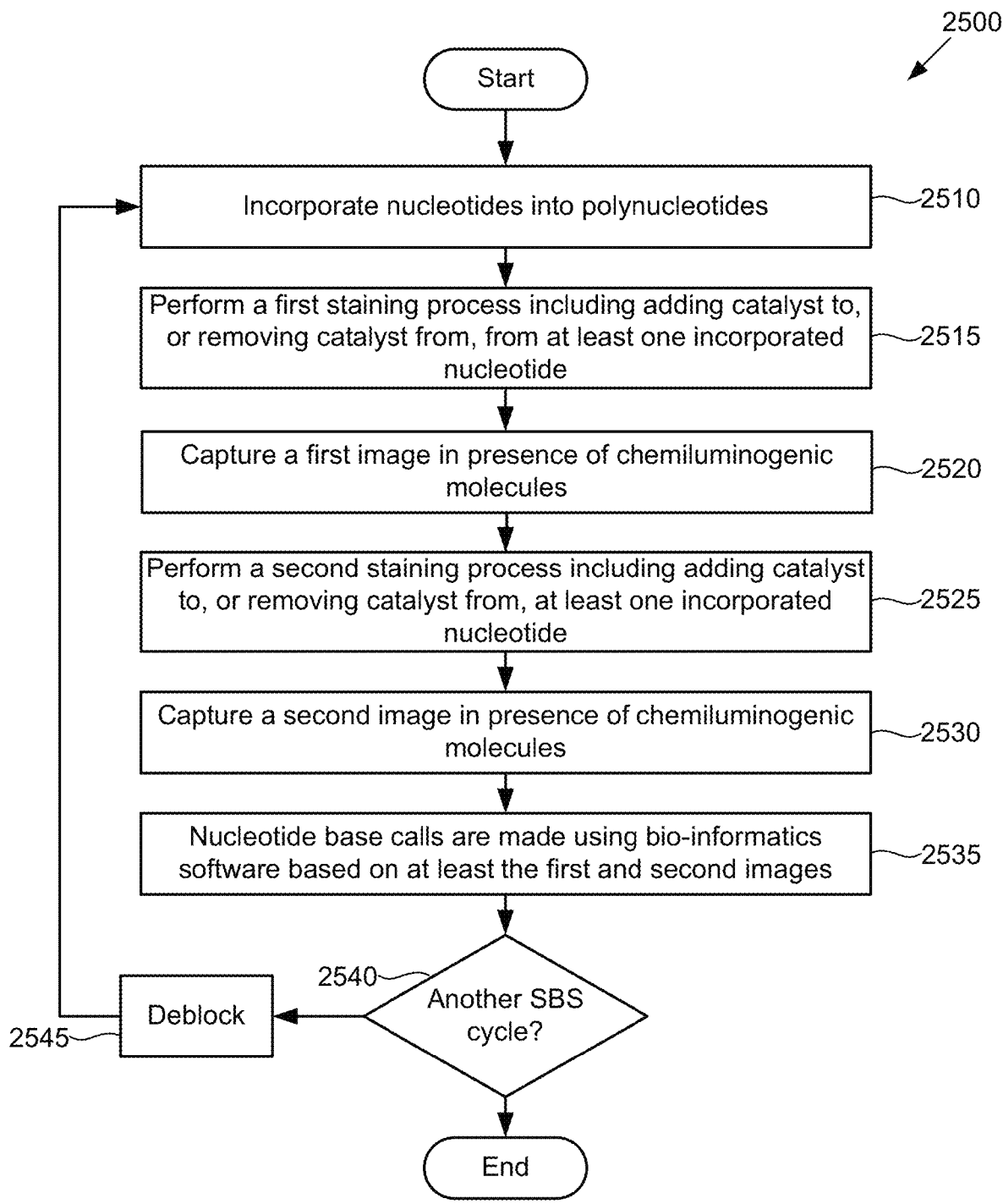
FIG. 25 illustrates a method for detecting the presence of nucleotides using in a polynucleotide using chemiluminescence, according to some embodiments of the present invention.
Figure 26:
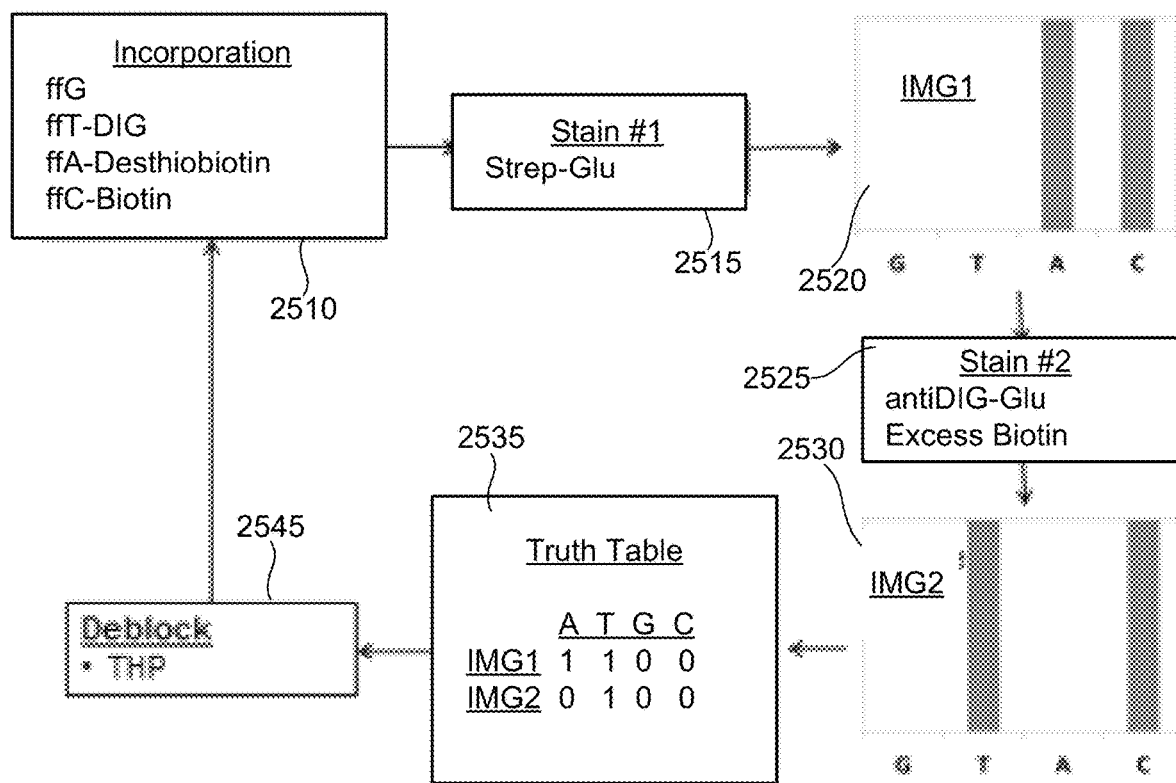
FIG. 26 illustrates a schematic diagram showing pictorially the steps of the method of FIG. 25, according to one exemplary embodiment of the present invention.

FIG. 25 illustrates a method for detecting the presence of nucleotides using in a polynucleotide using chemiluminescence, according to some embodiments of the present invention. In one example, method 2500 illustrated in FIG. 25 can be performed using flow cell 1600 of FIG. 16. FIG. 26 illustrates a schematic diagram showing pictorially the steps of method 2500 of FIG. 25.

In one illustrative embodiment, method 2500 uses hapten labeled fully functionalized (ff) nucleotides (ffA, ffT, ffC, and ffG), and hapten labeled *Gaussia* luciferase (Glu) enzyme, e.g., the "glow" form of Glu, for detection and discrimination of a nucleotide incorporation event. In one nonlimiting example, method 2500 uses digoxigenin (DIG)-labeled ffT (ffT-DIG) and Glu labeled with an antibody (or antibody fragment) specific for DIG (e.g., antiDIG-Glu) to detect incorporation of ffT, desthiobiotin-labeled ffA (ffA-Desthiobiotin), biotin labeled ffC (ffC-Biotin), and streptavidin-labeled Glu (strep-Glu) to detect incorporation of ffC and ffT. The ffG nucleotide can be "dark", e.g., ffG need not necessarily be labeled for detection. Other labeling schemes and other hapten pairs can be analogous to those described elsewhere herein. Referring now to FIG. 25, method 2500 includes, but is not limited to, the following steps.

At step 2510, nucleotides respectively are incorporated into polynucleotides, e.g., growing complementary strands, e.g., are incorporated into a second polynucleotide hybridized to a first polynucleotide that is hybridized to a corresponding one of sequencing primers 1622 illustrated in FIG. 16, using a polymerase (not specifically illustrated) in an SBS cycle. The nucleotide incorporated into a given one of such second polynucleotides can be ffT-DIG, ffA-Desthiobiotin, ffC-Biotin, or ffG, depending upon the particular sequence of the corresponding first polynucleotide. This step is also shown pictorially in the schematic diagram of FIG. 26. It should be appreciated that the nucleotides incorporated into different second polynucleotides can be different than one another, based on the different sequences of the first polynucleotides.

At step 2515, a first staining process is performed that includes adding catalyst to, or removing catalyst from, at least one incorporated nucleotide. In one nonlimiting example, a first exemplary staining process using strep-Glu is performed to detect incorporation of A and C nucleotides. For example, a first staining solution that includes strep-Glu can be flowed through flow cell 1600. Complex formation between any incorporated ffA-Desthiobiotin nucleotides and any incorporated ffC-Biotin nucleotides and strep-Glu selectively stains the corresponding clusters with the *Gaussia* luciferase enzyme. This step is also shown pictorially in the schematic diagram of FIG. 26.

At step 2520, a first image is captured in the presence of chemiluminogenic molecules. In one illustrative example, a first image is captured for detection of Glu signals resulting from binding of strep-Glu to both incorporated ffA-Desthiobiotin nucleotides and incorporated ffC-Biotin nucleotides. For example, using CMOS detector 1640 of flow cell 1600, a first image (e.g., IMG1) is captured for detection of Glu signals resulting from binding of strep-Glu to both incorporated ffA-Desthiobiotin nucleotides and incorporated ffC-Biotin nucleotides, following or during flow of a solution of appropriate chemiluminogenic molecules through flow cell 1600 to generate a localized chemiluminescent signal. This step is also shown pictorially in the schematic diagram of FIG. 26.

At step 2525, a second staining process is performed that includes adding catalyst to, or removing catalyst from, at least one incorporated nucleotide. In one example, a second staining process using antiDIG-Glu and excess biotin is performed to detect incorporation of T and A nucleotides. For example, a second staining solution that includes antiDIG-Glu and excess biotin is flowed through flow cell 1600. Complex formation between incorporated ffT-DIG nucleotides and antiDIG-Glu selectively stains a cluster with the *Gaussia* luciferase enzyme. Additionally, the excess biotin causes dissociation of strep-Glu from ffA-desthiobiotin, but substantially does not cause dissociation of strep-Glu from ffC-Biotin. This step is also shown pictorially in the schematic diagram of FIG. 26.

At step 2530, a second image is captured in the presence of chemiluminogenic molecules. In one example, a second image is captured for detection of an antiDIG-Glu signal from incorporated T nucleotides in addition to strep-Glu signal from incorporated C nucleotides. For example, using CMOS detector 1640 of flow cell 1600, a second image (e.g., IMG2) is captured following or during flow of chemiluminogenic molecules. The previous signal as in IMG1 is detected by the formation of an ffC-Biotin/strep-Glu(glow) binding complex and indicates incorporation of a C nucleotide into a corresponding second polynucleotide, and again appears in IMG2. A new signal caused by formation of an ffT-DIG/antiDIG-Glu binding complex appears in IMG2, while the signal in IMG1 corresponding to an ffA-desthiobiotin/strep-Glu complex disappears as a result of the dissociation of such complex resulting from the flow of excess biotin. This step is also shown pictorially in the schematic diagram of FIG. 26.

At step 2535, nucleotide base calls are made using bioinformatics software based on at least the first and second images. In this example, incorporation of A is detected as a signal that appears in the first image but not the second image, incorporation of T is detected as a signal that is absent in the first image and present in the second image, incorporation of C is detected as a signal in both the first and second images, and incorporation of G is determined based on the lack of a signal in both the first and second images. This step is also shown pictorially in the schematic diagram of FIG. 26 in the form of a truth table wherein the "1" in each row means that the nucleotide in that column corresponds to a bright signal (either glow or flash) in the corresponding image.

At decision step 2540, it is determined whether another cycle of SBS is desired. If another SBS cycle is desired, then method 2500 proceeds to step 2545. If another SBS cycle is not desired, then method 2500 ends.

At a step 2545, a deblocking reaction is performed to remove a blocking group on each of the incorporated nucleotides so as to facilitate the next nucleotide addition in the next SBS cycle. Method 2500 returns to step 2510. This step is also shown pictorially in the schematic diagram of FIG. 26.

Figure 27:
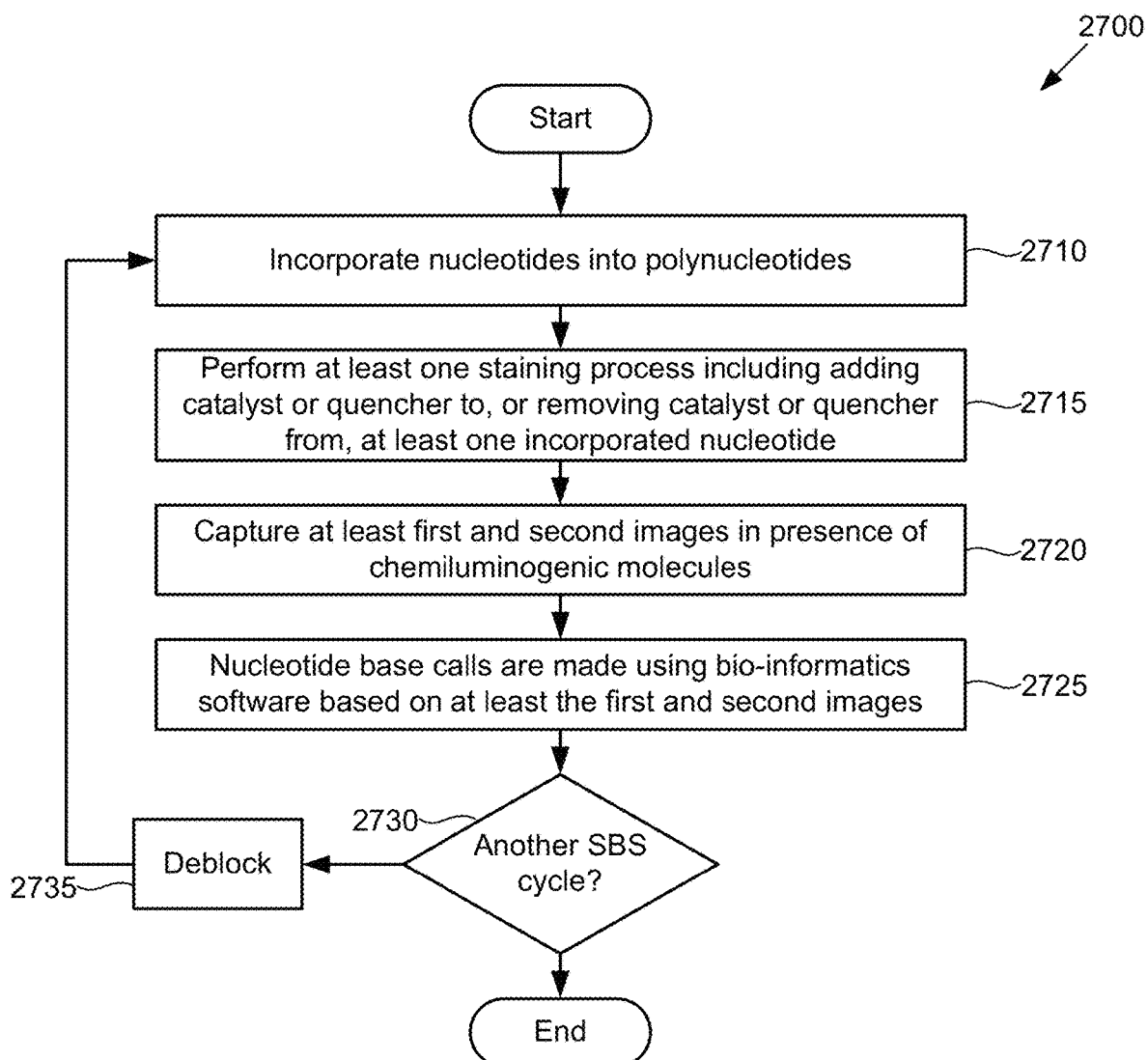
FIG. 27 illustrates a method for detecting the presence of nucleotides using in a polynucleotide using chemiluminescence, according to some embodiments of the present invention.

FIG. 27 illustrates yet another exemplary method for detecting the presence of nucleotides using in a polynucleotide using chemiluminescence, according to some embodiments of the present invention. FIG. 27 can be implemented using any suitable composition or device, including but not limited to the compositions and devices provided herein.

At step 2710, nucleotides respectively are incorporated into polynucleotides, e.g., growing complementary strands, e.g., are incorporated into a second polynucleotide hybridized to a first polynucleotide. It should be appreciated that the nucleotides incorporated into different second polynucleotides can be different than one another, based on the different sequences of the first nucleotides. At step 2715, at least one staining process is performed that includes adding catalyst or quencher to, or removing catalyst or quencher from, at least one incorporated nucleotide in any suitable manner, including but not limited to those provided herein. At step 2720, at least first and second images are captured in the presence of chemiluminogenic molecules in any suitable manner, including but not limited to those provided herein. Note that the first and second images can be taken in any suitable order relative to one another and relative to the at least one staining process of step 2715. At step 2725, nucleotide base calls are made using bio-informatics software based on at least the first and second images in any suitable manner, including but not limited to those provided herein. At decision step 2730, it is determined whether another cycle of SBS is desired. If another SBS cycle is desired, then method 2700 proceeds to step 2735. If another SBS cycle is not desired, then method 2700 ends. At a step 2735, a deblocking reaction is performed to remove a blocking group on each of the incorporated nucleotides so as to facilitate the next nucleotide addition in the next SBS cycle. Method 2700 returns to step 2710. This step is also shown pictorially in the schematic diagram of FIG. 26.

It should be appreciated that method 2700 also represents steps that can be performed in a variety of different exemplary methods for detecting the presence of polymer subunits, such as nucleotides in polynucleotides, using chemiluminescence. For example, method 700 described further above with reference to FIG. 7 includes a step of adding a nucleotide of a plurality of nucleotides to a second polynucleotide based on the sequence of a first polynucleotide (step 704 of method 700), corresponding to incorporating nucleotides into polynucleotides (step 2710 of method 2700). Method 700 also includes steps of exposing the nucleotide to a catalyst coupled to a fifth moiety (step 705 of method 700), exposing the nucleotide to a catalyst coupled to a sixth moiety (step 708 of method 700), and exposing the nucleotide to a cleaver molecule (step 711 of method 700), each of which steps corresponds to performing at least one staining process including adding catalyst to, or removing catalyst from, at least one incorporated nucleotide (step 2715 of method 2700). Method 700 also includes steps of detecting emission of photons or absence of photons from chemiluminogenic molecules (steps 707, 710, and 713 of method 700), corresponding to capturing at least first and second images for base discrimination (step 2720 of method 2700). Method 700 also includes detecting the nucleotide added at step 704 based on detection of emission of photons or absence of photons at least at steps 707 and 710, or 713 or a combination thereof (step 714 of method 700), corresponding to nucleotide base calls being made using bio-informatics software based on at least first and second images (step 2725 of method 2700). Following step 714 of method 700, it can be determined whether to again contact the second nucleotide with polymerase and a plurality of nucleotides, corresponding to decision to conduct another SBS cycle (step 2730 of method 2700). If so, a deblocking step can be performed prior to executing step 703 again, corresponding to deblock (step 2735 of method 2700).

As another example, method 900 described further above with reference to FIG. 9 includes a step of adding a nucleotide of a plurality of nucleotides to a second polynucleotide based on the sequence of a first polynucleotide (step 904 of method 900), corresponding to incorporating nucleotides into polynucleotides (step 2710 of method 2700). Method 900 also includes steps of exposing the nucleotide to a quencher coupled to a fifth moiety (step 905 of method 900), exposing the nucleotide to a quencher coupled to a sixth moiety (step 908 of method 900), and exposing the nucleotide to a cleaver molecule (step 911 of method 900), each of which steps corresponds to performing at least one staining process including adding quencher to, or removing quencher from, at least one incorporated nucleotide (step 2715 of method 200). Method 900 also includes steps of detecting emission of photons or absence of photons from chemiluminogenic molecules (steps 907, 910, and 913 of method 900), corresponding to capturing at least first and second images in the presence of chemiluminogenic molecules (step 2720 of method 2700). Method 900 also includes detecting the nucleotide added at step 904 based on detection of emission of photons or absence of photons at least at steps 907, 910, or 913 or a combination thereof (step 914 of method 900), corresponding to nucleotide base calls being made using bio-informatics software based on at least first and second images (step 2725 of method 2700). Following step 914 of method 900, it can be determined whether to again contact the second nucleotide with polymerase and a plurality of nucleotides, corresponding to decision to conduct another SBS cycle (step 2730 of method 2700). If so, a deblocking step can be performed prior to executing step 903 again, corresponding to deblock (step 2735 of method 2700).

As another example, method 1700 described further above with reference to FIG. 17 includes a step of incorporating nucleotides into polynucleotides (step 1710 of method 1700), corresponding to incorporating nucleotides into polynucleotides (step 2710 of method 2700). Method 1700 also includes steps of performing a first staining process including adding catalyst to, or removing catalyst from, at least one incorporated nucleotide (step 1715 of method 1700) and performing a second staining process including adding catalyst to, or removing catalyst from, at least one incorporated nucleotide (step 1730 of method 1700), corresponding to performing at least one staining process including adding catalyst to, or removing catalyst from, at least one incorporated nucleotide (step 2715 of method 2700). Method 1700 also includes steps of capturing a first image in the presence of chemiluminogenic molecules, (step 1720 of method 1700), a second image in the presence of chemiluminogenic molecules (step 1725 of method 1700), and a third image in the presence of chemiluminogenic molecules (step 1735 of method 1700), corresponding to capturing at least first and second images for base discrimination (step 2720 of method 2700). Method 1700 also includes nucleotide base calls being made using bio-informatics software based on at least the first, second, and third images (step 1740 of method 1700), corresponding to nucleotide base calls being made using bio-informatics software based on at least first and second images (step 2725 of method 2700). Like method 2700, method 1700 also includes a decision to conduct another SBS cycle (step 1745 of method 1700 and step 2730 of method 2700) and a deblock step (step 1750 of method 1700 and step 2735 of method 2700).

As yet another example, method 2000 described further above with reference to FIG. 20 includes a step of incorporating nucleotides into polynucleotides (step 2010 of method 2000), corresponding to incorporating nucleotides into polynucleotides (step 2710 of method 200). Method 2000 also includes steps of capturing a first image in the presence of chemiluminogenic molecules (step 2015 of method 2000) and capturing a second image in the presence of chemiluminogenic molecules (step 2025 of method 2000), corresponding to capturing at least first and second images for base discrimination (step 2720 of method 2700). Method 2000 also includes a step of performing at least one staining process including adding catalyst to, or removing catalyst from, at least one incorporated nucleotide, illustratively, flowing a hapten-labeled catalyst, such as strep-cat, and a cleaver molecule, such as SS-cleaver solution (step 2020 of method 2000), corresponding to performing at least one staining process including adding catalyst to, or removing catalyst from, at least one incorporated nucleotide (step 2715 of method 2700). Method 2000 also includes nucleotide base calls being made using bio-informatics software based on at least the first and second images (step 2030 of method 2000), corresponding to nucleotide base calls being made using bio-informatics software based on at least first and second images (step 2725 of method 2700). Like method 2700, method 2000 also includes a decision to conduct another SBS cycle (step 2035 of method 2000 and step 2730 of method 2700) and a deblock step (step 2040 of method 2000 and step 2735 of method 2700).

As yet another example, method 2500 described further above with reference to FIG. 25 includes a step of incorporating nucleotides into polynucleotides (step 2510 of method 2500), corresponding to incorporating nucleotides into polynucleotides (step 2710 of method 2700). Method 2500 also includes steps of performing a first staining process including adding catalyst to, or removing catalyst from, at least one incorporated nucleotide (step 2515 of method 2500) and performing a second staining process including adding catalyst to, or removing catalyst from, at least one incorporated nucleotide (step 2525 of method 2500), corresponding to performing at least one staining process including adding catalyst to, or removing catalyst from, at least one incorporated nucleotide (step 2715 of method 2700). Method 2500 also includes steps of capturing a first image in the presence of chemiluminogenic molecules, (step 2520 of method 2500), and a second image in the presence of chemiluminogenic molecules (step 2530 of method 2500), corresponding to capturing at least first and second images for base discrimination (step 2720 of method 2700). Method 2500 also includes nucleotide base calls being made using bio-informatics software based on at least the first and second images (step 2535 of method 2500), corresponding to nucleotide base calls being made using bio-informatics software based on at least first and second images (step 2725 of method 2700). Like method 2700, method 2500 also includes a decision to conduct another SBS cycle (step 2540 of method 2500 and step 2730 of method 2700) and a deblock step (step 2545 of method 2500 and step 2735 of method 2700).

Figure 28:
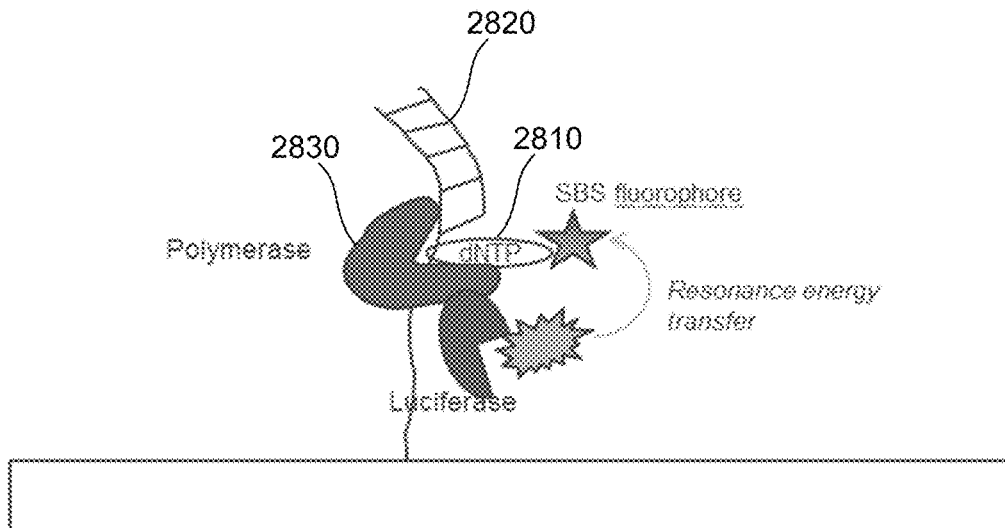
FIG. 28 schematically illustrates an alternative composition for detecting the presence of polymer subunits using chemiluminescence, according to some embodiments of the present invention.

FIG. 28 schematically illustrates an alternative composition for detecting the presence of polymer subunits using chemiluminescence, according to some embodiments of the present invention. Instead of coupling an incorporated nucleotide 2810 to a catalyst (e.g., a nucleotide that is labeled prior to incorporation into polynucleotide 2820, or labeled via a hapten complex following incorporation into polynucleotide 2820), a fusion protein 2830 of polymerase and luciferase can be used. For further details on fusion proteins of polymerase and luciferase, see Kobatake et al., "Bioluminescent immunoassay with a protein A-luciferase fusion protein," Analytical Biochemistry 208(2): 300-305 (Feb. 1, 1993), the entire contents of which are incorporated by reference herein. The incorporated nucleotide can be labeled with a fluorophore (e.g., labeled prior to incorporation into polynucleotide 2820, or labeled via a hapten complex following incorporation into polynucleotide 2820), and can be excited using bioluminescence resonance energy transfer (BRET). For further details of BRET, see Boute et al., "The use of resonance energy transfer in high-throughput screening: BRET versus FRET," Trends in Pharmacological Sciences 23(8): 351-354 (Aug. 1, 2002), the entire contents of which are incorporated by reference herein. Such a scheme can reduce the need for additional staining steps or the use of nucleotides that are coupled to haptens, catalysts, and/or quenchers, and also can obviate the need for external sources of illumination.

Figure 29:
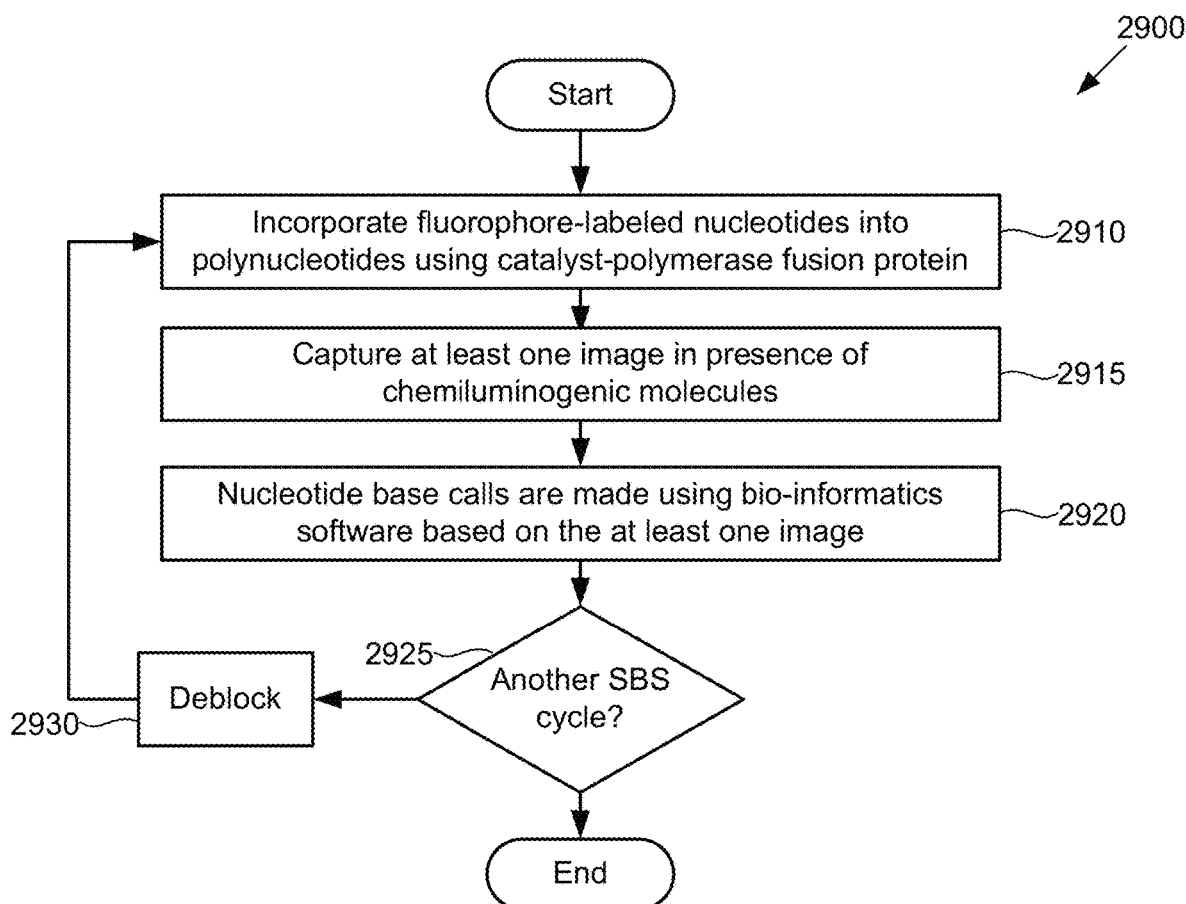
FIG. 29 illustrates a method for detecting the presence of nucleotides using in a polynucleotide using chemiluminescence, according to some embodiments of the present invention.

FIG. 29 illustrates an exemplary method for detecting the presence of nucleotides using in a polynucleotide using chemiluminescence, according to some embodiments of the present invention. FIG. 29 illustratively can be implemented using the composition illustrated in FIG. 28, but can be implemented using any suitable composition or device.

At step 2910, nucleotides respectively are incorporated into polynucleotides using a catalyst-polymerase fusion protein. FIG. 28 illustrates an exemplary luciferase-polymerase fusion protein, but it should be appreciated that any suitable fusion protein between polymerase and a catalyst such as described herein can be used. The fusion protein can incorporate the nucleotides into corresponding polynucleotides, e.g., growing complementary strands, e.g., into a second nucleotide hybridized to a first nucleotide. It should be appreciated that the nucleotides incorporated into different second polynucleotides can be different than one another, based on the different sequences of the first polynucleotides.

At step 2915, at least one image is captured in the presence of chemiluminogenic molecules in any suitable manner, including but not limited to those provided herein. In the embodiment illustrated in FIG. 29 and exemplified in FIG. 28, the chemiluminogenic molecules interact with the catalyst portion of the fusion protein, e.g., interact with the luciferase illustrated in FIG. 28, and emit photons responsive to such interaction. Such photons then interact with the fluorophore labels on incorporated nucleotides, causing the fluorophore labels to emit photons having a wavelength based upon which the respective incorporated nucleotide can be identified. Methods of identifying nucleotides based on photon emissions from fluorophore labels coupled thereto are known At step 2920, nucleotide base calls are made using bio-informatics software based on the at least one image in any suitable manner, including but not limited to those provided herein. At decision step 2925, it is determined whether another cycle of SBS is desired. If another SBS cycle is desired, then method 2900 proceeds to step 2930. If another SBS cycle is not desired, then method 2900 ends. At a step 2930, a deblocking reaction is performed to remove a blocking group on each of the incorporated nucleotides so as to facilitate the next nucleotide addition in the next SBS cycle. Method 2900 returns to step 2910.

Other Alternative Embodiments

It should be noted that the systems and methods provided herein can be implemented using various types of data processor environments (e.g., on one or more data processors) which execute instructions (e.g., software instructions) to perform operations disclosed herein. Non-limiting examples include implementation on a single general purpose computer or workstation, or on a networked system, or in a client-server configuration, or in an application service provider configuration. For example, the methods and systems described herein can be implemented on many different types of processing devices by program code comprising program instructions that are executable by the device processing subsystem. The software program instructions can include source code, object code, machine code, or any other stored data that is operable to cause a processing system to perform the methods and operations described herein. Other implementations can also be used, however, such as firmware or even appropriately designed hardware configured to carry out the methods and systems described herein. For example, a computer can be programmed with instructions to perform the various steps of the flowcharts shown in FIG. 2, 4, 7, 9, 17, 20, 25, 27, or 29.

It is further noted that the systems and methods can include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

The systems' and methods' data (e.g., associations, data input, data output, intermediate data results, final data results, etc.) can be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods further can be provided on many different types of computer-readable storage media including computer storage mechanisms (e.g., non-transitory media, such as CD-ROM, diskette, RAM, flash memory, computer's hard drive, etc.) that contain instructions (e.g., software) for use in execution by a processor to perform the methods' operations and implement the systems described herein.

Moreover, the computer components, software modules, functions, data stores and data structures provided herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand.

While various illustrative embodiments of the invention are described above, it will be apparent to one skilled in the art that various changes and modifications may be made therein without departing from the invention. For example, although certain compositions, systems, and methods are discussed above with reference to detecting the presence of nucleotides in polynucleotides, it should be understood that the present compositions, systems, and methods suitably can be adapted for use in detecting the presence of any type of polymer subunit that can be associated with chemiluminescence or an absence thereof. The appended claims are intended to cover all such changes and modifications that fall within the true spirit and scope of the invention.

What is claimed:

1. A composition including:
  a substrate;
  a first polynucleotide coupled to the substrate;
  a second polynucleotide hybridized to the first polynucleotide;
  a catalyst coupled to a first nucleotide at the 3' end of the second polynucleotide, wherein the catalyst is operable to cause a chemiluminogenic molecule to emit a photon, wherein the first nucleotide is coupled to a first moiety, and the catalyst is coupled to a second moiety, wherein the first nucleotide and the catalyst are coupled via the first and second moieties; and
  a polymerase capable of extending the second polynucleotide hybridized to the first polynucleotide.

2. The composition of claim 1, wherein the catalyst is selectively cleavable from the first nucleotide.

3. The composition of claim 1, wherein the catalyst includes a luciferase.

4. The composition of claim 3, wherein the chemiluminogenic molecule comprises luciferin or coelenterazine.

5. The composition of claim 1, wherein the catalyst includes a peroxide generator.

6. The composition of claim 5, wherein the peroxide generator comprises a peroxide catalyst selected from the group consisting of an enzyme, a metallic catalyst, an organic catalyst, and a metalorganic catalyst; and wherein the chemiluminogenic molecule comprises a substituent selected from the group consisting of luminol, a luminol derivative, and acridinium.

7. A system comprising:
  the composition of claim 1, wherein the catalyst coupled to a first nucleotide is a first catalyst;
  a plurality of nucleotides comprising:
    a first subset of nucleotides comprising the first moiety,
    a second subset of nucleotides comprising a third moiety,
    a third subset of nucleotide comprising a fourth moiety, and
    a fourth subset of nucleotides comprising a fifth moiety;
  wherein the second moiety of the first catalyst is capable of selectively coupling to one, two or three moieties selected from the first, third, fourth, or fifth moieties;
  a second catalyst coupled to a sixth moiety, wherein the sixth moiety is capable of selectively coupling to one, two or three moieties selected from the first, third, fourth, or fifth moieties;
  a cleaving agent capable of selectively cleaving one or more linkages between the second moiety and any one of the first, third, fourth or fifth moieties, or between the sixth moiety and any one of the first, third, fourth, or fifth moieties; and circuitry configured to detect the photon emitted by the chemiluminogenic molecule.

8. A method for sequencing a nucleic acid, comprising:
providing the composition of claim 1, wherein the catalyst coupled to a first nucleotide is a first catalyst; and
contacting the first catalyst with a first chemiluminogenic molecule, such that the first chemiluminogenic molecule emits a photon.

9. The method of claim 8 further comprising extending the second polynucleotide by adding a second nucleotide to the first nucleotide in the presence of the polymerase.

10. The method of claim 9, further comprising selectively cleaving the first catalyst from the first nucleotide before the contacting the polymerase with the first and second polynucleotides.

11. The method of claim 10, further comprising extending the second polynucleotide by adding the second nucleotide to the first nucleotide after the contacting the polymerase with the first and second polynucleotides.

12. The method of claim 11, further including coupling a second catalyst to the second nucleotide.

13. The method of claim 8, wherein the catalyst includes a luciferase.

14. The method of claim 13, wherein the chemiluminogenic molecule comprises luciferin or coelenterazine.

15. The method of claim 8, wherein the catalyst includes a peroxide generator.

16. The method of claim 15, wherein the peroxide generator comprises a peroxide catalyst selected from the group consisting of an enzyme, a metallic catalyst, an organic catalyst, and a metalorganic catalyst; and wherein the chemiluminogenic molecule comprises a substituent selected from the group consisting of luminol, a luminol derivative, and acridinium.

17. The method of claim 8, further including detecting the photon emitted by the first chemiluminogenic molecule, thereby detecting the presence of the first nucleotide.

18. The method of claim 8, wherein the providing comprises: incorporating the first nucleotide into the polynucleotide by contacting the polynucleotide with a plurality of nucleotides in the presence of the polymerase, wherein the plurality of nucleotides comprises:
a first subset of nucleotides comprising the first moiety,
a second subset of nucleotides comprising a third moiety,
a third subset of nucleotide comprising a fourth moiety, and
a fourth subset of nucleotides comprising a fifth moiety; and
contacting the first nucleotide with the catalyst coupled to the second moiety, wherein the second moiety is capable of selectively coupling to at least the first moiety, and optionally to one or two moieties selected from the third, fourth, or fifth moieties; and
determining the identity of the first nucleotide by:
(i) the contacting the catalyst with a first chemiluminogenic molecule, such that the first chemiluminogenic molecule emits a photon;
(ii) detecting the presence of the catalyst coupled to the incorporated nucleotide,
(iii) contacting the first nucleotide with a second catalyst coupled to a sixth moiety, wherein the sixth moiety is capable of selectively coupling to one, two or three moieties selected from the first, third, fourth, or fifth moieties,
(v) detecting the presence or absence of the second catalyst coupled to the first nucleotide,
(vi) contacting the first nucleotide with a cleaving agent, wherein the cleaving agent is capable of selectively cleaving one or more linkages between the second moiety and any one of the first, third, fourth or fifth moieties, or between the sixth moiety and any one of the first, third, fourth, or fifth moieties,
(vii) detecting the presence or absence of the first or second catalyst coupled to the incorporated nucleotide, thereby determining the identity of the incorporated nucleotide.

* * * * *

UNITED STATES PATENT AND TRADEMARK OFFICE
CERTIFICATE OF CORRECTION

PATENT NO. : 10,633,694 B2
APPLICATION NO. : 15/507465
DATED : April 28, 2020
INVENTOR(S) : Boyan Boyanov It is certified that error appears in the above-identified patent and that said Letters Patent is hereby corrected as shown below:

On the Title Page

Page 2, Column 2, item (56), Other Publications, Line 17, delete "chmiluminescence" and insert --chemiluminescence--.

In the Drawings

In sheet 32 of 35, FIG. 25, reference numeral 2515, Line 2, delete "from at" and insert --at--.

In the Specification

Column 1, Line 11, delete "WO 20016/040607" and insert --WO 2016/040607--.

Column 14, Line 24, delete "xathanine" and insert --xanthine--.

Column 14, Line 25, delete "hypoxathanine" and insert --hypoxanthine--.

Column 14, Line 28, delete "thioLiracil" and insert --thiouracil--.

Column 19, Line 34, delete "deshydrogenase" and insert --dehydrogenase--.

Column 19, Line 35, delete "deshydrogenase" and insert --dehydrogenase--.

Column 23, Line 13, delete "Maastrict" and insert --Maastricht--.

Column 42, Line 61, delete "k." and insert --$\lambda$.--.

Column 44, Line 13, delete "polymerbased" and insert --polymer based--.

Column 64, Line 41 (approx.), delete "known" and insert --known.--.

Signed and Sealed this
Eighteenth Day of August, 2020

Andrei Iancu
*Director of the United States Patent and Trademark Office*

In the Claims

Column 70, Line 27 (approx.), in Claim 18, delete "(v)" and insert --(iv)--.

Column 70, Line 29, Claim 18, delete "(vi)" and insert --(v)--.

Column 70, Line 36 (approx.), Claim 18, delete "(vii)" and insert --(vi)--.

SEQUENCE LISTING

```
<160> NUMBER OF SEQ ID NOS: 6

<210> SEQ ID NO 1
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
atcggattcg ataacagtca atgtaatgac ca                                      32

<210> SEQ ID NO 2
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
atcggattcg ataacagtcg tggtaatgac ca                                      32

<210> SEQ ID NO 3
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
```

```
        Synthetic oligonucleotide"

<400> SEQUENCE: 3
atcggattcg ataacagtca tggtaatgac ca                                32

<210> SEQ ID NO 4
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 4
atcggattcg ataacagtca ttgtaatgac ca                                32

<210> SEQ ID NO 5
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 5
atcggattcg ataacagtca tagtaatgac ca                                32

<210> SEQ ID NO 6
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 6
atcggattcg ataacagtca tcgtaatgac ca                                32
```